United States Patent
Wang et al.

(10) Patent No.: US 11,939,323 B2
(45) Date of Patent: Mar. 26, 2024

(54) METHODS OF MAKING A MODULATOR OF HEMOGLOBIN

(71) Applicant: Global Blood Therapeutics, Inc., South San Francisco, CA (US)

(72) Inventors: Xiang Wang, South San Francisco, CA (US); Shinji Fujimori, San Francisco, CA (US); Todd Daniel Nelson, Cream Ridge, NJ (US); Ana Cristina Parra Rivera, Plainsboro, NJ (US); Devon Mundal, Seattle, WA (US); Benjamin Graetz, San Mateo, CA (US); Morin M. Frick, San Mateo, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/744,525

(22) Filed: May 13, 2022

(65) Prior Publication Data

US 2022/0388996 A1    Dec. 8, 2022

Related U.S. Application Data

(60) Provisional application No. 63/188,735, filed on May 14, 2021.

(51) Int. Cl.
C07D 413/06    (2006.01)

(52) U.S. Cl.
CPC .................. C07D 413/06 (2013.01)

(58) Field of Classification Search
CPC .................................................. C07D 413/06
See application file for complete search history.

(56) References Cited

U.S. PATENT DOCUMENTS

| 10,683,285 B2 | 8/2020 | Li |
| 11,548,880 B2 | 1/2023 | Li |
| 2015/0209443 A1 | 7/2015 | Metcalf |
| 2020/0157085 A1* | 5/2020 | Li ..................... A61K 31/5377 |

FOREIGN PATENT DOCUMENTS

| WO | WO 2020/106642 A1 | 5/2020 |
| WO | WO 2020/127924 A1 | 6/2020 |

OTHER PUBLICATIONS

International Search Report and Written Opinion dated Sep. 7, 2022 for PCT Application No. PCT/US2022/029304. 8 pages.

* cited by examiner

*Primary Examiner* — Deepak R Rao

(57) ABSTRACT

The present disclosure relates to processes for preparing a compound of formula I:

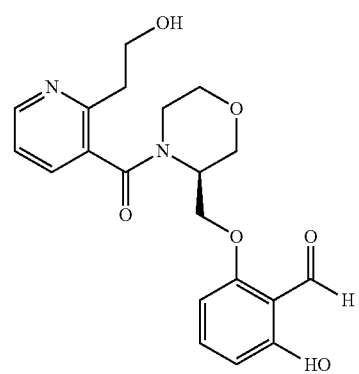

The disclosure also provides compounds that are synthetic intermediates.

19 Claims, No Drawings

METHODS OF MAKING A MODULATOR OF HEMOGLOBIN

CROSS-REFERENCE TO RELATED APPLICATIONS

This application claims the benefit under 35 U.S.C. § 119(e) of U.S. Provisional Application No. 63/188,735, filed May 14, 2021, which is hereby incorporated by reference in its entirety.

FIELD

The present disclosure relates generally to the field of organic synthetic methodology for the preparation of compounds that modulate hemoglobin and the synthetic intermediates prepared thereby.

BACKGROUND

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin A (HbA).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, making HbS susceptible to polymerization under hypoxic conditions to give the HbS containing red blood cells their characteristic sickle shape. The sickled cells are also more rigid than normal red blood cells, and their lack of flexibility can lead to blockage of blood vessels.

Compounds that modulate hemoglobin and are useful in treating disorders mediated by abnormal Hb (such as HbS) are disclosed in U.S. Pat. No. 10,683,285, the disclosure of which is hereby incorporated by reference in its entirety.

There remains a need for improved or alternate processes to prepare compounds that are modulators of hemoglobin.

SUMMARY

Provided herein are methods for preparing a compound of formula I:

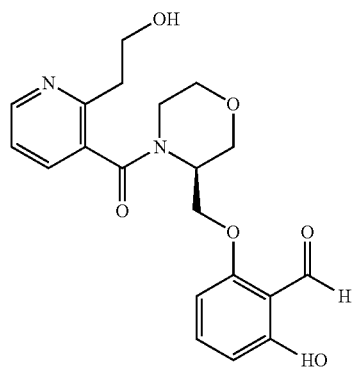

I

Also provided herein are intermediates useful for methods of making a compound of Formula I.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

Reference to "about" a value or parameter herein includes (and describes) embodiments that are directed to that value or parameter per se. In other embodiments, the term "about" includes the indicated value or parameter ±5%. In certain other embodiments, the term "about" includes the indicated value or parameter ±2.5%. In certain other embodiments, the term "about" includes the indicated value or parameter ±2%. In some other embodiments, the term "about" includes the indicated value or parameter ±1%. In some other embodiments, the term "about" includes the indicated value or parameter ±0.5%. Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

The terms "optional" or "optionally" means that the subsequently described event or circumstance may or may not occur, and that the description includes instances where said event or circumstance occurs and instances in which it does not.

The prefix "$C_{u-v}$" indicates that the following group has from u to v carbon atoms. For example, "$C_{1-6}$ alkyl" indicates that the alkyl group has from 1 to 6 carbon atoms.

"Alkyl" refers to an unbranched or branched saturated hydrocarbon chain. As used herein, alkyl has 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl regardless of the point of attachment. If one or more aryl groups are fused with a heterocyclyl, the resulting ring system is heterocyclyl regardless of the point of attachment.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Halogen" or "halo" refers to atoms occupying group VIIA of the periodic table, such as fluoro, chloro, bromo or iodo.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclic ring" or "heterocyclyl" or "heterocycloalkyl" refers to a saturated or partially unsaturated cyclic alkyl group, with one or more ring heteroatoms independently selected from nitrogen, sulfur or oxygen. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

The term "reaction conditions" is intended to refer to the physical and/or environmental conditions under which a chemical reaction proceeds. The term "under conditions sufficient to" or "under reaction conditions sufficient to" is intended to refer to the reaction conditions under which the desired chemical reaction may proceed. Examples of reaction conditions include, but are not limited to, one or more of following: reaction temperature, solvent, pH, pressure, reaction time, mole ratio of reactants, mole ratio of reagents, the presence of a base or acid, or catalyst, radiation, concentration, etc. Reaction conditions may be named after the particular chemical reaction in which the conditions are employed, such as, coupling conditions, hydrogenation conditions, acylation conditions, reduction conditions, halogenation conditions etc. Reaction conditions for most reactions are generally known to those skilled in the art or may be readily obtained from the literature. Exemplary reaction conditions sufficient for performing the chemical transformations provided herein may be found throughout the present disclosure, and in particular, the examples below. It is also contemplated that the reaction conditions may include reagents in addition to those listed in the specific reaction.

The term "reagent" refers to a substance or compound that may be added to bring about a chemical reaction.

The terms "solvent" or "inert solvent" refer to a solvent inert under the conditions of the reaction being described in conjunction therewith.

In some embodiments, the solvent is an "organic solvent" or "inert organic solvent," which includes, for example, benzene, toluene, acetonitrile, tetrahydrofuran ("THF"), dimethylformamide ("DMF"), chloroform, methylene chloride (or dichloromethane), diethyl ether, methanol, pyridine, and the like. Unless specified to the contrary, the solvents used in the reactions of the present disclosure are inert organic solvents, and the reactions are carried out under an inert gas, such as nitrogen.

The term "coupling reagent" or "coupling agent" refers to a compound that aids in bringing about a reaction to couple one compound to another compound.

The term "metalating reagent" refers to a compound of the generic formula $X-M-R_n$, where M is a metal, R is an alkyl or aryl, and X is a counterion, such as a halide or alkali metal which may or may not be present. Exemplary metalating reagents include, but are not limited to, isopropyl magnesium chloride, methyl magnesium chloride, n-butyl magnesium chloride, phenyl magnesium chloride, lithium dimethylcopper, lithium diethylcopper, and lithium di-n-butylcopper.

The term "reducing agent" or "reductant" refers to an element or compound that loses an electron to an oxidizing agent in a redox reaction. Reducing agents increase the electron density on carbon centers, either by bond formation between the carbon and a less electronegative atom, or by bond breaking between the carbon and a more electronegative atom. Reducing agents usually accomplish this change in electron density by the addition of hydrogen, or the substitution of hydrogen for an electronegative atom on the carbon center.

The term "deprotecting reagent" refers to a compound that aids in removal of a protecting group (such as a hydroxy protecting group or amine protecting group).

The term "leaving group" refers to an atom or a group of atoms that is displaced in a chemical reaction as stable species taking with it the bonding electrons. The non-limiting examples of a leaving group include, halo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, (4-methoxy-benzene)sulfonyloxy, and the like.

The term "hydroxy protecting group" refers to a chemical moiety which is added to, and later removed from, a hydroxy functionality to obtain chemoselectivity in a subsequent chemical reaction. Exemplary protecting groups, as well as the methods for deprotection, include, but are not limited to, acetyl (Ac) (removed by acid or base), benzoyl (Bz) (removed by acid or base), benzyl (Bn) (removed by hydrogenolysis), β-methoxyethoxymethyl ether (MEM) (removed by acid), dimethoxytrityl or [bis-(4-methoxyphenyl)phenylmethyl] (DMT) (removed by weak acid), methoxymethyl ether (MOM) (removed by acid), methoxytrityl or [(4-methoxyphenyl)diphenylmethyl] (MMT) (removed by acid and hydrogenolysis), p-methoxybenzyl ether (PMB) (removed by acid, hydrogenolysis, or oxidation), methylthiomethyl ether (removed by acid), pivaloyl (Piv) (removed by acid, base or reductant agents), tetrahydropyranyl (THP) (removed by acid), tetrahydrofuran (THF) (removed by acid), trityl (triphenylmethyl, Tr) (removed by acid and hydrogenolysis), silyl ether (e.g., trimethylsilyl (TMS), tert-butyldimethylsilyl (TBDMS), tri-iso-propylsilyloxymethyl (TOM), and triisopropylsilyl (TIPS) ethers) (removed by acid or fluoride ion, such as NaF, TBAF (tetra-n-butylammonium fluoride, HF-Py, or HF-NEt$_3$)), methyl ethers (removed by cleavage is by TMSI in dichloromethane or acetonitrile or chloroform, or BBr$_3$ in DCM), and ethoxyethyl ethers (EE) (removed by 1N hydrochloric acid).

The term "amine protecting group" refers to a chemical moiety which is added to, and later removed from, an amine functionality to obtain chemoselectivity in a subsequent chemical reaction. Exemplary protecting groups, as well as the methods for deprotection, include, but are not limited to, 9-fluorenylmethoxycarbonyl (Fmoc) (removed by base), tert-butyloxycarbonyl (Boc) (removed by strong acid), carboxybenzyl (Cbz) (removed by hydrogenolysis), acetyl (Ac) (removed by base), benzyl (Bn) (removed by hydrogenolysis), benzoyl (Bz) (removed by base), carbamate (removed by acid and mild heating), p-methoxybenzyl (PMB) (removed by hydrogenolysis), 3,4-dimethoxybenzyl (DMPM) (removed by hydrogenolysis), p-methoxyphenyl (PMP) (removed by ammonium cerium(IV) nitrate (CAN)), tosyl (Ts) (removed by concentrated acid and strong reducing agents), and 2,2,2-trichloroethoxycarbonyl (Troc) (removed by Zn insertion in the presence of acetic acid).

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example, those into which radioactive isotopes such as $^3$H and $^{14}$C are incorporated, are provided herein. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines. Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. Acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

In some cases, the "salt" of a given compound is a pharmaceutically acceptable salt. The term "pharmaceutically acceptable salt" of a given compound refers to salts that retain the biological effectiveness and properties of the given compound, and which are not biologically or otherwise undesirable. Pharmaceutically acceptable base addition salts may be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines. Specific examples of suitable amines include, by way of example only, isopropylamine, trimethyl amine, diethyl amine, tri(iso-propyl) amine, tri(n-propyl) amine, ethanolamine, diethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Provided are also pharmaceutically acceptable salts, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "solid form" refers to a type of solid-state material that includes amorphous as well as crystalline forms.

The term "crystalline form" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (melting point).

Processes

Provided herein are processes for preparing a compound of formula I or a pharmaceutically acceptable salt thereof.

The present processes may be performed using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula I, or other formulas or compounds disclosed herein (e.g. compounds 2a, 3a, 5a, 7a, 2-1, 5-1, 5-2, etc.), may be accomplished as described in the following examples. If available, reagents may be purchased commercially, e.g. from Sigma Aldrich or other chemical suppliers.

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^h$ Edition, 2001), and Larock's Comprehensive Organic Transformations (VCH Publishers Inc., 1989).

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller, C. H., (1975) *J. Chromatogr.,* 113, 3) 283-302). Racemic mixtures of chiral compounds of the disclosure can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched substrate. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (Chiral Liquid Chromatography (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Scheme 1a below shows an embodiment of the general method for the synthesis of a compound of formula I, or a pharmaceutically acceptable salt thereof, described herein. It is contemplated that the exemplary synthesis shown in the Schemes provided herein, such as Scheme 1a and 2, may be particularly advantageous. Such advantages may include, for example, high yields and purity.

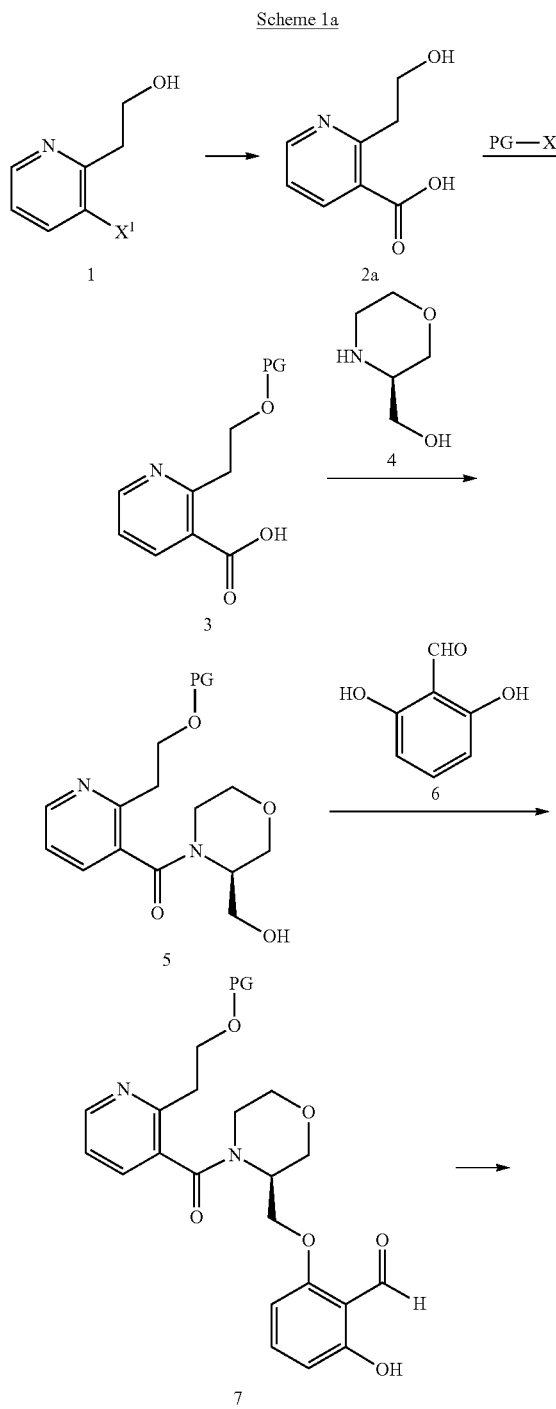

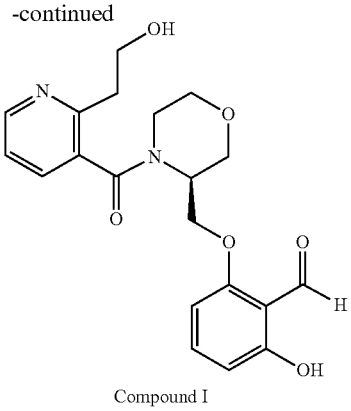

Compound I

In some embodiments, $X^1$ is halo; PG is a hydroxy protecting group; and $X^2$ is halo, hydrogen, hydroxyl, or —OC(O)CH₃.

In some embodiments, $X^1$ is chloro. In some embodiments, $X^1$ is bromo. In some embodiments, $X^1$ is iodo.

In some embodiments, PG-$X^2$ is tert-butyl(chloro)diphenylsilane. In some embodiments, PG-$X^2$ is tert-butyldimethylsilyl chloride. In some embodiments, PG-$X^2$ is acetic anhydride. In some embodiments, PG-$X^2$ is benzyl bromide. In some embodiments, PG-$X^2$ is benzoyl chloride. In some embodiments, PG-$X^2$ is dihydropyran.

In some embodiments, PG is tert-butyldimethylsilyl (TBS), tert-butyldiphenylsilyl (TBDPS), acetyl (Ac), benzoyl (Bz), tetrahydropyranyl (THP), or benzyl (Bn). In some embodiments, PG is tert-butyldiphenylsilyl (TBDPS). In some embodiments, PG is benzyl (Bn). In some embodiments, PG is benzoyl (Bz). In some embodiments, PG is acetyl (Ac).

In some embodiments, $X^2$ is chloro, bromo, hydrogen, hydroxyl, or —OC(O)CH₃. In some embodiments, $X^2$ is halo. In some embodiments, $X^2$ is chloro.

In some embodiments, compound of formula 3 also may be synthesized as shown in Scheme 1b (wherein variables $X^1$, PG, and $X^2$ are as described herein) from compound 1 by first protecting the hydroxyl group to form a compound of formula 2b, and subsequently introducing the carboxylic acid to form compound of formula 3. Such methods can be performed as described herein or according to methods known in the art.

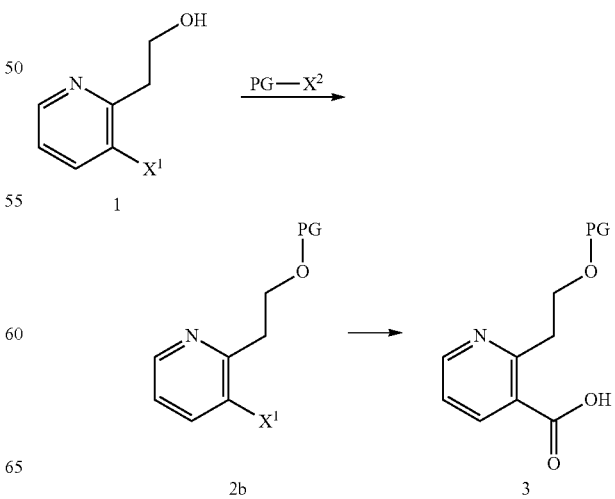

In some embodiments, compound of formula 3 also may be synthesized as shown in Scheme 1c (wherein variable PG is as described herein, $X^3$ is halo, and $R^4$ is $C_{1-3}$ alkyl) from compound of formula 16. In some embodiments, compound of formula 17 is achieved from a compound of formula 16 according to methods known in the art and as described herein. Compound of formula 2a, or a salt thereof, may be achieved from a compound of formula 17 in the presence of a reducing agent. In some embodiments, the reducing agent is sodium borohydride, triacetoxy borohydride, lithium triethylborohyride, or lithium borohyride. In some embodiments, the reducing agent is lithium borohyride. Isolation of a salt of compound of formula 2a or a freebase of compound of formula 2a can be achieved according to methods known in the art. Introduction of a protecting group to form compound of formula 3 from compound 2a, or a salt thereof, can be achieved according to methods known in the art and as described herein.

Scheme 1c

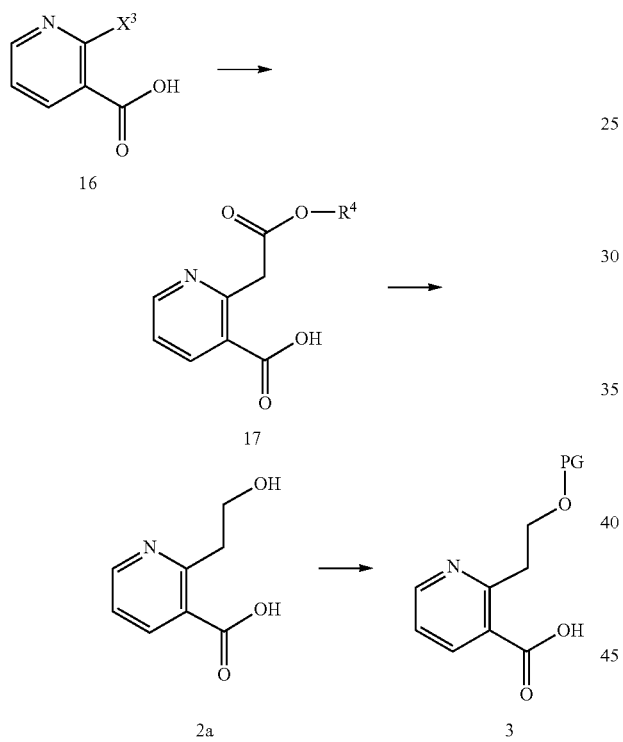

Some embodiments provide for a process for preparing a compound of formula I:

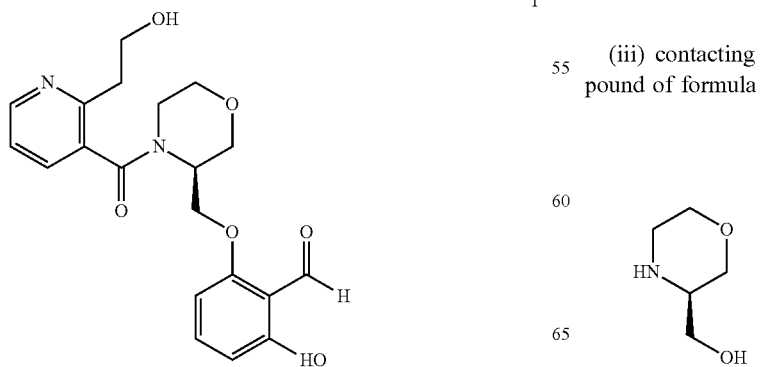

comprising:

(i) contacting a compound of formula 1:

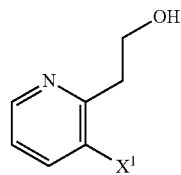

1 wherein $X^1$ is halo;

with a metalating reagent and carbon dioxide under conditions sufficient to form a compound of formula 2a:

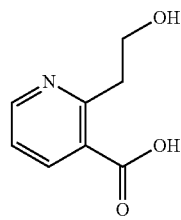

2a (ii) contacting a compound of formula 2a with a compound of formula:

PG-$X^2$ wherein PG is a hydroxy protecting group and $X^2$ is halo;
under conditions sufficient to form a compound of formula 3:

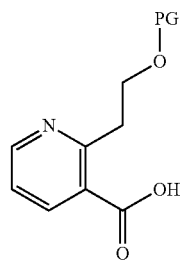

3

(iii) contacting a compound of formula 3 with a compound of formula 4:

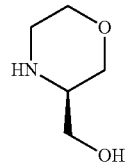

4 under conditions sufficient to form a compound of formula 5:

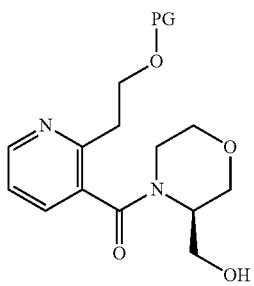

(iv) contacting a compound of formula 5 with a compound of formula 6:

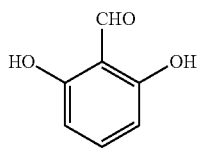

under conditions sufficient to form a compound of formula 7:

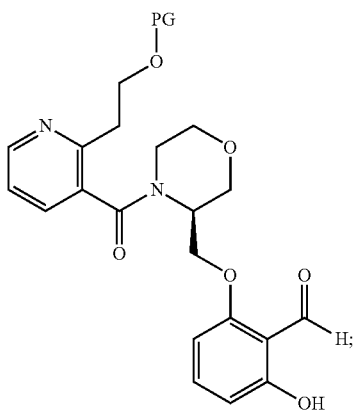

and (v) deprotecting a compound of formula 7 to form a compound of formula I.

In some embodiments, the reaction conditions of step (i) comprise a metalating reagent, wherein the metalating reagent is isopropyl magnesium chloride or isopropyl magnesium bromide. In some embodiments, the reaction conditions of step (i) comprise a metalating reagent, wherein the metalating reagent is isopropyl magnesium chloride. In some embodiments, the reaction conditions of step (i) comprise a solvent selected from 2-methyltetrahydrofuran and tetrahydrofuran. In some embodiments, the reaction conditions of step (i) comprise a solvent, wherein the solvent is tetrahydrofuran. In some embodiments, the reaction conditions of step (i) comprise a temperature of about −20° C. to about 20° C. In some embodiments, the reaction conditions of step (i) comprise a temperature of about −15° C. to about 15° C.

In some embodiments, the reaction conditions of step (ii) comprise a base and a solvent. Non-limiting examples of a base include imidazole, triethylamine, $K_2CO_3$, and the like. Non-limiting examples of a solvent include tetrahydrofuran, dimethylformamide, dichloromethane, methyl tetrahydrofuran, toluene, biphasic solvent systems, and the like.

In some embodiments, the reaction conditions of step (ii) comprise a hydroxy protecting group, wherein the hydroxy protecting group is tert-butyl(chloro)diphenylsilane. In some embodiments, the reaction conditions of step (ii) comprise a base selected from imidazole. In some embodiments, the reaction conditions of step (ii) comprise a solvent selected from tetrahydrofuran. In some embodiments, the reaction conditions of step (ii) comprise a temperature of about 10° C. to about 50° C. In some embodiments, the reaction conditions of step (ii) comprise a temperature of about 15° C. to 40° C.

In some embodiments, the reaction conditions of step (iii) comprise a coupling agent and base. In some embodiments, the coupling agent is N,N,N',N'-Tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxide hexafluorophosphate (HATU), 1,1'-carbonyldiimidazole (CDI), or propanephosphonic acid anhydride (T3P). In some embodiments, the base is triethylamine (TEA) or N,N-diisopropylethylamine (DIEA). In some embodiments, the base is DIEA.

In some embodiments, the coupling agent is N,N,N',N'-Tetramethyl-O-(1H-benzotriazol-1-yl)uronium hexafluorophosphate, and the base is diisopropylethylamine.

In some embodiments, the reaction conditions of step (iii) comprise a solvent selected from tetrahydrofuran (THF), dimethylformamide (DMF), methyl tert-butyl ether (MTBE), dichloromethane (DCM), 2-methyltetrahydrofuran (MeTHF), ethyl acetate (EtOAc), toluene (PhMe), dioxane, and acetonitrile (ACN). In some embodiments, the reaction conditions of step (iii) comprise a temperature of about −15° C. to 45° C. In some embodiments, the reaction conditions of step (iii) comprise a temperature of about −10° C. to 30° C.

In some embodiments, the reaction conditions of step (iv) provide compound of formula 7 or a salt thereof. In some embodiments, the salt of a compound of formula 7 is a sulfate salt of a compound of formula 7.

In some embodiments, the reaction conditions of step (iv) comprise an azodicarboxylate, wherein the azodicarboxylate is diisopropyl azodicarboxylate (DIAD). In some embodiments, the reaction conditions of step (iv) comprise a phosphine, wherein the phosphine is triphenylphosphine. In some embodiments, the reaction conditions of step (iv) comprise triphenylphosphine and diisopropyl azodicarboxylate.

In some embodiments, the reaction conditions of step (iv) comprise a solvent selected from dichloromethane (DCM), tetrahydrofuran (THF), 2-methyltetrahydrofuran, ethyl acetate (EtOAc), toluene (PhMe), and acetonitrile (ACN). In some embodiments, the reaction conditions of step (iv) comprise a temperature of about 25° C. to 40° C.

In some embodiments, the reaction conditions of step (v) comprise a deprotecting reagent selected from tetrabutylammonium fluoride (TBAF) and hydrochloric acid (HCl). In some embodiments, the reaction conditions of step (v) comprise a deprotecting reagent, wherein the deprotecting reagent is tetrabutylammonium fluoride (TBAF). In some embodiments, TBAF is added to a compound of formula 7 in situ. In some embodiments, the reaction conditions of step (v) comprise a deprotecting reagent, wherein the deprotecting reagent is hydrochloric acid (HCl). In some embodiments, HCl is added to a compound of formula 7 in situ.

In some embodiments, the reaction conditions of step (v) comprise a solvent selected from tetrahydrofuran (THF), 2-methyltetrahydrofuran, dichloromethane (DCM), methyl tert-butyl ether (MTBE), and ethyl acetate (EtOAc). In some embodiments, the reaction conditions of step (v) comprise a temperature of about 10° C. to 65° C. In some embodiments, the reaction conditions of step (v) comprise a temperature of about 15° C. to 50° C.

Some embodiments provide for a process for preparing a compound of formula I:

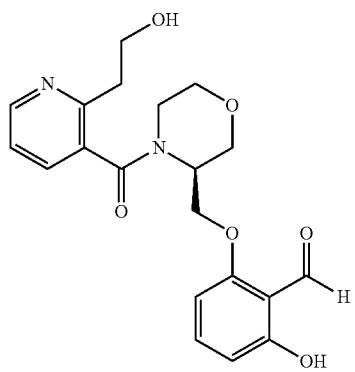

I comprising:

(i) contacting a compound of formula 1a:

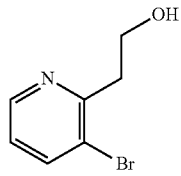

1a with a metalating reagent and carbon dioxide under conditions sufficient to form a compound of formula 2a:

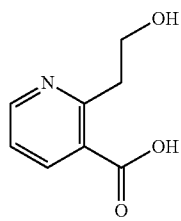

2a (ii) contacting a compound of formula 2a with tert-butyl (chloro)diphenylsilane and imidazole under conditions sufficient to form a compound of formula 3a:

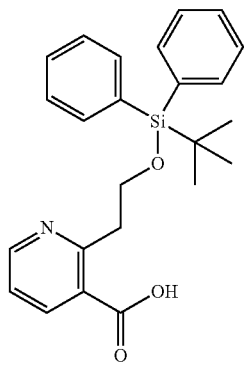

3a (iii) contacting a compound of formula 3a with a compound of formula 4

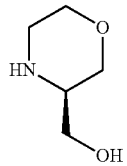

4 under conditions sufficient to form a compound of formula 5a:

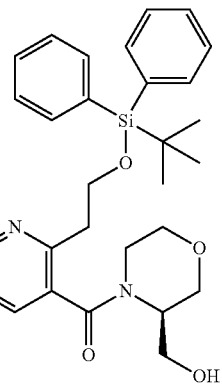

5a (iv) contacting a compound of formula 5a with a compound of formula 6:

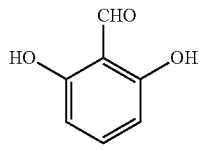

6 under conditions sufficient to form a compound of formula 7a:

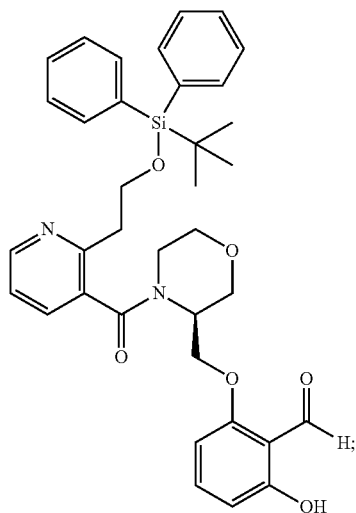

and (v) deprotecting a compound of formula 7a to form a compound of formula I.

In some embodiments, the reaction conditions of step (i) comprise a metalating reagent, wherein the metalating reagent is isopropyl magnesium chloride or isopropyl magnesium bromide. In some embodiments, the reaction conditions of step (i) comprise a metalating reagent, wherein the metalating reagent is isopropyl magnesium chloride. In some embodiments, the reaction conditions of step (i) comprise a solvent selected from 2-methyltetrahydrofuran and tetrahydrofuran. In some embodiments, the reaction conditions of step (i) comprise a solvent, wherein the solvent is tetrahydrofuran. In some embodiments, the reaction conditions of step (i) comprise a temperature of about –20° C. to about 20° C. In some embodiments, the reaction conditions of step (i) comprise a temperature of about –15° C. to about 15° C.

In some embodiments, the reaction conditions of step (ii) comprise a solvent selected from tetrahydrofuran. In some embodiments, the reaction conditions of step (ii) comprise a temperature of about 10° C. to about 50° C. In some embodiments, the reaction conditions of step (ii) comprise a temperature of about 15° C. to 40° C.

In some embodiments, the reaction conditions of step (iii) comprise a coupling agent and base. In some embodiments, the coupling agent is N,N,N',N'-Tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxide hexafluorophosphate (HATU), 1,1'-carbonyldiimidazole (CDI), or propanephosphonic acid anhydride (T3P). In some embodiments, the base is triethylamine (TEA) or N,N-diisopropylethylamine (DIEA).

In some embodiments, the coupling agent is N,N,N',N'-Tetramethyl-O-(1H-benzotriazol-1-yl)uronium hexafluorophosphate, and the base is diisopropylethylamine.

In some embodiments, the reaction conditions of step (iii) comprise a solvent selected from tetrahydrofuran (THF), dimethylformamide (DMF), methyl tert-butyl ether (MTBE), dichloromethane (DCM), 2-methyltetrahydrofuran (MeTHF), ethyl acetate (EtOAc), toluene (PhMe), dioxane, and acetonitrile (ACN). In some embodiments, the reaction conditions of step (iii) comprise a temperature of about –15° C. to 45° C. In some embodiments, the reaction conditions of step (iii) comprise a temperature of about –10° C. to 30° C.

In some embodiments, the reaction conditions of step (iv) comprise triphenylphosphine and diisopropyl azodicarboxylate. In some embodiments, the reaction conditions of step (iv) comprise a solvent selected from dichloromethane (DCM), tetrahydrofuran (THF), 2-methyltetrahydrofuran, ethyl acetate (EtOAc), toluene (PhMe), and acetonitrile (ACN). In some embodiments, the reaction conditions of step (iv) comprise a temperature of about 25° C. to 40° C.

In some embodiments, the reaction conditions of step (v) comprise a deprotecting reagent selected from tetrabutylammonium fluoride (TBAF) and hydrochloric acid (HCl). In some embodiments, the reaction conditions of step (v) comprise a deprotecting reagent, wherein the deprotecting reagent is tetrabutylammonium fluoride (TBAF). In some embodiments, TBAF is added to a compound of formula 7a in situ. In some embodiments, the reaction conditions of step (v) comprise a deprotecting reagent, wherein the deprotecting reagent is hydrochloric acid (HCl). In some embodiments, HCl is added to a compound of formula 7a in situ. In some embodiments, the reaction conditions of step (v) comprise a solvent selected from tetrahydrofuran (THF), 2-methyltetrahydrofuran, dichloromethane (DCM), methyl tert-butyl ether (MTBE), and ethyl acetate (EtOAc). In some embodiments, the reaction conditions of step (v) comprise a temperature of about 10° C. to 65° C. In some embodiments, the reaction conditions of step (v) comprise a temperature of about 15° C. to 50° C.

Some embodiments of the methods described herein further comprise crystallizing a compound of formula I to form a crystalline form characterized by an X-ray powder diffractogram comprising the following peaks: 18.3, 23.4, and 26.1°2θ±0.2°2θ (Compound I Form I), as determined on a diffractometer using Cu-Kα radiation. In some embodiments, the diffractogram further comprises one or more peaks at: 10.8 or 17.3°2θ±0.2°2θ.

In some embodiments, crystallizing a compound of formula I comprises a solvent selected from ethyl acetate (EtOAc), isopropyl alcohol (IPA), acetone, isopropyl acetate (iPrOAC), and methyl tert-butyl ether (MTBE). In some embodiments, crystallizing a compound of formula I comprises a first temperature of about 45° C. to 75° C. In some embodiments, crystallizing a compound of formula I comprises a second temperature of about 10° C. to 30° C. In some embodiments, crystallizing a compound of formula I comprise seeding with Compound I Form I. Such seeds may be made according to methods described herein.

Some embodiments provide for a process for preparing a compound of formula I:

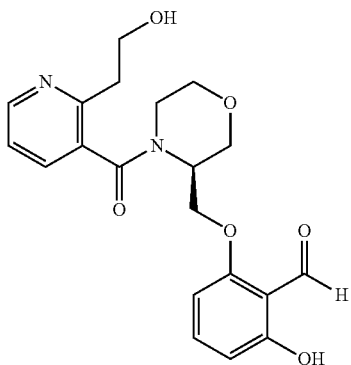

comprising:
(i) contacting a compound of formula 5a:

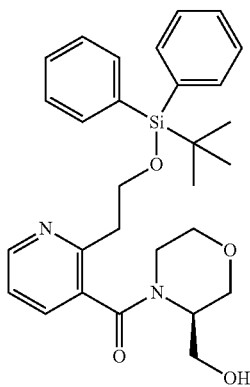

with a compound of formula 6:

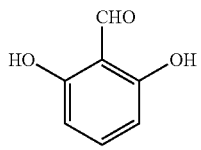

under conditions sufficient to form a compound of formula 7a:

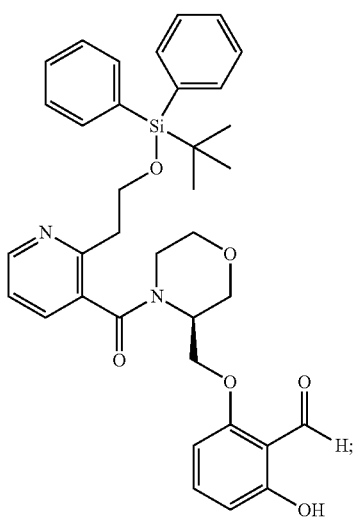

(ii) deprotecting a compound of formula 7a in situ with TBAF to form a compound of formula I; and (iii) crystallizing a compound of formula I to form a crystalline form characterized by an X-ray powder diffractogram comprising the following peaks: 18.3, 23.4, and 26.1°2θ±0.2° 2θ (Compound I Form I), as determined on a diffractometer using Cu-Kα radiation.

In some embodiments, the diffractogram further comprises one or more peaks at: 10.8 or 17.3°2θ±0.2°2θ.

In some embodiments, the reaction conditions of step (i) comprise triphenylphosphine and diisopropyl azodicarboxylate. In some embodiments, the reaction conditions of step (i) comprise a solvent selected from dichloromethane (DCM), tetrahydrofuran (THF), 2-methyltetrahydrofuran, ethyl acetate (EtOAc), toluene (PhMe), and acetonitrile (ACN). In some embodiments, the reaction conditions of step (i) comprise a temperature of about 25° C. to 40° C.

In some embodiments, the reaction conditions of step (ii) comprise a deprotecting reagent selected from tetrabutylammonium fluoride (TBAF) and hydrochoric acid (HCl). In some embodiments, the reaction conditions of step (ii) comprise a deprotecting reagent, wherein the deprotecting reagent is tetrabutylammonium fluoride (TBAF). In some embodiments, a compound of formula 7a is deprotected in situ with TBAF to form a compound of formula I. In some embodiments, the reaction conditions of step (ii) comprise a deprotecting reagent, wherein the deprotecting reagent is hydrochloric acid (HCl). In some embodiments, a compound of formula 7a is deprotected in situ with HCl to form a compound of formula I. In some embodiments, the reaction conditions of step (ii) comprise a solvent selected from tetrahydrofuran (THF), 2-methyltetrahydrofuran, dichloromethane (DCM), methyl tert-butyl ether (MTBE), and ethyl acetate (EtOAc). In some embodiments, the reaction conditions of step (ii) comprise a temperature of about 10° C. to 65° C. In some embodiments, the reaction conditions of step (ii) comprise a temperature of about 15° C. to 50° C.

In some embodiments, the reaction conditions for step (iii) comprise a solvent selected from ethyl acetate (EtOAc), isopropyl alcohol (IPA), acetone, isopropyl acetate (iPrOAc), and methyl tert-butyl ether (MTBE). In some embodiments, the reaction conditions for step (iii) comprise a first temperature of about 45° C. to 75° C. In some embodiments, the reaction conditions for step (iii) comprise a second temperature of about 10° C. to 30° C. In some embodiments, the reaction conditions for step (iii) comprise seeding with Compound I Form I.

Some embodiments provide for a process for preparing a compound of formula I:

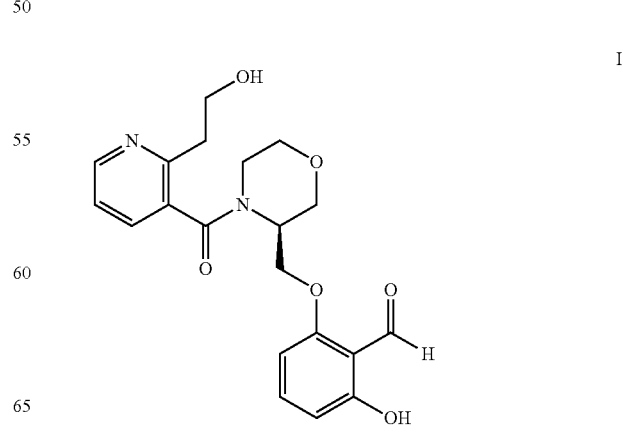

comprising:
(i) contacting a compound of formula 1a:

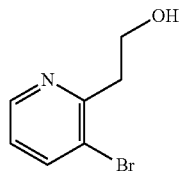

1a with a metalating reagent and carbon dioxide under conditions sufficient to form a compound of formula 2a:

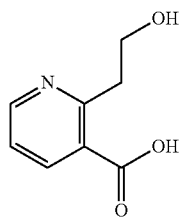

2a (ii) contacting a compound of formula 2a with tert-butyl(chloro)diphenylsilane and imidazole under conditions sufficient to form a compound of formula 3a:

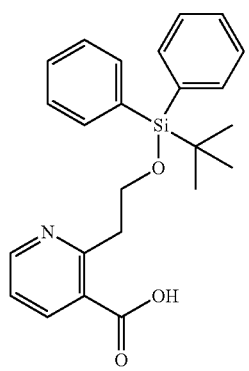

3a (iii) contacting a compound of formula 3a with a compound of formula 4

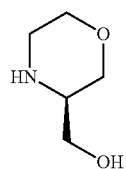

4 under conditions sufficient to form a compound of formula 5a:

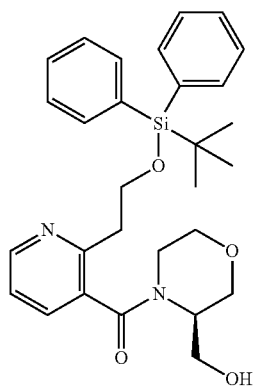

5a (iv) contacting a compound of formula 5a with a compound of formula 6:

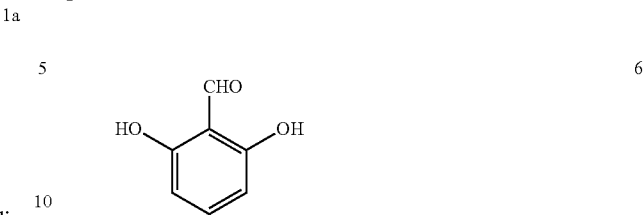

6 under conditions sufficient to form a compound of formula 7a:

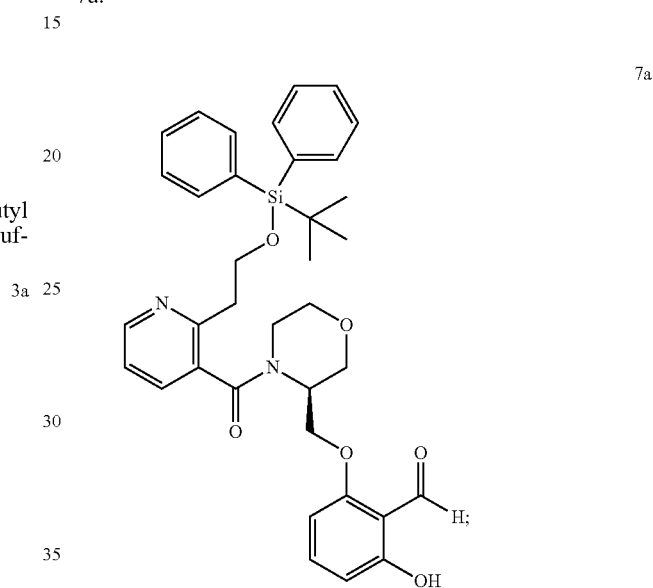

7a (v) deprotecting a compound of formula 7a in situ with TBAF to form a compound of formula I; and (vi) crystallizing a compound of formula I to form a crystalline form characterized by an X-ray powder diffractogram comprising the following peaks: 18.3, 23.4, and 26.1°2θ±0.2° 2θ (Compound I Form I), as determined on a diffractometer using Cu-Kα radiation.

In some embodiments, the reaction conditions of step (i) comprise a metalating reagent, wherein the metalating reagent is isopropyl magnesium chloride or isopropyl magnesium bromide. In some embodiments, the reaction conditions of step (i) comprise a metalating reagent, wherein the metalating reagent is isopropyl magnesium chloride. In some embodiments, the reaction conditions of step (i) comprise a solvent selected from 2-methyltetrahydrofuran and tetrahydrofuran. In some embodiments, the reaction conditions of step (i) comprise a solvent, wherein the solvent is tetrahydrofuran. In some embodiments, the reaction conditions of step (i) comprise a temperature of about −20° C. to about 20° C. In some embodiments, the reaction conditions of step (i) comprise a temperature of about −15° C. to about 15° C.

In some embodiments, the reaction conditions of step (ii) comprise a solvent selected from tetrahydrofuran. In some embodiments, the reaction conditions of step (ii) comprise a temperature of about 10° C. to about 50° C. In some embodiments, the reaction conditions of step (ii) comprise a temperature of about 15° C. to about 40° C.

In some embodiments, the reaction conditions of step (iii) comprise a coupling agent and base. In some embodiments, the coupling agent is N,N,N',N'-Tetramethyl-O-(1H-benzotriazol-1-yl)uronium hexafluorophosphate (HBTU), 1-[bis (dimethylamino)methylene]-1H-1,2,3-triazolo[4,5-b]pyridinium 3-oxide hexafluorophosphate (HATU), 1,1'-carbonyldiimidazole (CDI), or propanephosphonic acid anhydride (T3P). In some embodiments, the base is triethylamine (TEA) or N,N-diisopropylethylamine (DIEA).

In some embodiments, the coupling agent is N,N,N',N'-Tetramethyl-O-(1H-benzotriazol-1-yl)uronium hexafluorophosphate, and the base is diisopropylethylamine.

In some embodiments, the reaction conditions of step (iii) comprise a solvent selected from tetrahydrofuran (THF), dimethylformamide (DMF), methyl tert-butyl ether (MTBE), dichloromethane (DCM), 2-methyltetrahydrofuran (MeTHF), ethyl acetate (EtOAc), toluene (PhMe), dioxane, and acetonitrile (ACN). In some embodiments, the reaction conditions of step (iii) comprise a temperature of about −15° C. to 45° C. In some embodiments, the reaction conditions of step (iii) comprise a temperature of about −10° C. to 30° C.

In some embodiments, the reaction conditions of step (iv) comprise triphenylphosphine and diisopropyl azodicarboxylate. In some embodiments, the reaction conditions of step (iv) comprise a solvent selected from dichloromethane (DCM), tetrahydrofuran (THF), 2-methyltetrahydrofuran, ethyl acetate (EtOAc), toluene (PhMe), and acetonitrile (ACN). In some embodiments, the reaction conditions of step (iv) comprise a temperature of about 25° C. to 40° C.

In some embodiments, the reaction conditions of step (v) comprise a deprotecting reagent selected from tetrabutylammonium fluoride (TBAF) and hydrochloric acid. In some embodiments, the reaction conditions of step (v) comprise a deprotecting reagent, wherein the deprotecting reagent is tetrabutylammonium fluoride (TBAF). In some embodiments, a compound of formula 7a is deprotected in situ with TBAF to form a compound of formula I. In some embodiments, the reaction conditions of step (v) comprise a deprotecting reagent, wherein the deprotecting reagent is hydrochloric acid (HCl). In some embodiments, a compound of formula 7a is deprotected in situ with HCl to form a compound of formula I. In some embodiments, the reaction conditions of step (v) comprise a solvent selected from tetrahydrofuran (THF), 2-methyltetrahydrofuran, dichloromethane (DCM), methyl tert-butyl ether (MTBE), and ethyl acetate (EtOAc). In some embodiments, the reaction conditions of step (v) comprise a temperature of about 10° C. to 65° C. In some embodiments, the reaction conditions of step (v) comprise a temperature of about 15° C. to 50° C.

In some embodiments, the reaction conditions for step (vi) comprise a solvent selected from ethyl acetate (EtOAc), isopropyl alcohol (IPA), acetone, isopropyl acetate (iPrOAC), and methyl tert-butyl ether (MTBE). In some embodiments, the reaction conditions for step (vi) comprise a first temperature of about 45° C. to 75° C. In some embodiments, the reaction conditions for step (vi) comprise a second temperature of about 10° C. to 30° C. In some embodiments, the reaction conditions for step (vi) comprise seeding with Compound I Form I.

Some embodiments described herein further comprise crystallizing a compound of formula I to form a crystalline form characterized by an X-ray powder diffractogram comprising the following peaks: 18.3, 23.4, and 26.1°2θ±0.2° 2θ (Compound I Form I), as determined on a diffractometer using Cu-Kα radiation. In some embodiments, the diffractogram further comprises one or more peaks at: 10.8 or 17.3°2θ±0.2°2θ.

Some embodiments provide for a process for preparing a compound of formula I:

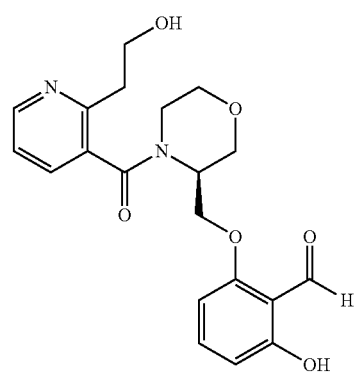

I comprising:
(i) contacting a compound of formula 3d:

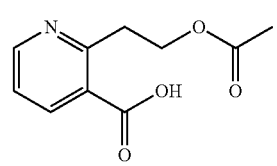

3d with a compound of formula 4:

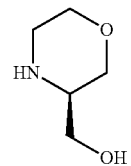

4 under conditions sufficient to form a compound of formula 5d:

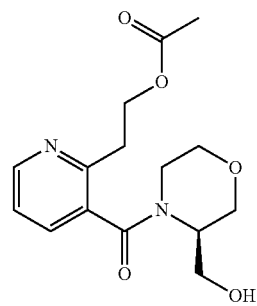

5d (ii) contacting a compound of formula 5d with a compound of formula 6:

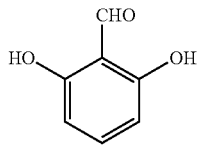

under conditions sufficient to form a compound of formula 7d:

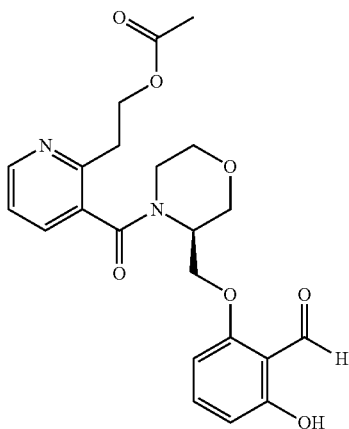

(iii) deprotecting a compound of formula 7d under conditions sufficient to form a compound of formula I; and (iv) crystallizing a compound of formula I to form a crystalline form characterized by an X-ray powder diffractogram comprising the following peaks: 18.3, 23.4, and 26.1°2θ±0.2° 2θ (Compound I Form I), as determined on a diffractometer using Cu-Kα radiation.

In some embodiments, the reaction conditions of step (i) comprise a coupling agent and base. In some embodiments, the coupling agent is N,N,N',N'-Tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxide hexafluorophosphate (HATU), 1,1'-carbonyldiimidazole (CDI), or propanephosphonic acid anhydride (T3P). In some embodiments, the base is triethylamine (TEA) or N,N-diisopropylethylamine (DIEA).

In some embodiments, the coupling agent is N,N,N',N'-Tetramethyl-O-(1H-benzotriazol-1-yl)uronium hexafluorophosphate, and the base is diisopropylethylamine.

In some embodiments, the reaction conditions of step (i) comprise a solvent selected from tetrahydrofuran (THF), dimethylformamide (DMF), methyl tert-butyl ether (MTBE), dichloromethane (DCM), 2-methyltetrahydrofuran (MeTHF), ethyl acetate (EtOAc), toluene (PhMe), dioxane, and acetonitrile (ACN). In some embodiments, the reaction conditions of step (i) comprise a temperature of about −15° C. to 45° C. In some embodiments, the reaction conditions of step (i) comprise a temperature of about −10° C. to 30° C.

In some embodiments, the reaction conditions of step (ii) comprise triphenylphosphine and diisopropyl azodicarboxylate. In some embodiments, the reaction conditions of step (iv) comprise a solvent selected from dichloromethane (DCM), tetrahydrofuran (THF), 2-methyltetrahydrofuran, ethyl acetate (EtOAc), toluene (PhMe), and acetonitrile (ACN). In some embodiments, the reaction conditions of step (iv) comprise a temperature of about 25° C. to 40° C.

some embodiments, the reaction conditions of step (vii) comprise a deprotecting reagent In some embodiments, the reaction conditions of step (iii) comprise an acid or base. In some embodiments, the base is LiOH.

In some embodiments, the reaction conditions for step (iv) comprise a solvent selected from ethyl acetate (EtOAc), isopropyl alcohol (IPA), acetone, isopropyl acetate (iPrOAC), and methyl tert-butyl ether (MTBE). In some embodiments, the reaction conditions for step (iv) comprise a first temperature of about 45° C. to 75° C. In some embodiments, the reaction conditions for step (iv) comprise a second temperature of about 10° C. to 30° C. In some embodiments, the reaction conditions for step (iv) comprise seeding with Compound I Form I.

In some embodiments, compound of formula 3d may be made as described herein.

In some embodiments, compound of formula 3d may be achieved via deprotecting compound of formula 3a (for example, in the presence of triethylamine trihydrofluoride) to form compound of formula 2a, and contacting compound of formula 2a with acetic anhydride (for example, in the presence of DMAP and diisopropylethylamine) to form compound of formula 3d.

In some embodiments, compound of formula 3d may be achieved by hydrolyzing compound of formula 9 of Scheme 2 below to form compound of formula 2a, and contacting compound of formula 2a with acetic anhydride (for example, in the presence of DMAP and diisopropylethylamine) to form compound of formula 3d. Compound of formula 9 may be synthesized from compound of formula 1a in the presence of CO and a palladium catalyst.

Scheme 2 below shows a further embodiment of the general method for the synthesis of a compound of formula I described herein.

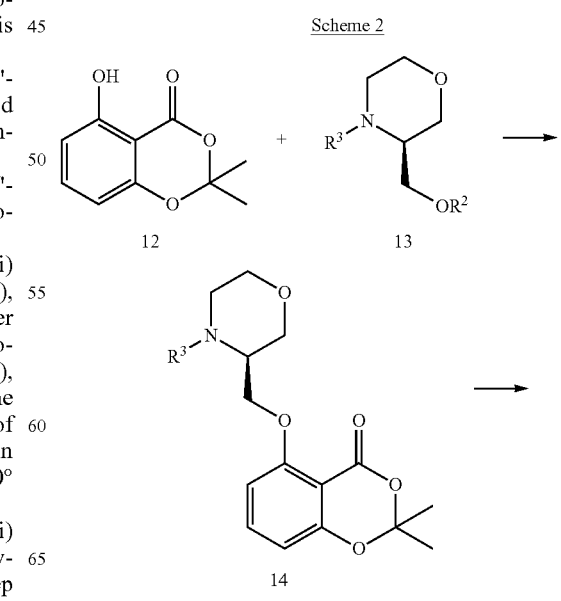

Scheme 2

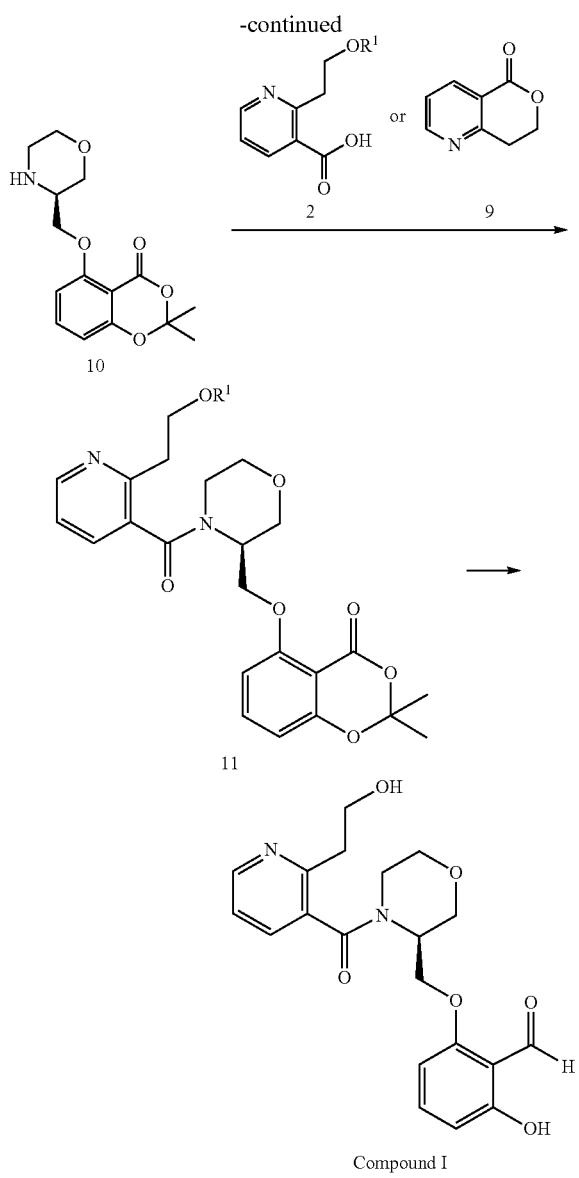

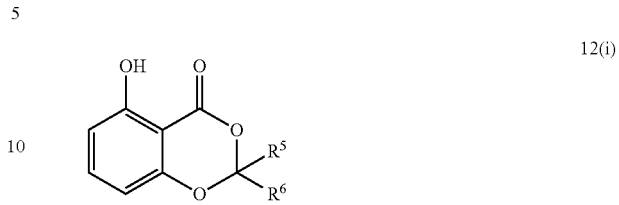

In some embodiments, R¹ is H or a hydroxy protecting group; R² is H or leaving group; and R³ is H or an amine protecting group.

In some embodiments, R¹ is H or a hydroxy protecting group; R² is H or leaving group; and R³ is H; or R² and R³, together with the atoms to which they are attached, join together to form a heterocyclic ring.

In some embodiments, R¹ is hydrogen, tert-butyldimethylsilyl (TBS), tert-butyldiphenylsilyl (TBDPS), acetyl (Ac), benzoyl (Bz), tetrahydropyranyl (THP), or benzyl (Bn). In some embodiments, R¹ is hydrogen. In some embodiments, R¹ is tert-butyldiphenylsilyl (TBDPS). In some embodiments, R¹ is acetyl (Ac).

In some embodiments, R² is H, tosyl (Ts), or mesyl (Ms). In some embodiments, R² is H. In some embodiments, R² is tosyl (Ts). In some embodiments, R² is mesyl (Ms). In some embodiments, R² is H or tosyl.

In some embodiments, R³ is H, —C(O)—O—C(CH₃)₃, or —C(O)—O—CH₂-phenyl. In some embodiments, R³ is H. In some embodiments, R³ is —C(O)—O—C(CH₃)₃.

In some embodiments, compound of formula 12(i) may be used as a starting material instead of compound 12, wherein compound of formula 12(i):

12(i)

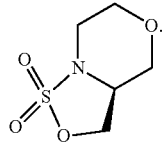

wherein R⁵ and R⁶ are each independently selected from $C_{1-6}$ alkyl or R⁵ and R⁶, together with the carbon to which they are attached, join together to form a 3, 4, 5, or 6-membered cycloalkyl or heterocycloalkyl ring.

In some embodiments, R⁵ and R⁶ are each independently selected from $C_{1-6}$ alkyl. In some embodiments, R⁵ and R⁶, together with the carbon to which they are attached, join together to form a 3, 4, 5, or 6-membered cycloalkyl or heterocycloalkyl ring.

In some embodiments, the compound of formula 13 is a compound of formula 13a:

13a

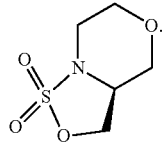

In some embodiments, the compound of formula 13 is a compound of formula 13g:

13g

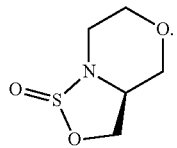

In some embodiments, provided herein is a process for preparing a compound of formula I:

I

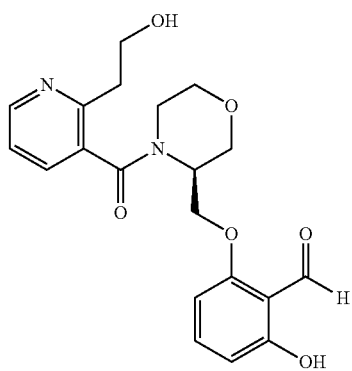

comprising:

(i) contacting a compound of formula 2 or a compound of formula 9:

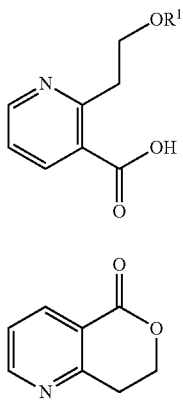

wherein R¹ is H or a hydroxy protecting group;
with a compound of formula 10:

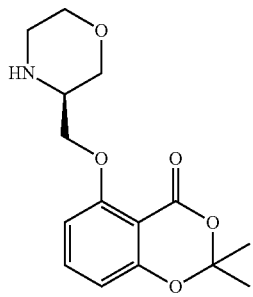

under conditions sufficient to form a compound of formula 11:

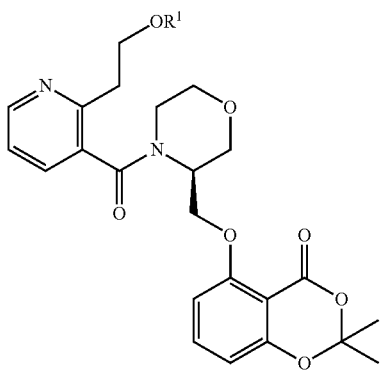

(ii) reducing and deprotecting a compound of formula 11 under conditions sufficient to provide a compound of formula I.

In some embodiments, the reaction conditions of step (i) comprise contacting a compound of formula 9 with a compound of formula 10 under conditions sufficient to form a compound of formula 11; and (ii) reducing a compound of formula 11 under conditions sufficient to provide a compound of formula I.

In some embodiments, the reaction conditions of step (i) comprise contacting a compound of formula 2 with a compound of formula 10 under conditions sufficient to form a compound of formula 11; and (ii) reducing and deprotecting a compound of formula 11 under conditions sufficient to provide a compound of formula I.

In some embodiments, the reaction conditions of step (i) comprise a metalating reagent, wherein the metalating reagent is isopropyl magnesium chloride or isopropyl magnesium bromide. In some embodiments, the reaction conditions of step (i) comprise a metalating reagent, wherein the metalating reagent is isopropyl magnesium chloride. In some embodiments, the reaction conditions of step (i) comprise a solvent selected from 2-methyltetrahydrofuran and tetrahydrofuran. In some embodiments, the reaction conditions of step (i) comprise a solvent, wherein the solvent is tetrahydrofuran. In some embodiments, the reaction conditions of step (i) comprise a temperature of about −20° C. to about 20° C. In some embodiments, the reaction conditions of step (i) comprise a temperature of about −15° C. to about 15° C.

In some embodiments, the reaction conditions of step (ii) comprise first a reducing agent, wherein the reducing agent is diisobutylaluminium hydride (DIBAL-H). In some embodiments, the reaction conditions of step (ii) comprise a solvent selected from dichloromethane (DCM) and ethyl acetate (EtOAc). In some embodiments, the reaction conditions of step (ii) comprise a temperature of about −80° C. to 30° C. In some embodiments, the reaction conditions of step (ii) comprise a temperature of about −78° C. to 25° C.

In some embodiments, the reaction conditions of step (ii) further comprise a deprotecting reagent selected from tetrabutylammonium fluoride (TBAF) and hydrochloric acid (HCl). In some embodiments, the reaction conditions of step (ii) comprise a deprotecting reagent, wherein the deprotecting reagent is tetrabutylammonium fluoride (TBAF). In some embodiments, a compound of formula 11 is deprotected in situ with TBAF to form a compound of formula I. In some embodiments, the reaction conditions of step (ii) comprise a deprotecting reagent, wherein the deprotecting reagent is hydrochloric acid (HCl). In some embodiments, a compound of formula 11 is deprotected in situ with HCl to form a compound of formula I. In some embodiments, the reaction conditions of step (ii) further comprise a solvent selected from tetrahydrofuran (THF), 2-methyltetrahydrofuran, dichloromethane (DCM), methyl tert-butyl ether (MTBE), and ethyl acetate (EtOAc). In some embodiments, the reaction conditions of step (ii) further comprise a temperature of about 10° C. to 65° C. In some embodiments, the reaction conditions of step (ii) further comprise a temperature of about 15° C. to 50° C.

In some embodiments, provided herein is a process for preparing a compound of formula I:

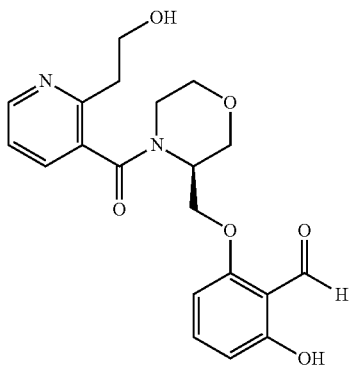

comprising:

(i) contacting a compound of formula 2:

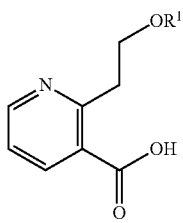

wherein R¹ is hydroxy protecting group;
with a compound of formula 10:

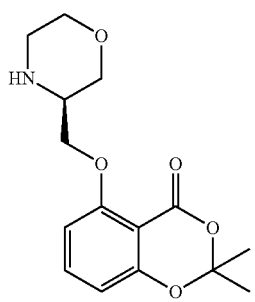

or a salt thereof,
under conditions sufficient to form a compound of formula 11:

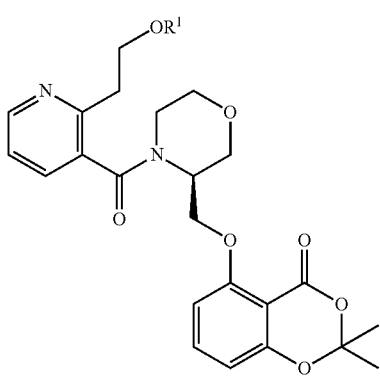

(ii) contacting a compound of formula 11 with a reductant under conditions sufficient to form a compound of formula 15:

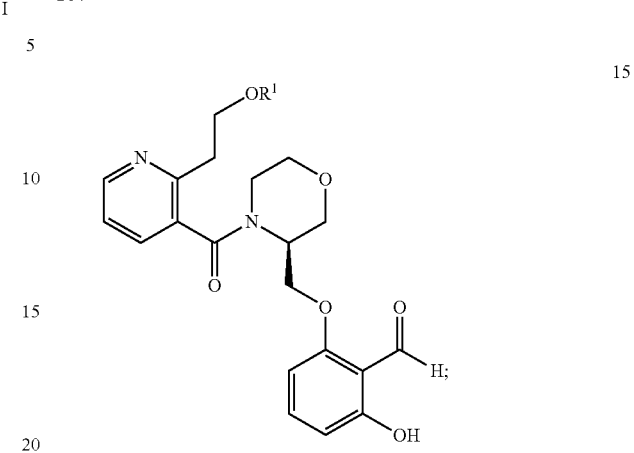

and (iii) deprotecting a compound of formula 15 to form a compound of formula I.

In some embodiments, the hydroxy protecting group is tert-butyldimethylsilyl (TBS), tert-butyldiphenylsilyl (TBDPS), acetyl (Ac), benzoyl (Bz), tetrahydropyranyl (THP), or benzyl (Bn). In some embodiments, the hydroxy protecting group is tert-butyldiphenylsilyl (TBDPS), acetyl (Ac), or benzoyl (Bz). In some embodiments, the hydroxy protecting group is tert-butyldiphenylsilyl (TBDPS). In some embodiments, the hydroxy protecting group is acetyl (Ac). In some embodiments, the hydroxy protecting group is benzoyl (Bz).

In some embodiments, a salt of a compound of formula 10 is a mesylate salt of compound of formula 10. In some embodiments, a salt of a compound of formula 10 is an HCl salt of compound of formula 10.

In some embodiments, the reaction conditions of step (i) comprises a coupling agent and a base. In some embodiments, the coupling agent is N,N,N',N'-tetramethyl-O-(1H-benzotriazol-1-yl)uronium hexafluorophosphate (HBTU) or propylphosphonic anhydride. In some embodiments, the coupling agent is propylphosphonic anhydride. In some embodiments, the base is triethylamine or diisopropylethylamine. In some embodiments, the reaction conditions of step (ii) comprise a temperature of about −5° C. to room temperature.

In some embodiments, the reductant is DIBAL-H, lithium diisobutyl-t-butoxyaluminum hydride (LDBBA), lithium aluminum-tri-tert-butoxyhydride (LTBA), DIBAL-H and n-butyllithium, sodium bis(2-methoxyethoxy)aluminum dihydride (Red-Al) with cis-2,6-dimethylmorpholine, Red-Al with ethanol, KBH₄, or poly(methylhydrosiloxane) and TiCp₂F₂. In some embodiments, the reductant is LDBBA.

In some embodiments, the reaction conditions of step (ii) comprise a temperature of about −80° C. to 30° C. In some embodiments, the reaction conditions of step (ii) comprise a temperature of about −70° C. to 30° C. In some embodiments, the reaction conditions of step (ii) comprise a temperature of about −55° C. to 25° C. In some embodiments, the reaction conditions of step (ii) further comprise a solvent selected from cyclopentyl methyl ether (CPME), tetrahydrofuran (THF), and 2-methyltetrahydrofuran.

In some embodiments, the reaction conditions of step (iii) further comprise a deprotecting reagent.

In some embodiments, the reaction conditions of step (iii) further comprise a deprotecting reagent selected from tetrabutylammonium fluoride (TBAF) and hydrochloric acid (HCl). In some embodiments, the reaction conditions of step (iii) comprise a deprotecting reagent, wherein the deprotecting reagent is tetrabutylammonium fluoride (TBAF). In some embodiments, the reaction conditions of step (iii) further comprise a solvent selected from tetrahydrofuran (THF), 2-methyltetrahydrofuran, dichloromethane (DCM), methyl tert-butyl ether (MTBE), and ethyl acetate (EtOAc). In some embodiments, the reaction conditions of step (iii) further comprise a temperature of about 10° C. to 65° C. In some embodiments, the reaction conditions of step (ii) further comprise a temperature of about 15° C. to 45° C.

In some embodiments, provided herein is a process for preparing a compound of formula I:

I

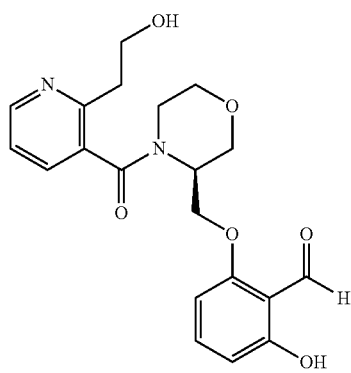

comprising:

(i) contacting a compound of formula 2:

2

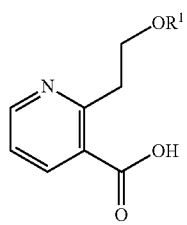

wherein $R^1$ is hydroxy protecting group;

with a compound of formula 10:

10

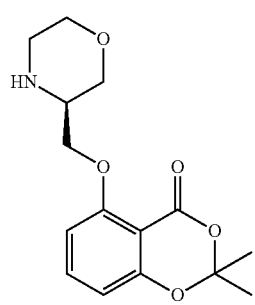

or a salt thereof, under conditions sufficient to form a compound of formula 11:

11

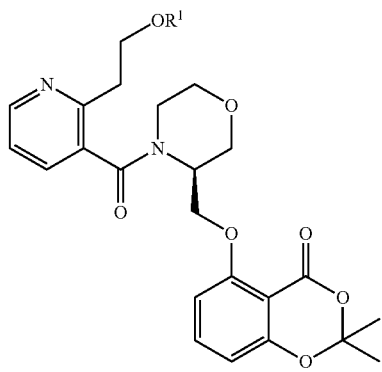

(ii) contacting a compound of formula 11 with a reductant under conditions sufficient to form a compound of formula 18:

18

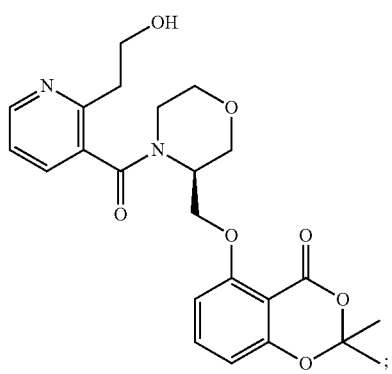

and (iii) contacting a compound of formula 18 with a reductant under conditions sufficient to form a compound of formula I.

In such embodiments, reaction conditions for step (i) and (ii) may be as described herein. In some embodiments, the reductant is DIBAL-H, lithium diisobutyl-t-butoxyaluminum hydride (LDBBA), lithium aluminum-tri-tert-butoxyhydride (LTBA), DIBAL-H and n-butyllithium, sodium bis(2-methoxyethoxy)aluminum dihydride (Red-Al) with cis-2,6-dimethylmorpholine, Red-Al with ethanol, $KBH_4$, or poly(methylhydrosiloxane) and $TiCp_2F_2$. In some embodiments, the reductant is LDBBA.

In some embodiments, provided herein is a process for preparing a compound of formula I:

I

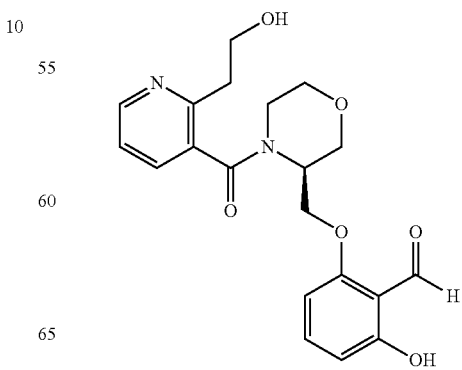

comprising:
(i) contacting a compound of formula 2:

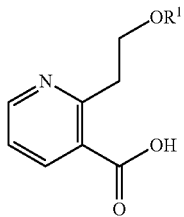

wherein $R^1$ is hydroxy protecting group;
with a compound of formula 10:

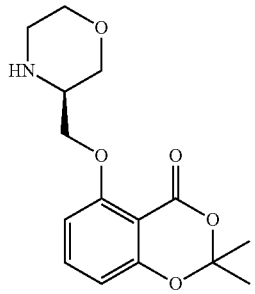

or a salt thereof,
under conditions sufficient to form a compound of formula 11:

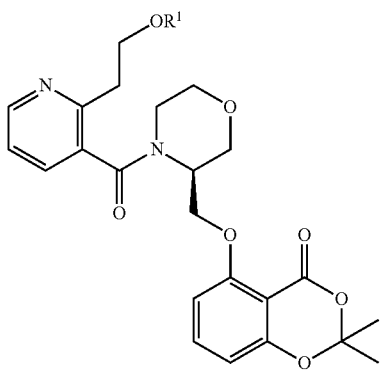

(ii) contacting a compound of formula 11 with lithium diisobutyl-t-butoxyaluminum hydride (LDBBA) under conditions sufficient to provide a compound of formula I.

In some embodiments, the hydroxy protecting group is tert-butyldimethylsilyl (TBS), tert-butyldiphenylsilyl (TBDPS), acetyl (Ac), benzoyl (Bz), tetrahydropyranyl (THP), or benzyl (Bn). In some embodiments, the hydroxy protecting group is tert-butyldiphenylsilyl (TBDPS), acetyl (Ac), or benzoyl (Bz). In some embodiments, the hydroxy protecting group is acetyl (Ac). In some embodiments, the hydroxy protecting group is benzoyl (Bz).

In some embodiments, a salt of a compound of formula 10 is a mesylate salt of compound of formula 10. In some embodiments, a salt of a compound of formula 10 is an HCl salt of compound of formula 10.

In some embodiments, the reaction conditions of step (i) comprises a coupling agent and a base. In some embodiments, the coupling agent is N,N,N',N'-tetramethyl-O-(1H-benzotriazol-1-yl)uronium hexafluorophosphate (HBTU) or propylphosphonic anhydride. In some embodiments, the coupling agent is propylphosphonic anhydride. In some embodiments, the base is triethylamine or diisopropylethylamine. In some embodiments, the reaction conditions of step (ii) comprise a temperature of about −5° C. to room temperature.

In some embodiments, the reaction conditions of step (ii) further comprise a solvent selected from tetrahydrofuran (THF), 2-methyltetrahydrofuran, and cyclopentyl methyl ether (CPME), In some embodiments described herein, compounds of formula 2, wherein $R^1$ is a hydroxy protecting group, can be synthesized according to Scheme 1c.

Some embodiments for preparing a compound of formula I as described herein further comprise:
(i) contacting a compound of formula 17:

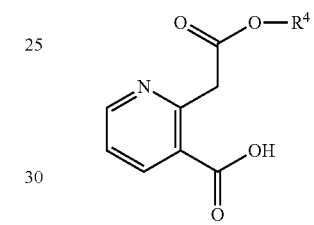

wherein $R^4$ is $C_{1-3}$ alkyl;
with a reducing agent under conditions sufficient to form compound of formula 2a:

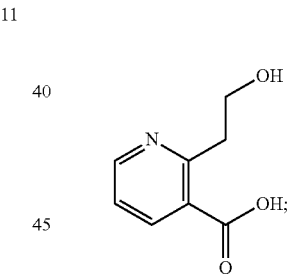

or a salt thereof; and
(ii) contacting compound of formula 2a with $R^1$—$X^2$ under conditions sufficient to form compound of formula 2 wherein $R^1$ is hydroxy protecting group.

In some embodiments, $R^4$ is methyl. In some embodiments, $R^4$ is ethyl.

In some embodiments, $R^1$—$X^2$ is tert-butyl(chloro)diphenylsilane. In some embodiments, $R^1$—$X^2$ is tert-butyldimethylsilyl chloride. In some embodiments, $R^1$—$X^2$ is acetic anhydride. In some embodiments, $R^1$—$X^2$ is benzyl bromide. In some embodiments, $R^1$—$X^2$ is benzoyl chloride. In some embodiments, $R^1$—$X^2$ is dihydropyran.

In some embodiments, the reducing agent is sodium borohydride, triacetoxy borohydride, lithium triethylborohydride, or lithium borohyride. In some embodiments, the reducing agent is lithium borohyride.

In some embodiments, the reaction conditions of step (i) (for forming compound 2a) comprise a solvent, wherein the solvent is isopropanol, 1-propanol, 1-butanol, 2-butanol, tert-butanol, methanol, ethanol, or a mixture thereof. In some embodiments, the reaction conditions of step (i) comprise a temperature of about 5° C. to 35° C. In some embodiments, the reaction conditions of step (i) comprise a temperature of about 10° C. to 30° C.

In some embodiments, a salt of compound of formula 2a is an HCl salt of a compound of formula 2a.

In some embodiments, a compound of formula 17 can be made from 2-bromonicotinic acid or 2-chloronicotinic acid according to methods known in the art.

In some embodiments, a compound of formula 17 can be made by alkylating 2-methylnicotinic acid, which can be made according to methods known in the art. For example, wherein $R^4$ is methyl or ethyl, a compound of formula 17 can be prepared by contacting dimethylcarbonate or diethylcarbonate, respectively, with 2-methylnicotinic acid.

Some embodiments for preparing a compound of formula I as described herein further comprise:

(ii) contacting a compound of formula 12:

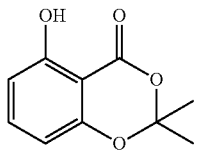

12 with a compound of formula 13:

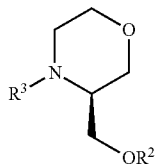

13 wherein:
$R^2$ is H or leaving group; and
$R^3$ is H or an amine protecting group;
under conditions sufficient to form a compound of formula 14:

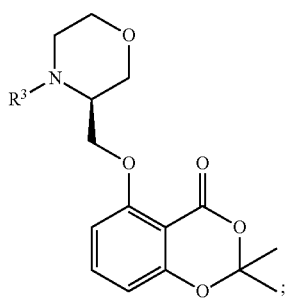

14 and
(iii) deprotecting a compound of formula 14 under conditions sufficient to form a compound of formula 10.

Some embodiments for preparing a compound of formula I as described herein further comprise:

(iv) contacting a compound of formula 12:

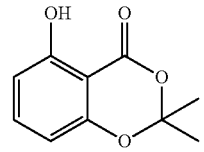

12 with a compound of formula 13:

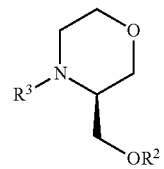

13 wherein:
$R^2$ is H; and
$R^3$ is an amine protecting group;
under conditions sufficient to form a compound of formula 14:

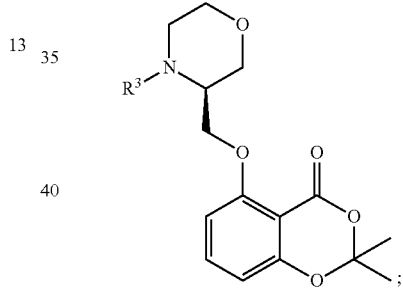

14 and
(v) deprotecting a compound of formula 14 under conditions sufficient to form a compound of formula 10.

In some embodiments, the reaction conditions of step (ii) or step (iv) (for forming a compound of formula 14) comprise an azodicarboxylate, wherein the azodicarboxylate is diisopropyl azodicarboxylate (DIAD). In some embodiments, the reaction conditions of step (ii) or step (iv) comprise a phosphine, wherein the phosphine is selected from triphenylphosphine and (2-hydroxybenzyl)diphenylphosphine oxide. In some embodiments, the reaction conditions of step (ii) or step (iv) comprise triphenylphosphine and diisopropyl azodicarboxylate.

In some embodiments, the reaction conditions of step (ii) or step (iv) (for forming a compound of formula 14) comprise a base selected from triethylamine (TEA), cesium carbonate, 1,8-diazabicyclo[5.4.0]undec-7-ene (DBU), and potassium carbonate. In some embodiments, the base is triethylamine (TEA). In some embodiments, the base is potassium carbonate. In some embodiments, the base is cesium carbonate. In some embodiments, the base is 1,8-diazabicyclo[5.4.0]undec-7-ene (DBU).

In some embodiments, the reaction conditions of step (ii) or step (iv) (for forming a compound of formula 14) comprise a solvent selected from tetrahydrofuran (THF), N,N-dimethylformamide (DMF), ethyl acetate (EtOAc), xylenes, and 2-methyltetrahydrofuran (MeTHF). In some embodiments, the reaction conditions of step (ii) or step (iv) comprise a temperature of about −5° C. to 85° C. In some embodiments, the reaction conditions of step (ii) or step (iv) comprise a temperature of about 0° C. to 50° C.

In some embodiments, the reaction conditions of step (iii) or step (v) (for forming a compound of formula 10) comprise a hydrogenation catalyst, wherein the hydrogenation catalyst is 5% Pd/C. In some embodiments, the reaction conditions of step (iii) or step (v) comprise a solvent selected from methanol and ethanol. In some embodiments, the reaction conditions of step (iii) or step (v) comprise a solvent, wherein the solvent is ethanol. In some embodiments, the reaction conditions of step (iii) or step (v) comprise a temperature of about 25° C.

In some embodiments, the reaction conditions of step (iii) or step (v) (for forming a compound of formula 10) comprise an acid. In some embodiments, the acid is hydrochloric acid, trifluoroacetic acid, or methanesulfonic acid. In some embodiments, the acid is methanesulfonic acid. In some embodiments, the reaction conditions of step (iii) or step (v) comprise a solvent, comprise a solvent selected from toluene, tetrahydrofuran (THF), N,N-dimethylformamide (DMF), ethyl acetate (EtOAc), xylenes, and 2-methyltetrahydrofuran (MeTHF). In some embodiments, the reaction conditions of step (iii) or step (v) comprise a temperature of about 40° C. to 60° C.

Some embodiments described herein further comprise: contacting a compound of formula 12:

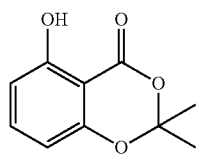

12 with a compound of formula 13:

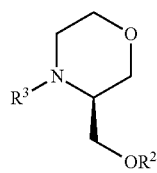

13 wherein:
R² is H or leaving group; and R³ is H; or
R² and R³, together with the atoms to which they are attached, join together to form a heterocyclic ring;
under conditions sufficient to form a compound of formula 10.

In some embodiments, the reaction conditions for this transformation comprise an azodicarboxylate, wherein the azodicarboxylate is diisopropyl azodicarboxylate (DIAD). In some embodiments, the reaction conditions for this transformation comprise a phosphine, wherein the phosphine is selected from triphenylphosphine. In some embodiments, the reaction conditions of this transformation comprise triphenylphosphine and diisopropyl azodicarboxylate.

In some embodiments, the reaction conditions of this transformation comprise a base selected from triethylamine (TEA), 1,8-diazabicyclo[5.4.0]undec-7-ene (DBU), potassium carbonate, cesium bicarbonate, and sodium hydride. In some embodiments, the base is triethylamine (TEA). In some embodiments, the base is cesium bicarbonate. In some embodiments, the base is sodium hydride. In some embodiments, the base is 1,8-diazabicyclo[5.4.0]undec-7-ene (DBU). In some embodiments, the base is potassium carbonate.

In some embodiments, the reaction conditions of this transformation comprise a solvent selected from tetrahydrofuran (THF), 2-methyltetrahydrofuran, N,N-dimethylformamide (DMF), dimethylacetamide (DMA), and dichloromethane (DCM). In some embodiments, the reaction conditions of this transformation comprise a temperature of about −5° C. to 55° C. In some embodiments, the reaction conditions of this transformation comprise a temperature of about 0° C. to 50° C.

Scheme 3 below shows yet another exemplary embodiment of the general method for the synthesis of a compound of formula I described herein.

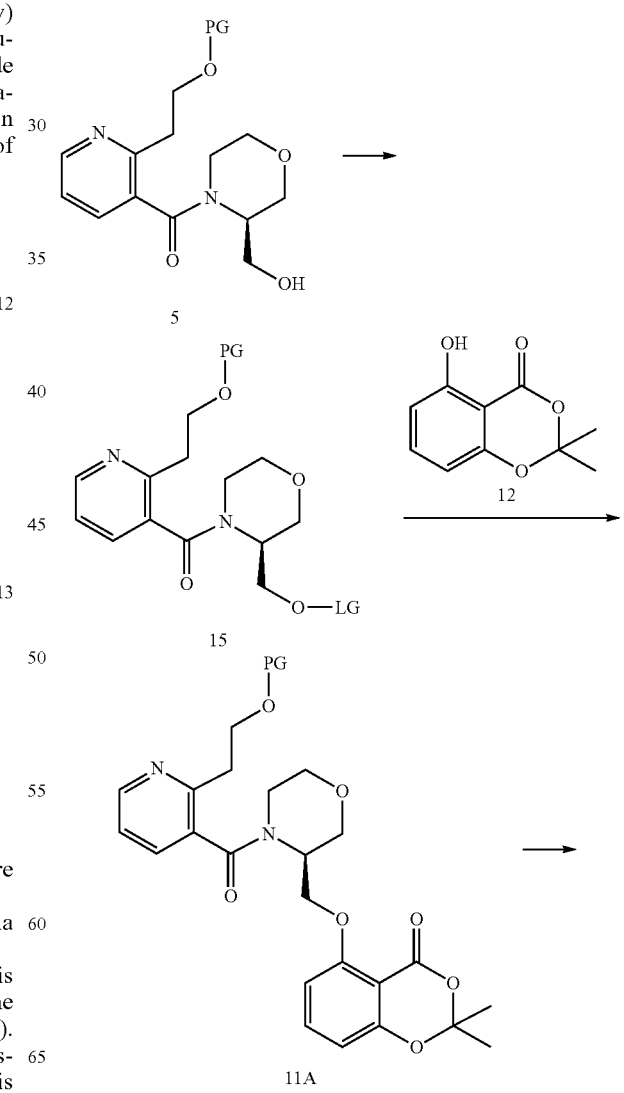

-continued

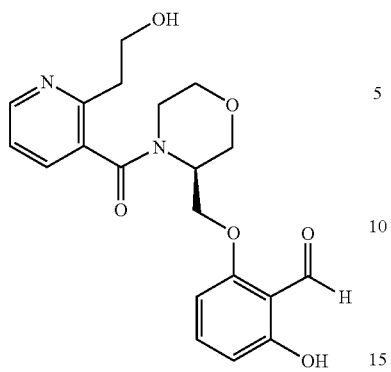

Compound I

In some embodiments, PG is a hydroxy protecting group, and LG is a leaving group.

In some embodiments, PG is tert-butyldimethylsilyl (TBS), tert-butyldiphenylsilyl (TBDPS), acetyl, (Ac), benzoyl (Bz), tetrahydropyranyl (THP), or benzyl (Bn). In some embodiments, PG is tert-butyldiphenylsilyl (TBDPS).

In some embodiments, LG is tosyl (Ts) or mesyl (Ms). In some embodiments, LG is tosyl (Ts).

In some embodiments, provided herein is a process for preparing a compound of formula I:

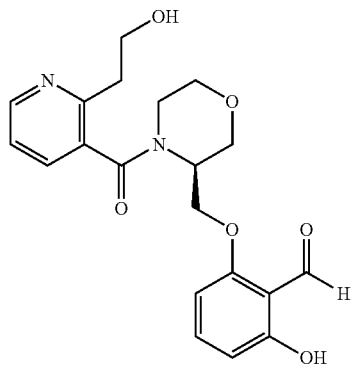

comprising:
(i) converting a compound of formula 5:

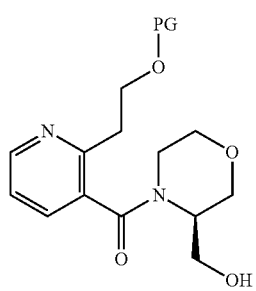

wherein PG is a hydroxy protecting group;

under conditions sufficient to form a compound of formula 15:

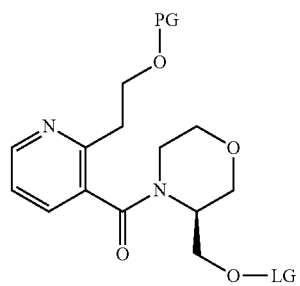

wherein LG is a leaving group;
(ii) contacting a compound of formula 15 with a compound of formula 12:

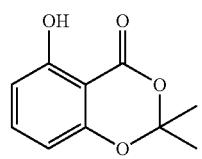

under conditions sufficient to form a compound of formula 11a:

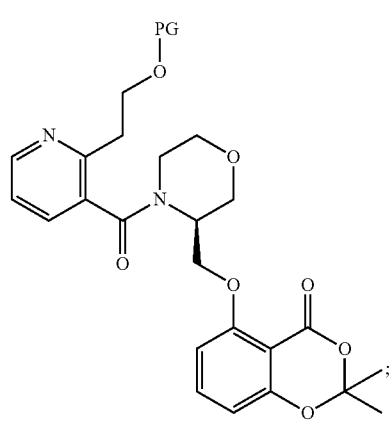

(iii) reducing and deprotecting a compound of formula 11a under conditions sufficient to provide a compound of formula I.

In some embodiments, the reaction conditions of step (i) comprise a base, wherein the base is selected from 1,4-diazabicyclo[2.2.2]octane (DABCO), 4-dimethylaminopyridine (DMAP), and pyridine. In some embodiments, the reaction conditions of step (i) comprise a solvent selected from ethyl acetate (EtOAc) and dichloromethane (DCM). In some embodiments, the reaction conditions of step (i) comprise a temperature of about −5° C. to 30° C. In some embodiments, the reaction conditions of step (i) comprise a temperature of about 0° C. to 25° C.

In some embodiments, the reaction conditions of step (ii) comprise a base, wherein the base is potassium carbonate. In some embodiments, the reaction conditions of step (ii)

comprise a solvent selected from tetrahydrofuran, 2-methyltetrahydrofuran (MeTHF), and ethyl acetate (EtOAc). In some embodiments, the reaction conditions of step (ii) comprise a temperature of about 25° C. to 80° C.

In some embodiments, the reaction conditions of step (iii) comprise first a reducing agent, wherein the reducing agent is diisobutylaluminium hydride (DIBAL-H). In some embodiments, the reaction conditions of step (iii) comprise a solvent selected from dichloromethane (DCM) and ethyl acetate (EtOAc). In some embodiments, the reaction conditions of step (iii) comprise a temperature of about −80° C. to 30° C. In some embodiments, the reaction conditions of step (iii) comprise a temperature of about −78° C. to 25° C.

In some embodiments, the reaction conditions of step (iii) further comprise a deprotecting reagent selected from tetrabutylammonium fluoride (TBAF) and hydrochloric acid (HCl). In some embodiments, the reaction conditions of step (iii) comprise a deprotecting reagent, wherein the deprotecting reagent is tetrabutylammonium fluoride (TBAF). In some embodiments, a compound of formula 11a is deprotected in situ with TBAF to form a compound of formula I. In some embodiments, the reaction conditions of step (iii) comprise a deprotecting reagent, wherein the deprotecting reagent is hydrochloric acid (HCl). In some embodiments, a compound of formula 11a is deprotected in situ with HCl to form a compound of formula I. In some embodiments, the reaction conditions of step (iii) further comprise a solvent selected from tetrahydrofuran (THF), 2-methyltetrahydrofuran, dichloromethane (DCM), methyl tert-butyl ether (MTBE), and ethyl acetate (EtOAc). In some embodiments, the reaction conditions of step (iii) further comprise a temperature of about 10° C. to 65° C. In some embodiments, the reaction conditions of step (iii) further comprise a temperature of about 15° C. to 50° C.

Scheme 4 below shows yet another exemplary embodiment of the general method for the synthesis of a compound of formula I described herein.

Scheme 4

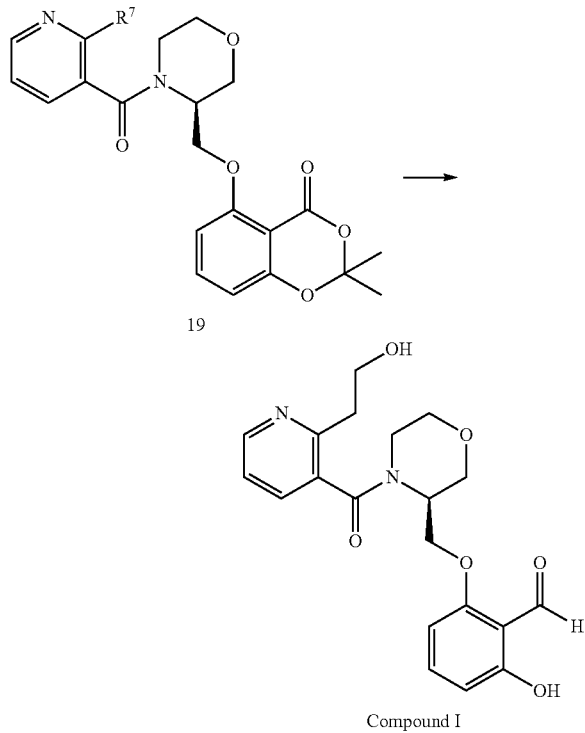

Compound I

In some embodiments, $R^7$ is halo or $C_{1-3}$ alkyl. In some embodiments, $R^7$ is halo. In some embodiments, $R^7$ is $C_{1-3}$ alkyl. In some embodiments, $R^7$ is methyl. In some embodiments, a compound of formula 19 may be achieved according to methods as described herein.

In some embodiments, compound of formula 19 is contacted with paraformaldehyde in the presence of a base under conditions sufficient to provide Compound I. Non-limiting examples of a base include lithium diisopropylamide (LDA), lithium bis(trimethylsilyl)amide (LiHMDS), and sodium bis(trimethylsilyl)amide (NaHMDS).

In some embodiments, compound of formula 19 is contacted with oxirane in the presence of, for example, iPrMgCl, under conditions sufficient to provide Compound I.

Intermediates and Crystalline Forms Thereof

It is contemplated that the exemplary syntheses shown in the Schemes provided herein, such as Scheme 2, may be particularly advantageous because such syntheses utilize intermediates that can be obtained in crystalline form.

Also provided herein is a crystalline form of compound of formula 10:

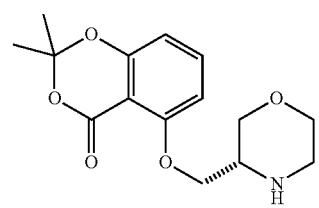

characterized by an X-ray powder diffractogram comprising the following peaks: 8.2, 20.3, 22.3, and 25.1°2θ, each ±0.2° 2θ, as determined on a diffractometer using Cu-Kα radiation. In some embodiments, the crystalline form of compound of formula 10 is characterized by a differential scanning calorimetry (DSC) curve comprising an endotherm at about 107.7° C. (peak temperature). In some embodiments, the crystalline form of compound of formula 10 is characterized by a differential scanning calorimetry (DSC) curve comprising an endotherm at about 103.5° C. (onset temperature).

Also provided herein is a crystalline form of a mesylate salt of compound of formula 10 characterized by an X-ray powder diffractogram comprising the following peaks: 11.5, 15.4, and 20.2°2θ, each ±0.2°2θ, as determined on a diffractometer using Cu-Kα radiation.

Also provided herein is a crystalline form of an HCl salt of compound of formula 10 characterized by an X-ray powder diffractogram comprising the following peaks: 7.5, 13.0, and 17.3°2θ, each ±0.2°2θ, as determined on a diffractometer using Cu-Kα radiation.

Also provided herein is a crystalline form of compound of formula 11d:

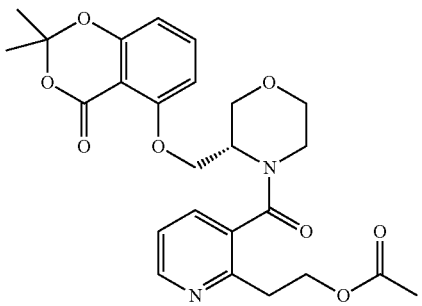

characterized by an X-ray powder diffractogram comprising the following peaks: 7.2, 14.5, 15.5, and 19.0°2θ, each ±0.2°2θ, as determined on a diffractometer using Cu-Kα radiation.

In some embodiments, the crystalline form of compound of formula 11d is characterized by a differential scanning calorimetry (DSC) curve comprising an endotherm at about 121° C. (peak temperature). In some embodiments, the crystalline form of compound of formula 11d is characterized by a differential scanning calorimetry (DSC) curve comprising an endotherm at about 114.4° C. (onset temperature). In some embodiments, the crystalline form of compound of formula 11d is characterized by a differential scanning calorimetry (DSC) curve comprising an endotherm at about 201.5° C. (peak temperature). In some embodiments, the crystalline form of compound of formula 11d is characterized by a differential scanning calorimetry (DSC) curve comprising an endotherm at about 190.0° C. (onset temperature).

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

The compounds including intermediates may be prepared using methods disclosed herein and routine modifications thereof which will be apparent given the disclosure herein and methods well known in the art. Conventional and well-known synthetic methods may be used in addition to the teachings herein. The synthesis of compounds described herein, may be accomplished as described in the following examples. If available, reagents may be purchased commercially, e.g. from Sigma Aldrich or other chemical suppliers. Unless otherwise noted, the starting materials for the following reactions may be obtained from commercial sources.

Analytical Methods

Standard HPLC Conditions:

| Column | XBridge Shield RP18, 3.5 um particle size, 4.6 × 150 mm |
|---|---|
| Flow | 0.8 mL/min |
| Injection Volume | 5 uL |
| Column Temperature | 30° C. |
| Detector Wavelength | 220 nm |
| Mobile Phase | A, 0.05% TFA in water; B, 0.05% in MeCN |

| Gradient Program | Time (mins) | % A | % B |
|---|---|---|---|
| | 0.0 | 95 | 5 |
| | 10.0 | 52 | 48 |
| | 28.0 | 20 | 80 |
| | 29.0 | 0 | 100 |
| | 31.0 | 0 | 100 |
| | 31.1 | 95 | 5 |
| | 39.0 | 95 | 5 |

Peak assignments are based on RRT.

Instrumental Techniques

X-Ray Powder Diffraction (XRPD or XRD)

XRPD figures were generated using SSCI Pattern Match 3.0.4, unvalidated software.

XRPD patterns were collected with a PANalytical X'Pert PRO MPD or a PANalytical Empyrean diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e or NIST SRM 640f) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening and asymmetry from axial divergence. Diffraction patterns were collected using a scanning position-sensitive detector (X'Celerator) located 240 mm from the specimen and Data Collector software v. 2.2b or v. 5.5.

Reflection Geometry

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e or NIST SRM 640f) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 5.5.

Differential Scanning Calorimetry (DSC)

DSC was performed using a Mettler-Toledo DSC3+ differential scanning calorimeter. A tau lag adjustment was performed with indium, tin, and zinc. The temperature and enthalpy were adjusted with octane, phenyl salicylate, indium, tin and zinc. The adjustment was then verified with octane, phenyl salicylate, indium, tin, and zinc. The sample was placed into a hermetically sealed aluminum DSC pan, and the weight was accurately recorded. The pan was then inserted into the DSC cell. A weighed aluminum pan configured as the sample pan was placed on the reference side of the cell. The pan lid was pierced prior to sample analysis. Samples were analyzed from −30° C. to 250° C. @ 10°/min.

Example 1A: Preparation Method for Compound I Form I

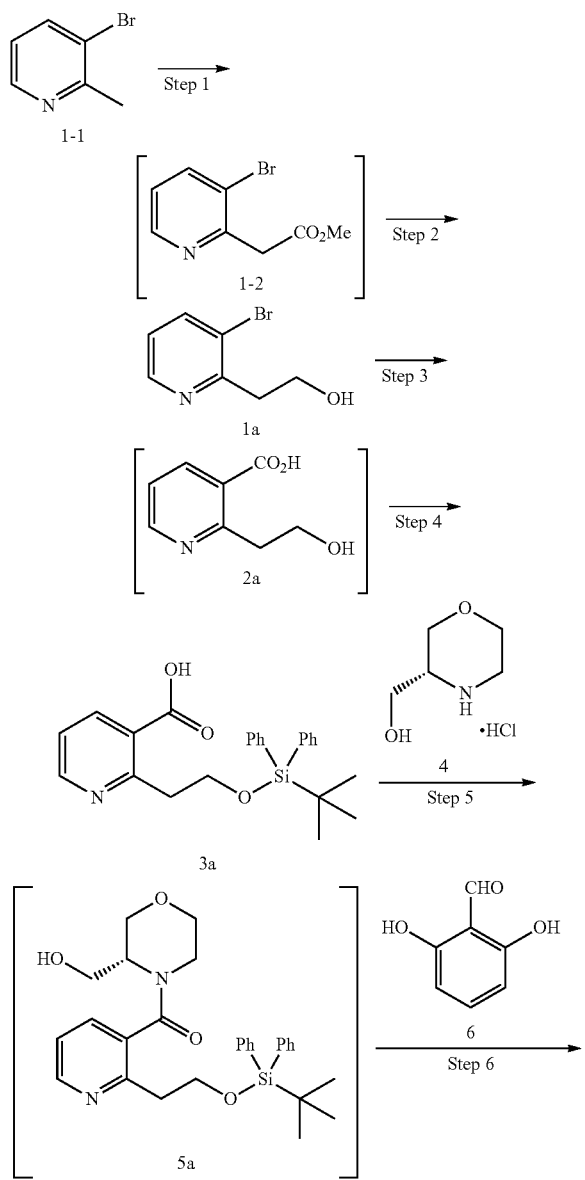

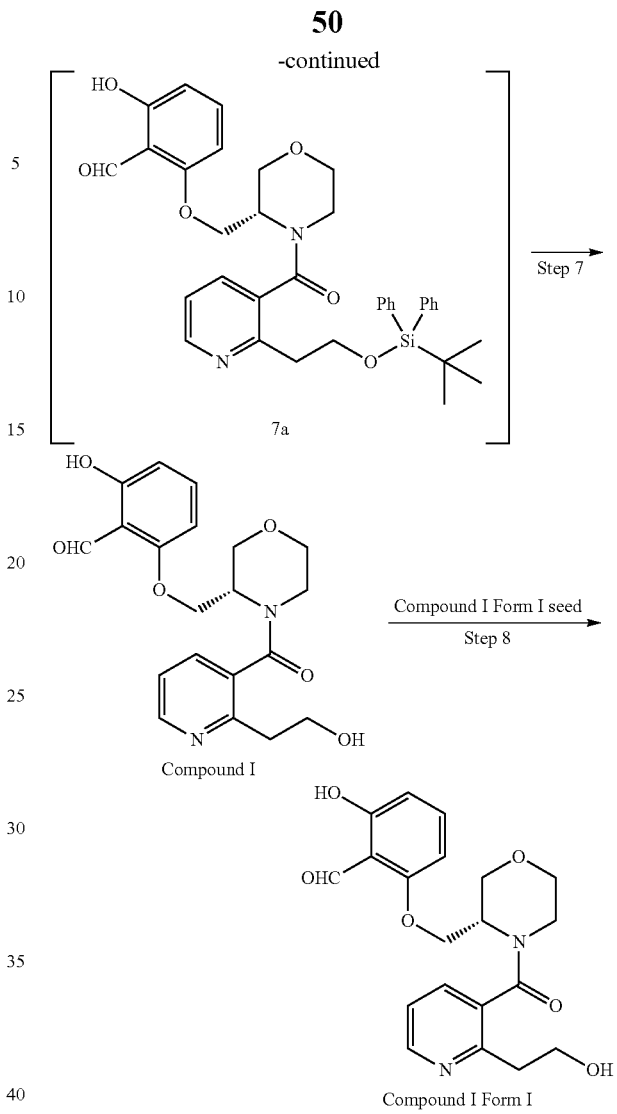

Step 1: Preparation of Compound 1-2

Compound 1-1 (1.0 eq.), dimethyl carbonate (1.2 eq.), and THF (5.0 V) were charged into a reactor. The resulting mixture was cooled to about −5±5° C. NaHMDS (2.0 eq.) was then charged into the reactor, and the resulting mixture was stirred for about 5 hours at −5±5° C. The reaction mixture was sampled throughout to determine reaction progress, with a target of 3.0% or less of compound 1-1 determining reaction completion. Upon completion, the reaction mixture was quenched with acetic acid (2.0 eq.) at −5±5° C. The quenched reaction mixture was then charged into a mixture of n-heptane (5.0 V) and water (5.0 V). The organic phase was separated and collected. The remaining aqueous phase was extracted with n-heptane (2.5 V) and THF (2.5 V). The organic phases were then combined and washed with an aqueous 8% NaHCO₃ solution (3.0 V), then were concentrated to no more than 3.0 V. The resulting concentrated solution of compound 1-2 was used directly in the next step.

Step 2: Preparation of Compound 1a

To the reactor containing the concentrated solution of compound 1-2 was charged EtOH (3.0 V) and CeCl₃·7H₂O (0.035 eq.) under N₂. The resulting mixture was cooled to 15±5° C. and was stirred for at least 1 hour, until the solution was clear. To the clear solution was then charged NaBH₄ (2.5 eq) in portions at 15±5° C., and the resulting reaction mixture was stirred for at least 8 hours while maintaining a temperature of 15±5° C. The reaction mixture was sampled throughout and reaction progress was determined by HPLC, with a target of no more than 5.0% of compound 1-2, or the analogous ethyl ester of compound 1-2, determining reaction completion. Upon completion, the pH of the reaction mixture was slowly adjusted with 3 N HCl to a pH of about 1-3, while maintaining a temperature of 15±5° C. The resulting solution was then stirred at 15±5° C. for at least 1 hour. To the reactor was then charged a 30% solution of NaOH (about 0.8 V) to adjust the pH of the mixture to about 7-8, while maintaining a temperature of 15±5° C. The reaction mixture was then concentrated to no more than 4.0 V, at a temperature of no more than 60° C. $H_2O$ (5.0 V) was then charged into the reactor. The resulting mixture was then concentrated to about 5-6 V, at a temperature of no more than 60° C. MTBE (5.0 V) was then charged into the reactor, and the resulting mixture was stirred for at least 30 minutes and stayed for at least 30 minutes. The aqueous and organic phases were separated, and the aqueous phase was extracted one time with MTBE (5.0 V). The isolated organic phases were combined, and to them was charged an aqueous 2 N NaOH solution. The resulting mixture was stirred for at least 4 hours at 25±5° C. The aqueous and organic phases were separated again, and the organic phase was washed with an aqueous 10% NaCl solution (4.0 V) one time. The washed organic phase was then concentrated to no more than 2.0 V. To the reactor was then charged DCM (5.0 V) and the resulting solution was concentrated to no more than 2.0 V. The concentrated solution was then cooled to 15±5° C., and n-heptane (2.0 V) was slowly charged to reactor, while maintaining a temperature of 15±5° C. Seeds of compound 1a (0.2% w/w), which were prepared according to methods described herein, were then charged to the reactor, and the resulting mixture was stirred for at least 30 minutes. N-heptane (6.0 V) was then slowly charged to the reactor at a temperature of 15±5° C. The resulting mixture was then stirred for at least 1 hour at 15±5° C. The mixture was then concentrated to 5.0 V at a temperature of no more than 40° C., and then stirred for at least 2 hours at 0° C. The resulting suspension was then filtered, and the filter cake was washed with n-heptane (2.0 V) one time and dried to provide compound 1a. LC/MS: m/z 202 (M+H).

Step 3: Preparation of Compound 2a

Compound 1a (1.0 eq.) and THF (5.0 V) were charged to a reactor, and the resulting mixture was cooled to −5±10° C. To the cooled mixture was charged i-PrMgCl (3.0 eq., 2 M) at −5±10° C. The resulting reaction mixture was stirred for about 3-5 hours at 0±5° C. The reaction was sampled to determine progress, with a target of 5.0% or less of compound 1a determining reaction completion. A second reactor was then charged with THF (16.0 V). To this second reactor, under blowing $CO_2$ atmosphere, was charged the Grignard reaction mixture at 0±10° C. The resulting mixture was stirred at 0±10° C. for about 2-5 hours. The reaction was sampled to determine progress, with a target of 5.0% or less of the debrominated analogue of compound 1-2 determining reaction completion. Upon completion, the reaction mixture was quenched with HCl in EtOAc (1 eq., 4 M) to provide a solution containing compound 2a. The quenched reaction mixture was used directly in the next step.

Step 4: Preparation of Compound 3a

To the reactor containing a solution of compound 2a was charged TBDPSCl (3.0 eq.) and 1H-imidazole (3.0 eq.). The resulting mixture was stirred at 35±5° C. for at least 18 hours. The reaction was sampled to determine progress, with a target of 5.0% or less of compound 2a determining reaction completion. Upon completion, the reaction mixture was cooled to 20±5° C., and MTBE (10.0 V) and water (5.0 V) were added. The resulting mixture was stirred for at least 30 minutes and stayed at least 30 minutes at 20±5° C. The organic and aqueous phases were then separated, and the isolated organic phase was washed with water (5.0 V), then an aqueous 20% NaCl solution (5.0 V). The washed organic phase was then collected and concentrated to about 4-7 V. Then n-heptane (5 V) was added to the organic phase, in order to switch solvents from THF to n-heptane. Concentration and charging with n-heptane (5 V) was repeated until less the 5.0% THF was observed in the mixture by GC. Then n-heptane (5 V) was charged to the mixture, which was stirred for at least 18 hours at 20±5° C. The resulting suspension was filtered, and the filter cake was washed with n-heptane (3.0 V) and dried at about 35-45° C. under vacuum (−0.08 MPa) to provide compound 3a. $^1$H NMR (DMSO-d6): 8.63 (dd, J=4.6, 1.8, 1H), 8.18–(dd, J=7.8, 1.8, 1H), 7.57-7.54 (m, 4H), 7.46-7.33 (m, 7H), 4.05 (t, J=6.8, 2H), 3.52 (t, J=6.8, 2H), 0.93 (s, 9H).

Step 5: Preparation of Compound 5a

A reactor under $N_2$ was charged with compound 3a (1.0 kg) and compound 4 HCl salt (0.45 kg, 1.2 eq.). To the inert reactor was charged 5.2 kg (5.5 V) of DMF, and the resulting mixture was agitated. Then DIEA (0.96 kg, 3.0 eq.) was charged to the mixture and the transfer line was rinsed with DMF (0.2 kg, 0.2 V). The reaction mixture was then cooled to 0±10° C. To the cooled reaction mixture was then charged HBTU (0.98 kg, 1.05 eq.), portion-wise, over no less than 2 hours, while maintaining an internal reaction temperature of 0±10° C. The reactor was then rinsed with DMF (0.3 kg, 0.3 V). The resulting reaction mixture was then agitated at 0±10° C. for no less than 1 hour. The reaction was sampled after 1 hour, and then every 2 hours subsequent until complete, and analyzed by HPLC to determine reaction progress, with a target of no more than 3.0% of compound 3a relative to the desired product, compound 5a. Upon completion, MTBE (3.7 kg, 5.0 V) was charged to the reaction mixture. Then purified water (5.0 kg) was charged to the reaction mixture, while maintaining an internal reaction temperature of no more than 30° C. The resulting mixture was then agitated at 25±5° C. for no less than 30 minutes. The reaction mixture was then allowed to settle for no less than 30 minutes, after which the aqueous layer was transferred to a new reactor, leaving only the organic phase in the initial reactor. The isolated aqueous phase was then extracted with MTBE (3.7 kg, 5.0 V). The MTBE extract of the aqueous phase was transferred back to the initial reactor containing the earlier isolated organic phase, and the remaining aqueous layer was discarded. The combined organic phase was then washed with brine (0.05 kg of NaCl in 5.0 kg of purified water) twice, and the resulting aqueous phase was separated and discarded. The resulting washed organic phase was sampled to determine product and solvent content. If residual DMF or HOBt content exceeded 0.5% by HPLC, further brine washes were completed.

In a separate reactor, a 20% aqueous NaCl solution (1.2 kg of NaCl in 4.6 kg of purified water) was prepared at 25±5° C. with agitation. This 20% aqueous NaCl solution was then transferred to the initial reactor, containing the combined organic phase of the reaction. The resulting mixture was then agitated at 25±5° C. for no less than 30 minutes. Again, the contents of the reactor were allowed to settle for no less than 30 minutes, then the aqueous phase was separated and discarded. The remaining organic phase was then concentrated under vacuum to a volume of about 2 L, at a temperature of no more than 40° C. To the resulting concentrated organic phase, DCM (4.0 kg, 3.0 V) was charged. The resulting solution was then concentrated under vacuum to a volume of about 2 L, at a temperature of no more than 40° C. DCM (4.0 kg, 3.0 V) charge, followed by concentration was then repeated. The resulting concentrated organic mixture was finally charged with DCM (4.0 kg, 3.0 V). The resulting mixture, containing compound 5a in DCM, was sampled to determine product purity and solvent content. If the residual water content of the sample was determined to exceed 0.1% by Karl Fischer analysis, or if the residual MTBE content of the sample was determined to exceed 3.0% by GC, further cycles of DCM addition and concentration were completed. The product solution was used directly in the next step.

Step 6: Preparation of Compound 7a

To the mixture of compound 5a in DCM was charged compound 6 (0.34 kg, 1.0 eq.), and the resulting mixture was agitated. PPh$_3$ (0.65 kg, 1.0 eq.) was then charged to the reaction mixture, and the reactor was rinsed via spray ball with DCM (1.5 kg, 1.1 V). The temperature of the reaction mixture was then adjusted to 30±5° C.

Into a separate reactor, DIAD (0.50 kg, 1.0 eq.) and DCM (2.2 kg, 1.7 V) were charged, and the resulting solution was agitated for 5 minutes. A portion of this DIAD solution (0.26 kg) was removed and stored in an appropriate container for later use. The remaining DIAD solution was then slowly transferred to the mixture of compound 5a and PPh$_3$ in DCM over no less than 2 hours, while maintaining an internal temperature of 30±5° C. The transfer line was also rinsed forward with DCM (0.3 kg, 0.2 V). The resulting mixture was agitated at 30±5° C. for no less than 30 minutes. The mixture was sampled to determine reaction progress, with a target of no more than 5.0% of compound 5a relative to the desired product, compound 7a, as measured by HPLC. If the desired ratio of starting material to product is not observed, the previously apportioned aliquot of DIAD solution can be added, and the resulting mixture can be further agitated for 30 minutes, until the reaction is complete. Upon reaction completion, purified water (0.02 kg) was charged to the reaction mixture while maintaining a reaction temperature of 30±5° C. The resulting mixture was agitated at 30±5° C. for no less than 1 hour. The reaction mixture was sampled to determine product purity via HPLC. The reaction mixture was then concentrated under vacuum to a volume of no more than 2.8 L, at a temperature of no more than 40° C. To the concentrated reaction mixture was charged THF (3.0 kg, 3.4 V). The resulting solution was then concentrated under vacuum to a volume of no more than 2.8 L, at a temperature of no more than 40° C. To the resulting concentrated reaction mixture of compound 7a was again charged THF (5.8 kg, 6.5 V), and the temperature was adjusted to no more than 30° C. The mixture, containing compound 7a in THF, was sampled to determine product purity and solvent content. Residual water content was checked by Karl Fischer analysis. The mixture was used immediately in the next step.

Step 7: Preparation of Compound I

To the mixture of compound 7a in THF was charged a 1 M solution of TBAF in THF (1.0 kg, 0.45 eq.), while maintaining an internal temperature of 35° C. The transfer line was rinsed forward with THF (0.2 kg, 0.2 V). The reaction temperature was then adjusted and maintained at 30±5° C., and the reaction was agitated for no less than 12 hours. The reaction was sampled after 12 hours, and then every 3 hours subsequent, and analyzed by HPLC to determine reaction progress, with a target of no more than 2.0% of compound 7a relative to Compound I determining reaction completion. Upon completion, the reaction mixture was concentrated under vacuum to a volume of about 2.8 L, at a temperature of no more than 50° C. The temperature of the concentrated reaction mixture was then adjusted to 20±5° C.

In a separate reactor, an aqueous 1.2 M HCl solution (9.6 kg of purified water and 1.34 kg of HCl) was prepared at 20±5° C. This aqueous 1.2 M HCl solution was then transferred to the reactor containing the concentrated reaction mixture of crude Compound I. The resulting mixture was then agitated for no less than 10 minutes, then toluene (4.9 kg, 5.6 V) was added. The resulting mixture was then agitated at 20±5° C. for no less than 30 minutes. The contents of the reactor were then allowed to settle for no less than 1 hour, after which the aqueous layer was transferred to a new reactor, and the remaining organic phase was discarded. The isolated aqueous phase was then washed with toluene (4.9 kg, 5.6 V) twice more. DCM (22.3 kg, 16.8 V) was then charged to the aqueous phase, and the resulting mixture was agitated. The pH of the aqueous phase was then adjusted to 8.0-10.0 by slowly adding K$_2$CO$_3$, while maintaining an internal temperature of 20±5° C. The contents of the reactor were then allowed to settle for no less than 30 minutes, after which the organic layer was transferred to a new reactor, and the remaining aqueous phase was discarded. The isolated organic phase was then washed with purified water (5.6 kg) three times. The purity of crude Compound I contained in the isolated organic phase was then determined by HPLC. The organic phase was then concentrated under vacuum to a volume of about 1.1 L, at a temperature of no more than 50° C. The concentrated organic phase was then charged with EtOAc (2.0 kg, 2.2 V), and the resulting solution was concentrated under vacuum to a volume of about 1.1 L, at a temperature of no more than 50° C. This EtOAc addition, followed by concentration step was then repeated. The concentrated organic phase was then charged with EtOAc (2.0 kg, 2.2 V), and the resulting solution was agitated for no less than 5 minutes. The solution was sampled to determine product and relative solvent content by $^1$H NMR. Then EtOAc (2.2 kg, 2.5 V) and Celite (0.22 kg) were charged to the solution containing crude Compound I.

In a separate vessel, EtOAc (3.3 kg, 3.7 V) and Darco KB-G (0.45 kg) were mixed. The wet Darco KB-G was then added to the Celite-containing mixture, and the vessel and transfer line was rinsed forward with EtOAc (2.5 kg, 2.8 V). The temperature of the resulting mixture was then adjusted to 60-65° C., and the reactor was agitated for no less than 1 hour.

In a separate reactor, EtOAc (10.2 kg, 11.2 V) was warmed to 60 to 65° C. The Celite/crude Compound I/Darco KB-G mixture was then filtered through a Celite pad into a separate reactor. The filtered waste cake was then washed twice with the hot EtOAc previously prepared, with the wash being added to the reactor containing the filtrate. The combined filtrate and wash was then concentrated under vacuum to a volume of 12.0 L, at a temperature of no more than 50° C. To the concentrated solution was again charged Celite (0.22 kg) and Darco KB-G (0.45 kg), which was wetted with EtOAc as described previously. The temperature of the resulting mixture was then adjusted to 60-65° C., and the reactor was agitated for no less than 1 hour.

The resulting Celite/Compound I/Darco KB-G mixture was again filtered through a Celite pad into a separate reactor. The filtered waste cake was again washed twice with further hot EtOAc, as was previously prepared. The wash was again added to the reactor containing the filtrate. The resulting solution was sampled to determine the purity of Compound I via HPLC. The solution was then concentrated under vacuum to a volume of about 1.1 L, at a temperature of no more than 50° C. The reactor was then rinsed via spray ball with EtOAc (0.3 kg, 0.3 V), and the temperature of the resulting solution was adjusted to 20±5° C. Compound I Material II (also referred to as Compound I Form II) seed crystals (0.56 g, 0.05 wt %), which were prepared using similar conditions as described herein and in U.S. Provisional Application No. 63/188,833 (filed on May 14, 2021, and titled "Solid Forms of a Modulator of Hemoglobin") and PCT Application No. PCT/US22/29289 (filed on even date herewith, and titled "Solid Forms of a Modulator of Hemoglobin"), each of which is hereby incorporated by reference in its entirety, were then charged to the solution, and the reactor was agitated at 20±5° C. for no less than 5 hours. Compound I Form II is a crystalline form characterized by an X-ray powder diffractogram comprising the following peaks: 14.9, 16.7, and 22.9°2θ±0.2° 2θ, as determined on a diffractometer using Cu-Kα radiation. In some embodiments, the diffractogram of Compound I Material II further comprises one or more peaks at: 18.4 or 19.2°2θ±0.2°2θ.

MTBE (5.0 kg, 6.7 V) was then transferred into the solution containing Compound I over no less than 2 hours, while the internal temperature of the solution was maintained at 20±5° C. Upon completion of the MTBE transfer, the resulting mixture was agitated at 20±5° C. for no less than 5 hours. The mixture was then sampled to determine the content of Compound I in the supernatant by HPLC. The mixture was then filtered, and the resulting filtrate was transferred into a separate reactor. The transferring reactor and wet filter cake were then washed with MTBE (2.5 kg, 3.4 V), and the washings were added to the filtrate. The wet filter cake was then deliquored under vacuum for no less than 30 minutes, and then dried under vacuum at no more than 50° C., for no less than 16 hours, to provide Compound I. MS: m/z 387.15 (M+H). After 16 hours of drying, the solid product was sampled to determine residual solvent content, with a goal of no more than 0.5% of each EtOAc and MTBE, as determined by GC. If the product contains excess residual solvent after 16 hours, the drying process was continued and the solid was sampled at 4 hour intervals until the drying was determined to be complete. The purification steps described herein may be repeated as needed to achieve desired purity levels.

Step 8: Preparation of Compound I Form I

Compound I (1.0 kg) and EtOAc (2.7 kg, 3.0 V) were charged to a reactor, and the resulting mixture was agitated. The temperature of the resulting mixture was adjusted and maintained at 60±10° C., and the mixture was agitated for no less than 30 minutes until all solids were completely dissolved. Upon completion of dissolution, the reactor contents were filtered through a cartridge filter and the filtrate was transferred to a separate reactor. The first reactor and transfer line were rinsed forward through the cartridge filter with EtOAc (1.8 kg, 2.0 V), and the collected rinses were added to the filtrate in the separate reactor. The temperature of the combined rinses and filtrate was adjusted to no more than 50° C., and the mixture was then concentrated under reduced pressure to a volume of about 3 L. The reactor was then rinsed with EtOAc (0.7 kg, 0.8 V), and the temperature of the contents was adjusted to 65±5° C. The resulting mixture was then agitated for no less than 30 minutes at 65±5° C. If any solids were observed, agitation was allowed to continue until all solids were completely dissolved. The temperature of the resulting solution was then adjusted to 26±3° C. for no less than 1 hour. To the solution was then charged seed crystals of Compound I Form I (0.01 kg, 1.0 wt %), which were prepared according to methods described herein, while maintaining a temperature of 26±3° C. The resulting mixture was then agitated at 26±3° C. for no less than 20 hours. The supernatant concentration of Compound I was monitored during agitation by HPLC. During agitation, samples of about 2 mL were taken at 5 hour intervals. The samples were filtered through a syringe filter, and the resulting filtrate was analyzed. After 20 hours of agitation, approximately 30 mL were sampled from the mixture. The sample was passed through filter paper under vacuum, and the collected wet filter cake was deliquored for no less than 1 minute. The polymorph of the wet filter cake material was then determined. Upon completion of agitation, the temperature of the mixture was adjusted to 20±5° C. for no less than 1 hour.

MTBE (5.9 kg, 8.0 V) was then transferred, via a cartridge filter, into the mixture containing Compound I over no less than 3 hours, while the internal temperature of the mixture was maintained at 20±5° C. The resulting mixture was then agitated at 20±5° C. for no less than 18 hours. After agitating for about 5 minutes, approximately 30 mL were sampled from the mixture. The sample was passed through filter paper under vacuum, and the collected wet filter cake was deliquored for no less than 1 minute. The polymorph of the wet filter cake should be Compound I Form I by XRD. During the polymorph analysis, the bulk material should continue to be agitated. If the polymorph of the sample was determined to be Compound I Form I, the agitation was continued for no less than 18 hours. If the polymorph of the sample was determined to not be Compound I Form I, the temperature of the contents of the reactor was adjusted and maintained at 50±5° C., and the mixture was agitated for no less than 2 hours. Then, the temperature of the mixture was adjusted to 20±5° C. for no less than 2 hours. The resulting mixture was then agitated at 20±5° C. for no less than 18 hours. The same sampling and polymorphic analysis procedure as was previously described was completed. If the polymorph of the sample was then determined to be Compound I Form I, the agitation was continued for no less than 18 hours. If the polymorph of the sample was determined to not be Compound I Form I, the heating-cooling cycle can be repeated.

After the polymorphic form of the wet filter cake was confirmed to be Compound I Form I, the supernatant concentration of Compound I was checked via HPLC, as was previously described. Upon completion of agitation, the mixture was filtered, and the resulting filtrate was transferred into a separate reactor. The transferring reactor and the wet filter cake were then washed with MTBE (a minimum of 2.2 kg, 3.0 V) via a cartridge filter, and the washings were added to the filtrate. The resulting wet filter cake was then deliquored under vacuum for no less than 1 hour, and then dried under vacuum at no more than 50° C., for no less than 16 hours, to provide Compound I Form I.

Example 1B: Preparation Methods for Compound I Form I

Method A

A solution of amorphous Compound I, which can be made according to methods known in the art, in MeCN (>540 mg/mL) was refrigerated for 4 days and then placed in a freezer for 1 day. The solids were filtered and dried under nitrogen to provide Compound I Form I.

Method B

Compound I Form I was also prepared as follows: Amorphous Compound I was slurried in ether with seeding with Compound I Form I from another experiment (prepared as described herein) at ambient temperature for 1 day, providing Compound I Form I.

Method C

In a 50 L reactor, a solution of (R)-(2-(2-((tert-butyldiphenylsilyl)oxy)ethyl)pyridin-3-yl)(3-(hydroxymethyl)morpholino)methanone in THF (6.07 kg in about 30 L THF), 2,6-dihydroxybenzaldehyde (1.2 equiv) and triphenylphosphine (1.3 equiv) were placed. The resulting mixture was warmed to 30° C. To the mixture was added a solution of DIAD in THF (1.3 equiv in about 9 L of THF) dropwise maintaining the temperature between 25° C. and 35° C. The reaction mixture was stirred for 30 min at 30° C. To the reaction mixture was added water (0.6 equiv), and the mixture was stirred for additional 1 h at 30° C.

To the reaction mixture was added a solution of TBAF in THF (0.5 equiv, 1 M solution in THF), and the mixture was stirred for 18 h. The reaction mixture was concentrated to remove most of THF under vacuum, maintaining the temperature below 50° C. To the residue was added 1.2 N HCl aq. (about 72 L) and toluene (about 30 L). The mixture was stirred for 15 min at 20° C., and the layers were separated. The aqueous layer was extracted with toluene twice (about 30 L per extraction). To the aqueous solution was added DCM (about 90 L), and to the mixture was added potassium carbonate until pH was between pH 8 and pH 10. The layers were separated. The DCM solution was washed with water (about 30 L) and concentrated under reduced pressure.

The residue was purified by silica gel chromatography (30 kg silica gel, a mixture of ethyl acetate:DCM:methanol=100:20:8 as eluent). This resulted in crude (S)-2-hydroxy-6-((4-(2-(2-hydroxyethyl)nicotinoyl)morpholin-3-yl)methoxy)benzaldehyde.

Crude (S)-2-hydroxy-6-((4-(2-(2-hydroxyethyl)nicotinoyl)morpholin-3-yl)methoxy)benzaldehyde, as an oil (4.4 kg, 11.4 mol), was dissolved in EtOAc (9.11 L). To the resulting solution was added seed crystal of Compound I Form I (which were prepared using similar conditions as described herein and in U.S. Provisional Application No. 63/188,833 (filed on May 14, 2021, and titled "Solid Forms of a Modulator of Hemoglobin"), and in PCT Application No. PCT/US22/29289 (filed on even date herewith, and titled "Solid Forms of a Modulator of Hemoglobin")), and the reaction mixture was stirred for 18 h at 15° C.-25° C. The resulting slurry was heated to 35° C.-45° C. and stirred for 18 h. To the slurry was added MTBE (52.8 L), and the mixture was stirred for 18 h maintaining the temperature at 35° C.-45° C. The slurry was cooled to 15° C.-25° C. and stirred for 18 h. The solids were collected by filtration, washed with MTBE (2.2 L) and dried under vacuum at 35° C.-45° C. This resulted in Compound I Form I.

Example 1C: Preparation Methods for Compound I Form II

Compound I Form I was dissolved in DCM, and the solution was added to heptane. The resulting suspension was stirred at ambient temperature for 3 days then in refrigerated conditions for 8 days, providing Compound I Material II.

Example 2: Alternate Preparation Methods for Compound 5a

Compound 5a may also be synthesized using various reaction conditions, and various coupling a as described below.

Amide Coupling Employing 1,1'-Carbonyldiimidazole (CDI)

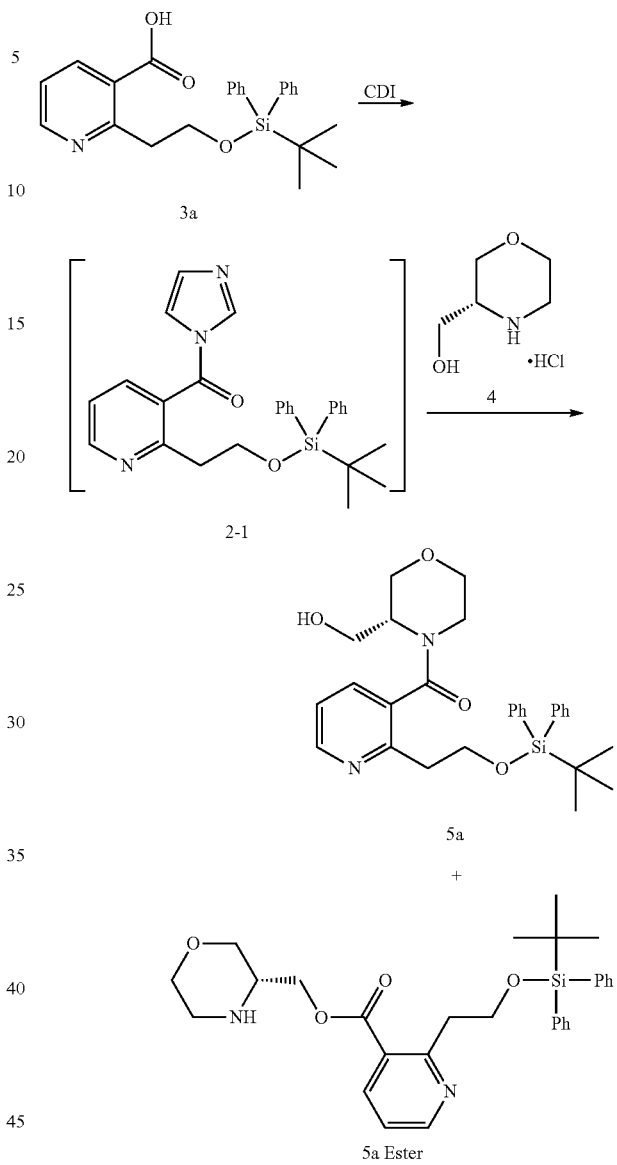

Compound 5a was also prepared using 1,1'-carbonyldiimidazole (CDI) as the activator of the carboxylic acid moiety of compound 3a, which provided activated acyl imidazole intermediate 2-1. Subsequent coupling with compound 4 HCl salt provided compound 5a and compound 5a ester, in varying ratios depending on reaction temperature and solvent employed (Table 1).

TABLE 1

| CDI Mediated Amide Couplings | | | | |
|---|---|---|---|---|
| Conditions | Temp (° C.) | Time (h) | Result (HPLC area %) (Intermediate 2-1:Compound 5a:Compound 5a ester) | Notes |
| Compound 3a (1.0 eq., 2.0 g) Compound 4 | 40-80 | 23 | 0.1:76.3:0.2 | 17 area % RT 12.4 min (m/z 447) |

TABLE 1-continued

CDI Mediated Amide Couplings

| Conditions | Temp (° C.) | Time (h) | Result (HPLC area %) (Intermediate 2-1:Compound 5a:Compound 5a ester) | Notes |
|---|---|---|---|---|
| HCl (2.0 eq.) TEA (3.0 eq.) CDI (1.5 eq.) ACN (10 V) Compound 3a (1.0 eq., 2.0 g) Compound 4 HCl (1.2 eq.) | 70 | 34 | 0.1:73.1:0.5 | 22 area % RT 12.4 min |
| TEA (3.0 eq.) CDI (1.2 eq.) ACN (10 V) Compound 3a (1.0 eq., 2.0 g) Compound 4 HCl (1.2 eq.) | 60 | N/A | N/A | Slow formation of Intermediate 2-1 |
| TEA (3.0 eq.) CDI (1.2 eq.) THF (10 V) Compound 3a (1.0 eq., 2.0 g) Compound 4 HCl (1.2 eq.) | 60 | N/A | N/A | Slow formation of Intermediate 2-1 |
| TEA (3.0 eq.) CDI (1.2 eq.) Dioxane(10 V) Compound 3a (1.0 eq., 2.0 g) Compound 4 HCl (1.2 eq.) | 60 | N/A | N/A | Slow formation of Intermediate 2-1 |
| TEA (3.0 eq.) CDI (1.2 eq.) DMF(10 V) | | | | |

Amide Coupling Employing Propylphosphonic Anhydride (T3P)

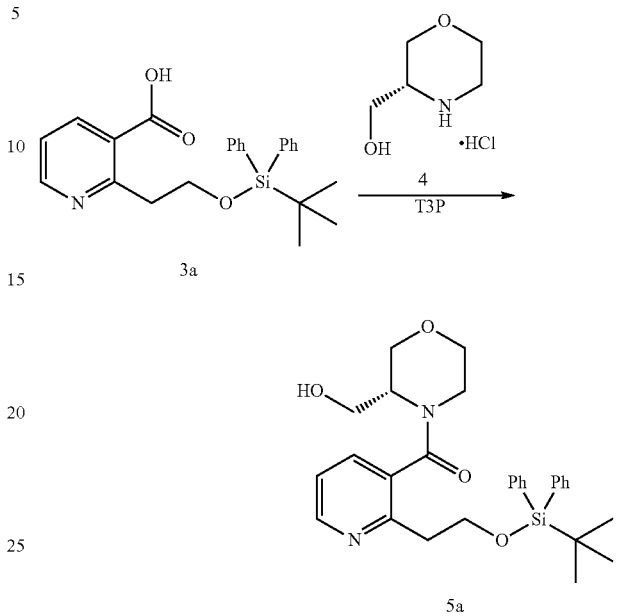

Similarly, compound 5a was also prepared using propylphosphonic anhydride (T3P) as the activator of the carboxylic acid moiety of compound 3a. Subsequent coupling with compound 4, both the HCl salt and free base forms, provided compound 5a and a byproduct impurity, in varying ratios depending on reaction temperature and duration (Table 2).

TABLE 2

T3P Mediated Amide Couplings

| Compound 3a | Compound 4 HCl | Base | T3P (50 wt % in EA) | Solvent | T (° C.) | Time (h) | Compound 3a: Compound 5a (HPLC area %) |
|---|---|---|---|---|---|---|---|
| 0.5 g (1 eq.) | 0.23 g (1.2 eq.) | DIEA (5 eq.) | 0.84 g (1.1 eq.) | DMF (10 V) | 20 | 1 | 7.22:66.97 |
| 0.5 g (1 eq.) | 0.23 g (1.2 eq.) | DIEA (5 eq.) | 0.96 g (1.2 eq.) | DMF (10 V) | 20 | 1 | 5.94:64.64 |
| 0.5 g (1 eq.) | 0.23 g (1.2 eq.) | DIEA (5 eq.) | 1.06 g (1.3 eq.) | DMF (10 V) | 20 | 1 | 4.16:70.24 |
| 0.5 g (1 eq.) | 0.23 g (1.2 eq.) | DIEA (5 eq.) | 1.2 g (1.5 eq.) | DMF (10 V) | 0 | 16 | 3.8:71.24 |
| 0.5 g (1 eq.) | 0.23 g (1.2 eq.) | DIEA (5 eq.) | 1.2 g (1.5 eq.) | DMF (10 V) | 40 | 16 | 2.29:78.03: 11.39% byproduct impurity |
| 0.5 g (1 eq.) | 0.17 g (1.2 eq.) of free base form | DIEA (5 eq.) | 1.2 g (1.5 eq.) | DMF (10 V) | 20 | 16 | 5.96:65.45: 18.31% byproduct impurity |

Varying the stoichiometric ratio of compound 3a to compound 4, both the HCl salt and free base forms, was investigated to mitigate byproduct impurity formation (Table 3).

TABLE 3

Investigation of Stoichiometric Ratio of Starting Materials in T3P Mediated Amide Couplings

| Compound 3a | Compound 4 HCl | Base | T3P (50 wt % in EA) | Solvent | T (° C.) | Time (h) | Compound 3a: Compound 5a: Byproduct Impurity (HPLC area %) |
|---|---|---|---|---|---|---|---|
| 0.5 g (1 eq.) | 0.23 g (1.2 eq.) | DIEA (5 eq.) | 1.2 g (1.5 eq.) | DMF (10 V) | 20 | 1 | 7.29:50.45:29.37 |
| 0.5 g (1 eq.) | 0.38 g (2 eq.) | DIEA (5 eq.) | 1.2 g (1.5 eq.) | DMF (10 V) | 20 | 1 | 2.17:81.18:9.27 |
| 0.5 g (1 eq.) | 0.23 g (1.2 eq.) | DIEA (5 eq.) | 1.2 g (1.5 eq.) | DMF (10 V) | 20 | 10 mins after half of T3P charged | 26.15:58.43:11.1 |
|  |  |  |  |  |  | After all T3P charged | 6.70:68.81:15.86 |
| 0.5 g (1 eq.) | 0.23 g (1.2 eq.) | DIEA (5 eq.) | 1.2 g (1.5 eq.) | DMF (10 V) | 40 | 0.5 | 4.59:70.35:15.39 |
| 0.5 g (1 eq.) | 0.17 g (1.2 eq.) of free base form | DIEA (5 eq.) | 1.2 g (1.5 eq.) | DMF (10 V) | 20 | 16 | 7.63:71.6:16.25 |

Amide Coupling Employing N,N,N',N'-Tetramethyl-O-(JH-Benzotriazol-1-yl)Uronium Hexafluorophosphate (HBTU)

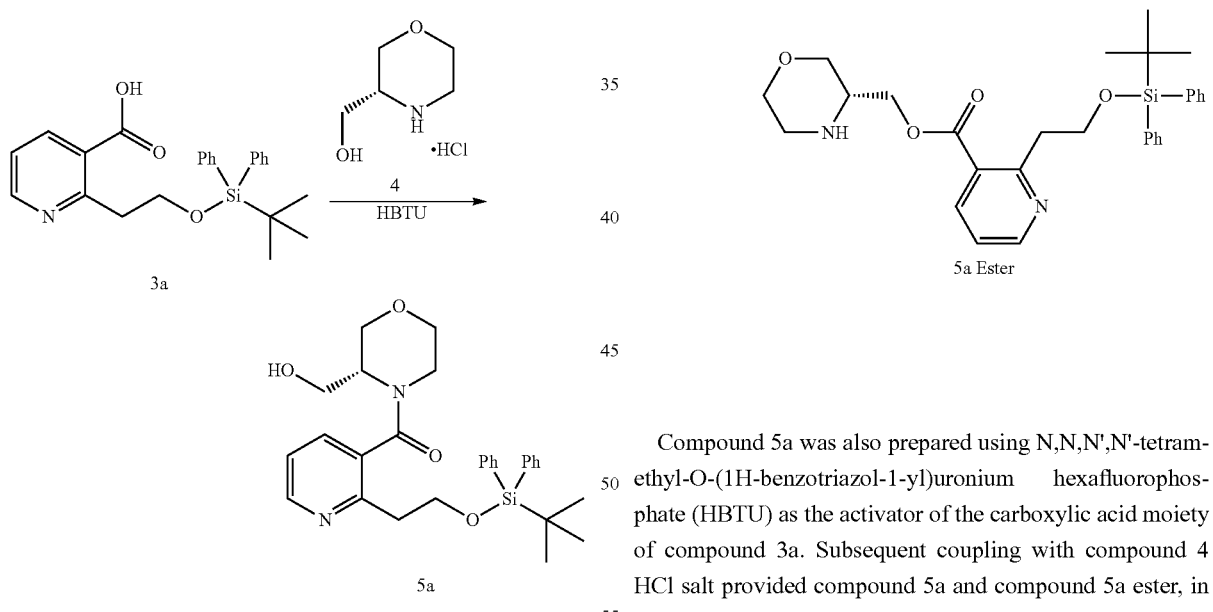

Compound 5a was also prepared using N,N,N',N'-tetramethyl-O-(1H-benzotriazol-1-yl)uronium hexafluorophosphate (HBTU) as the activator of the carboxylic acid moiety of compound 3a. Subsequent coupling with compound 4 HCl salt provided compound 5a and compound 5a ester, in varying ratios depending on reaction temperature and duration (Table 4). Table 4: HBTU Mediated Amide Couplings

TABLE 4

HBTU Mediated Amide Couplings

| Compound 3a | Compound 4 HCl | Base | Reagent | Solvent | T (° C.) | Time (h) | Compound 3a: Compound 5a (HPLC area %) |
|---|---|---|---|---|---|---|---|
| 0.5 g (1 eq.) | 0.23 g (1.2 eq.) | DIEA (4 eq.) | HATU (1.0 eq.) | DMF (10 V) | 20 | 1 | 0:89.18 |

TABLE 4-continued

HBTU Mediated Amide Couplings

| Compound 3a | Compound 4 HCl | Base | Reagent | Solvent | T (° C.) | Time (h) | Compound 3a: Compound 5a (HPLC area %) |
|---|---|---|---|---|---|---|---|
| 0.5 g (1 eq.) | 0.23 g (1.2 eq.) | DIEA (4 eq.) | HBTU g (1.0 eq.) | DMF (10 V) | 20 | 1 | 0:93.45 Note: 3.2% 5a Ester isomer at 9.158 min |
| 5 g (1 eq.) | 2.3 g (1.2 eq.) | DIEA (4 eq.) | HBTU g (1.0 eq.) | DMF (10 V) | 0-5 | 4 | 0.25:91.98:2.8% 5a Ester isomer |
| 50 g (1 eq.) | 23 g (1.2 eq.) | DIEA (4 eq.) | HBTU g (1.0 eq.) | DMF (10 V) | 0-5 | 4 | 0:93.53:2.6% 5a Ester isomer |
| 100 g (1 eq.) | 46 g (1.2 eq.) | DIEA (4 eq.) | HBTU g (1.0 eq.) (Add Additional 0.05 eq.) | DMF (10 V) | 0-5 | 1 h + 1 h after further HBTU addition | 3.8:87.5:2.8% 5a Ester isomer 0.2:92.5:2.5% 5a Ester isomer |

Compound 5a was a solid below −10° C., and precipitated out of EtOAc (2V)/heptane (2 V) under −15° C.

A variety of solvents were also investigated for the HBTU mediated amide coupling reaction, in order to optimize conversion and product purity (Table 5).

TABLE 5

Investigation of Solvents in HBTU Mediated Amide Couplings

| | HPLC area % (Compound 3a/Compound 5a/ Compound 5a ester) | |
|---|---|---|
| Solvent | T = 2 h | T = 24 h |
| DMF | 0/97/3 | NA |
| MeTHF | 34/50/16 | 0/84/16 |
| EtOAc | 0/87/13 | 0/89/11 |
| PhMe | 30/51/19 | 0/78/22 |
| MTBE | 82/10/8 | 0/69/31 |

Example 3: Alternate Solvents Used in the Preparation of Compound 7a

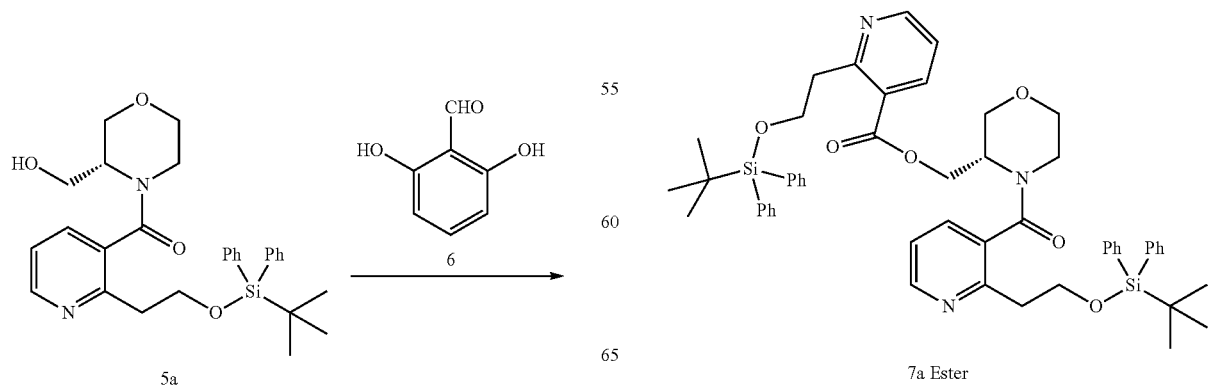

Compound 7a was prepared from compound 5a and compound 6 under Mitsunobu reaction conditions. Compound 7a DIAD adduct and compound 7a ester were also observed as byproducts of the Mitsunobu reaction. A variety of solvents were investigated to optimize the desired product conversion and purity for the Mitsunobu transformation (Table 6).

TABLE 6

Investigation of Solvents for Mitsunobu Reaction

| Reaction Condition | | HPLC data (RRT, % AN) | | | | | | |
|---|---|---|---|---|---|---|---|---|
| | | 0.51 | 0.62 | 0.68 | 1.00 | 1.04 | 1.09 | 1.31 |
| Solvent | DIAD (eq.) | (Compound 6) | (Compound 5a Ester) | (Compound 5a) | (Compound 7a) | (TBDPS-OH) | (DIAD adduct) | (Compound 7a Ester) |
| DCM | 0.95 (1 time kicker charge) | 5.93 | 3.19 | 3.23 | 80.82 | 0.89 | 0.95 | 1.55 |
| DCM | 0.90 | 5.69 | 2.42 | 0.04 | 79.90 | 1.62 | 1.51 | 2.08 |
| Solvent | DIA | 0.51 | 0.62 | 0.68 | 1.00 | 1.04 | 1.09 | 1.31 |
| THF | 0.90 | 5.95 | 1.92 | 1.19 | 79.09 | 1.81 | 3.30 | 2.08 |
| EtOAc | 0.90 | 6.49 | 2.31 | 2.23 | 76.35 | 1.66 | 1.29 | 2.08 |
| Toluene | 0.90 | 6.81 | 3.53 | 2.96 | 71.06 | 1.56 | 2.14 | 2.24 |
| Acetonitrile | 0.90 | 5.97 | 2.01 | 0.61 | 77.43 | 1.59 | 1.38 | 2.04 |

Example 4: Alternate Preparation Method 1 for Compound I

Preparation of Compound I via Compound 3b

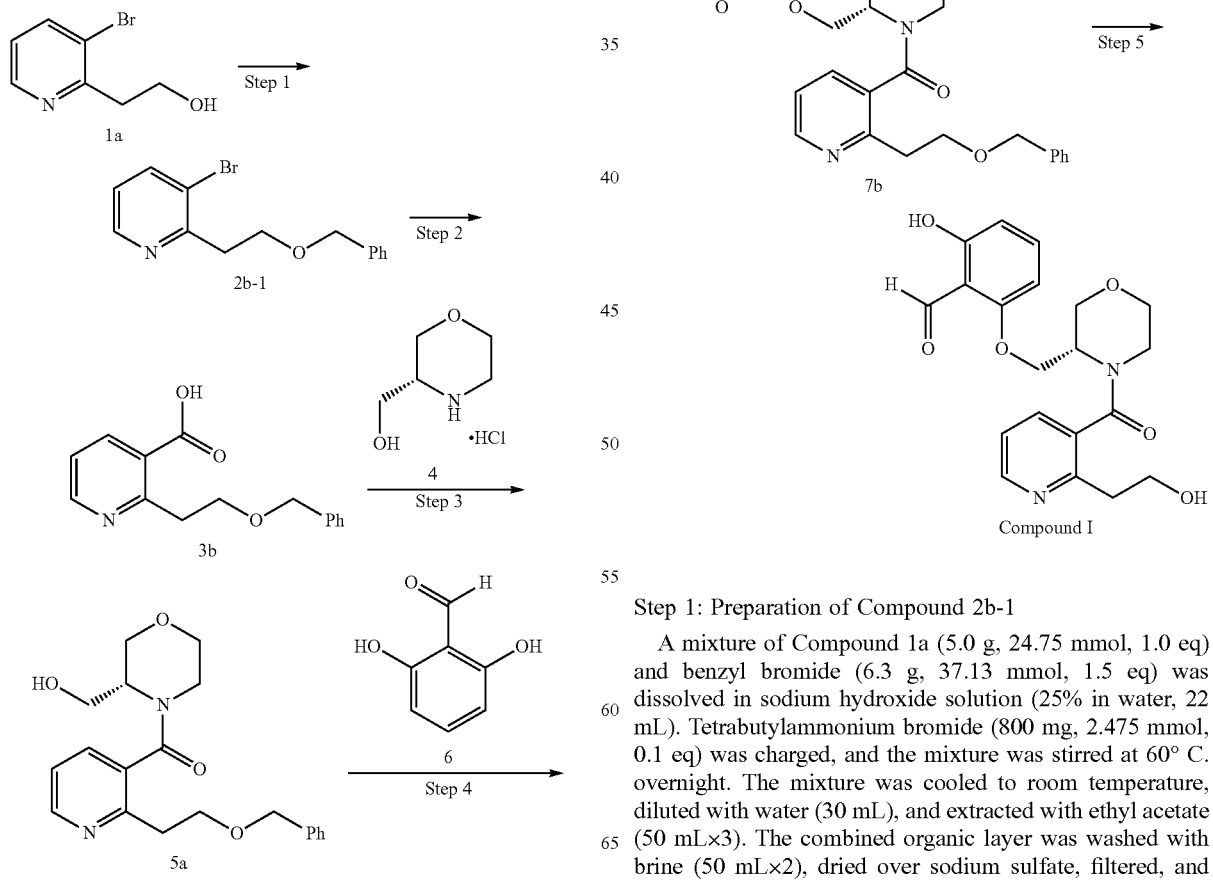

Step 1: Preparation of Compound 2b-1

A mixture of Compound 1a (5.0 g, 24.75 mmol, 1.0 eq) and benzyl bromide (6.3 g, 37.13 mmol, 1.5 eq) was dissolved in sodium hydroxide solution (25% in water, 22 mL). Tetrabutylammonium bromide (800 mg, 2.475 mmol, 0.1 eq) was charged, and the mixture was stirred at 60° C. overnight. The mixture was cooled to room temperature, diluted with water (30 mL), and extracted with ethyl acetate (50 mL×3). The combined organic layer was washed with brine (50 mL×2), dried over sodium sulfate, filtered, and concentrated. The residue was purified by silica gel column chromatography (petroleum ether: ethyl acetate=50:1-30:1-15:1-10:1-8:1-5:1) to obtain compound 2b-1. LC/MS: m/z 293.9 (M+H).

Step 2: Preparation of Compound 3b

Compound 2b-1 (5.57 g, 19.1 mmol, 1.0 eq) was dissolved in dry tetrahydrofuran (120 mL). The mixture was charged with nitrogen 3 times and cooled to −70° C. Then, to the mixture was added n-butyllithium (2.5 M, 9.2 mL, 22.92 mmol, 1.2 eq) slowly. The mixture was stirred at −70° C. for 30 min. The reaction was monitored by LCMS/HPLC. $CO_2$ gas (dried with conc. $H_2SO_4$) was bubbled into the reaction mixture. The mixture was stirred at −10° C. for 1 h. The reaction was monitored by LCMS/HPLC. The reaction mixture was quenched with water (60 mL) dropwise, and then stirred at room temperature for 10 min. To the mixture was added ethyl acetate and separated. The organic phase was extracted with water (60 mL). The combined aqueous phase was washed with ethyl acetate (40 mL). The aqueous phase was concentrated under reduced pressure to give the crude product. The crude product was purified by reverse phase column and lyophilized to give compound 3b. LC/MS: m/z 258.1 (M+H).

Steps 3 and 4: Preparation of Compound 5b and 7b

Compounds 5b (LC/MS: m/z 357.2 (M+H)) and 7b (LC/MS: m/z 477.2 (M+H)) were synthesized according to methods described herein.

Step 5: Preparation of Compound I

Compound 7b (4.0 g, 1.0 eq.) in DCM (40 mL, 10 V) was charged with $N_2$ and cooled to 0±5° C. To this mixture, $BCl_3$ in DCM (1M, 2 eq.) was added. The reaction mixture was stirred for about 2 h at 0±5° C. Additional $BCl_3$ in DCM (1M, 2 eq.) at 0±5° C. was added, and the reaction mixture was stirred for about 2 h at 0±5° C. To the mixture was charged water (10 V) at 0±5° C. The mixture was stirred for approximately 10 mins (aqueous phase pH was 1 to 2) and separated, and the aqueous phase was collected. The aqueous phase was washed with DCM (5 V). EtOAc was charged to the aqueous phase, and the pH was adjusted to 8 to 9 with $Na_2CO_3$. The mixture was stirred for about 10 mins and separated, and the EtOAc phase was collected and washed with water (5 V*2) twice. The EtOAc phase was washed with 15% aqueous solution of NaCl (5 V*2) once and then concentrated to about 2 V, heated to 40±5° C., and charged Compound I (Form I seed). This mixture was stirred for at least 18 h at 40±5° C. MTBE (12 V) was charged at 40±5° C., and the resulting mixture was stirred for at least 18 h at 40±5° C., cooled to 20±5° C., and stirred for at least 18 h. The mixture was filtered, and the filter cake was washed with MTBE (0.5 V) and dried under vacuum (P≤−0.08 MPa) at 40±5° C. until LOD ≤1.0%. LC/MS: m/z 387.2 (M+H).

Example 5: Alternate Preparation Method 2 for Compound I

Preparation of Compound I via Compound 3c

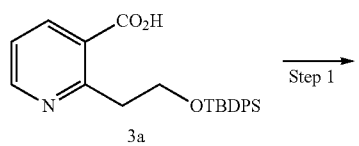
3a

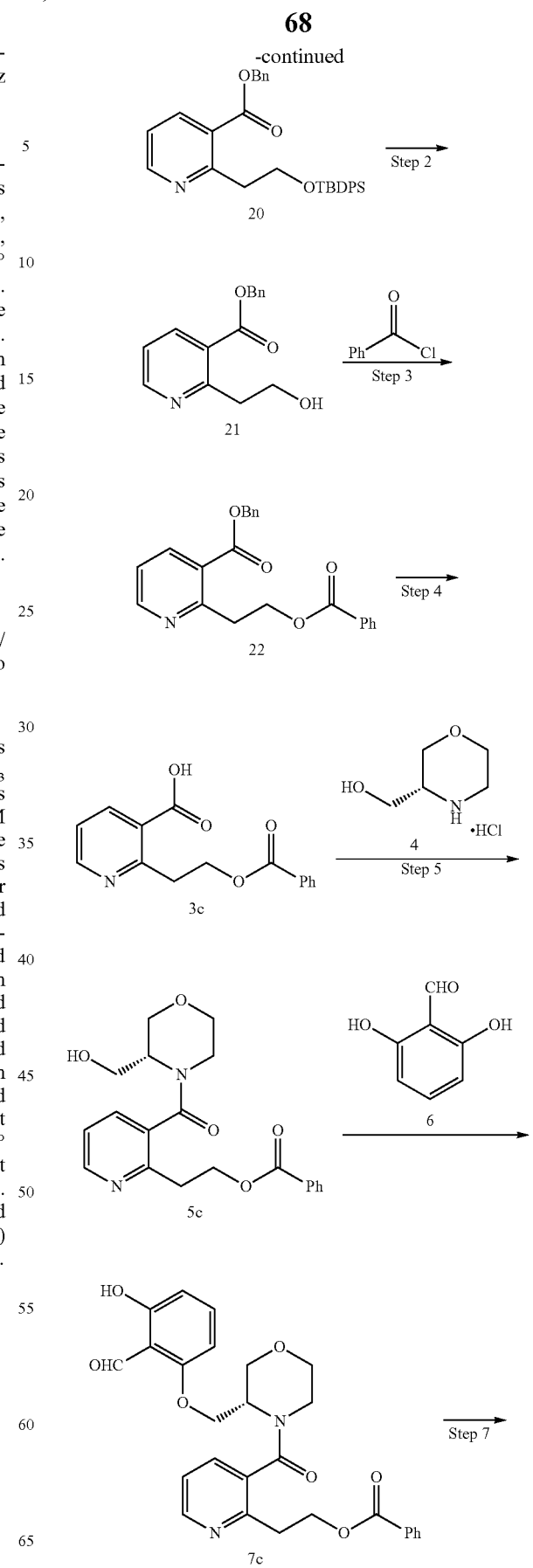

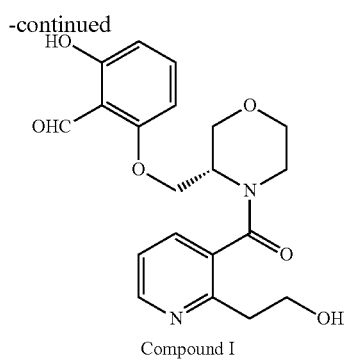

Compound I

Step 1: Preparation of Compound 20

To a mixture of Compound 3a (21 g, 51.7 mmol, 1.0 eq) in acetonitrile (210 mL), was added potassium carbonate (21.4 g, 155.1 mmol, 3.0 eq). The resulting mixture was stirred at 80° C. for 15 min. To the mixture was then charged benzyl bromide (26.5 g, 155.1 mmol, 3.0 eq), and the resulting mixture was stirred at 80° C. overnight. The reaction was monitored by LCMS. Upon completion, the reaction mixture was cooled to room temperature and filtered through a pad of celite and a sintered funnel. The filter cake was washed with ethyl acetate and the filtrate was concentrated to remove acetonitrile. To the provided residue was added water (200 mL) and ethyl acetate (300 mL), and the phases were separated. The aqueous phase was extracted with ethyl acetate (150 mL×2). The combined organic layer was washed with brine (200 mL), dried over sodium sulfate, filtered, and concentrated. The resulting residue was purified by silica gel column chromatography (petroleum ether: ethyl acetate=20:1-10:1-5:1) to provide Compound 20. LC/MS: m/z 496.0 (M+H).

Step 2: Preparation of Compound 21

To a mixture of Compound 20 (18.7 g, 37.78 mmol, 1.0 eq) in tetrahydrofuran (150 mL), was added pyridine hydrogen fluoride (16.8 g, 170 mmol, 4.5 eq) dropwise at 0° C. under nitrogen atmosphere. Then the mixture was allowed to warm to room temperature and was stirred for 2 h. The reaction was monitored by LCMS. Upon completion, the reaction was quenched with water (100 mL) and extracted with ethyl acetate (100 mL×3). The combined organic layer was washed with brine (100 mL), dried over sodium sulfate, filtered, and concentrated. The resulting residue was purified by silica gel column chromatography (dichloromethane-dichloromethane:methanol=200:1-150:1-100:1-50:1) to provide Compound 21. LC/MS: m/z 258.0 (M+H).

Step 3: Preparation of Compound 22

To a mixture of Compound 21 (4.6 g, 17.8 mmol, 1.0 eq) in dichloromethane (40 mL), was added triethylamine (5.4 g, 53.4 mmol, 3.0 eq) under a nitrogen atmosphere. To the resulting mixture was added benzoyl chloride (3.0 g, 21.4 mmol, 1.2 eq) dropwise at 0° C. Then the mixture was allowed to warm to room temperature and was stirred overnight. The reaction was monitored by LCMS/HPLC. Upon completion, the reaction was quenched with water (40 mL) and the phases were separated. The aqueous phase was extracted with dichloromethane (50 mL×2). The combined organic layer was washed with brine (50 mL), dried over sodium sulfate, filtered, and concentrated. The resulting residue was purified by silica gel column chromatography (petroleum ether: ethyl acetate=50:1-20:1-10:1-5:1-3:1) to provide Compound 22. LC/MS: m/z 362.0 (M+H).

Step 4: Preparation of Compound 3c

To a solution of Compound 22 (5.5 g, 15.2 mmol, 1.0 eq) in tetrahydrofuran (200 mL), was added Pd/C (1.1 g, 20% w/w) under a nitrogen atmosphere. The resulting mixture was evacuated and charged with hydrogen 3 times, then stirred at room temperature overnight. The reaction was monitored by TLC. Upon completion, the reaction mixture was filtered through a pad of celite and a sintered funnel. The filter cake was washed with tetrahydrofuran 3 times. The filtrate was concentrated under reduced pressure to provide Compound 3c. LC/MS: m/z 272.1 (M+H).

Steps 5 and 6: Preparation of Compound 5c and 7c

Compounds 5c (LC/MS: m/z 371.0 (M+H)) and 7c (LC/MS: m/z 491.4 (M+H)) were synthesized according to methods described herein.

Step 7: Preparation of Compound I

Compound 7c (1.0 equiv), MeOH (9V), and $H_2O$ (1V) were charged to a reactor under $N_2$, and the resulting mixture was cooled to 0° C. To the reactor was then charged LiOH (3 equiv) at 0° C., and the resulting mixture was stirred for 3 h at 0° C. The pH of the mixture was then adjusted to 6-7 with 1 N aqueous HCl. The mixture was concentrated to remove MeOH, then toluene (5 V) and 1 N HCl (5 V) were added. The layers were separated and the aqueous phase washed with toluene (2×5V). Ethyl acetate was charged to the aqueous phase and the pH adjusted to 8-9 with $NaHCO_3$. After stirring the biphasic mixture for 10 min, the layers were separated. The ethyl acetate layer was washed with water (2×5V), then with 15% aqueous NaCl solution (2×5V). The ethyl acetate layer was concentrated to approximately 2 V, heated to 40±5° C., and then seeded with Compound I Form I. After stirring for 18 h at 40±5° C., MTBE (12V) was charged and the resulting slurry was stirred for 18 h at 40±5° C. The mixture was then cooled to 20±5° C., stirred for 18 h, then filtered, and the filter cake washed with MTBE (0.5 V). The isolated Compound I was dried under vacuum (P≤−0.08 MPa) at 40±5° C. until LOD ≤1.0%. LC/MS: m/z 387.3 (M+H).

Example 6: Alternate Preparation Method 3 for Compound I

Preparation of Compound I via Compound 3d

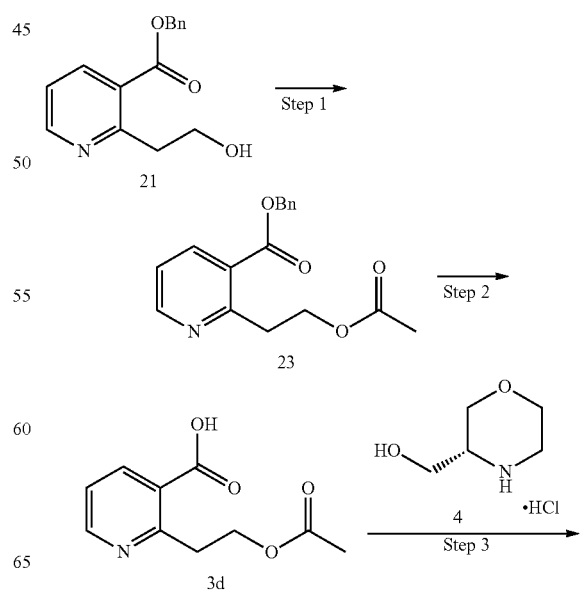

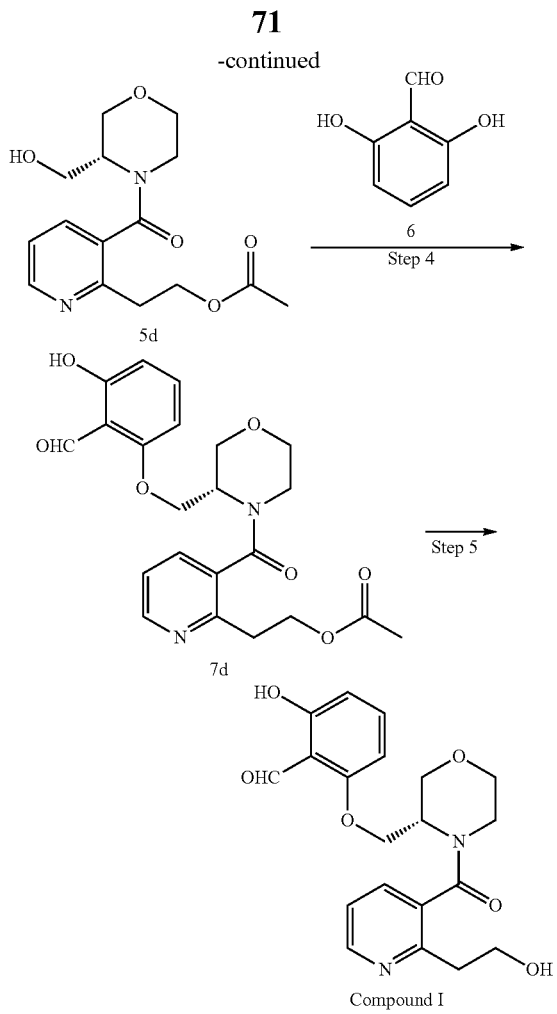

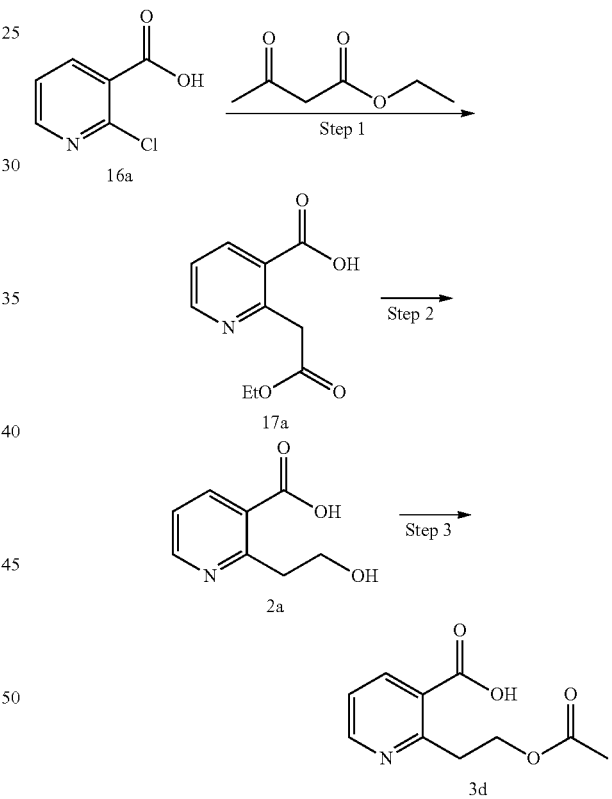

Step 1: Preparation of Compound 23

To a mixture of compound 21, synthesized as described herein, (8.0 g, 31.0 mmol, 1.0 eq) in dichloromethane (80 mL), was added triethylamine (9.4 g, 93.0 mmol, 3.0 eq) under a nitrogen atmosphere. To the mixture was then added acetic anhydride (6.33 g, 62.0 mmol, 2.0 eq) dropwise at 0° C. Then to the reaction was added 4-dimethylaminopyridine (756 mg, 6.2 mmol, 0.2 eq), and the resulting mixture was stirred at room temperature for 3 h. The reaction was monitored by TLC. Upon completion, the reaction was quenched with water (50 mL) and the phases were separated. The organic phase was extracted with dichloromethane (50 mL×2). The combined organic layer was washed with a saturated sodium chloride solution (50 mL), dried over sodium sulfate, filtered, and concentrated. The resulting residue was purified by silica gel column chromatography (petroleum ether: ethyl acetate=20:1-10:1-8:1-6:1-4:1-3:1-2:1) to provide compound 23. LCMS: m/z 300.2 (M+H).

Step 2: Preparation of Compound 3d

To a solution of compound 23 (5.3 g, 17.7 mmol, 1.0 eq) in dry tetrahydrofuran (60 mL), was added Pd/C (1.07 g, 20% w/w) under a nitrogen atmosphere. The resulting mixture was evacuated and charged with hydrogen 3 times, then stirred at room temperature overnight. The reaction was monitored by TLC. Upon completion, the reaction mixture was filtered through a pad of celite and a sintered funnel. The filter cake was washed with tetrahydrofuran 3 times. The filtrate was concentrated under reduced pressure to provide compound 3d. LC/MS: m/z 210.1 (M+H). $^1$H NMR (400 MHz, DMSO) δ 13.37 (s, 1H), 8.63 (dd, J=4.8, 1.8 Hz, 1H), 8.16 (dd, J=7.9, 1.8 Hz, 1H), 7.35 (dd, J=7.9, 4.8 Hz, 1H), 4.38 (t, J=6.9 Hz, 2H), 3.42 (t, J=6.8 Hz, 2H), 1.92 (s, 3H). $^{13}$C NMR (101 MHz, DMSO) δ 170.34, 167.83, 158.17, 151.59, 138.35, 126.77, 121.83, 62.95, 40.15, 39.94, 39.73, 39.52, 34.99, 20.73.

Steps 3 and 4: Preparation of Compound 5d and 7d

Compounds 5d (LCMS: m/z 309.2 (M+H)) and 7d (LC/MS: m/z 429.3 (M+H)) were synthesized according to methods described herein.

Step 5: Preparation of Compound I

Compound 7d (1.0 equiv), MeOH (18V), and H$_2$O (2V) were added to a vial under N$_2$ and cooled to 0° C. To the reaction vial was then charged LiOH (2.0 equiv) at 0° C., and the resulting mixture was stirred for 2 h at 0° C. The reaction mixture was sampled and analyzed by LC, with 99% conversion to Compound I observed.

Example 7: Alternate Preparation of Compound 3d

Step 1: Preparation of Compound 17a

A solution of 21 wt % sodium ethoxide in ethanol (52.1 g, 2.6 equiv) was charged to a reactor containing ethyl 3-oxobutanoate (12.2 g, 1.5 equiv) and MeTHF (50 mL) at 20° C. under N$_2$. Copper (II) acetate (0.99 g, 0.09 equiv) and 2-chloronicotinic acid (10.0 g, 1.0 equiv) were charged to the reactor, and the reaction mixture heated to 70-80° C. for 4.5 hours. The reaction mixture was cooled to room temperature, and MeTHF (50 mL, 5V) and 20 wt % aqueous citric acid (30 mL, 3V) charged. The mixture was stirred at room temperature for 19 hours, then the phases separated. The organic layer was concentrated to afford crude compound 17a. To the crude compound 17a was charged toluene (60 mL, 6 V), and MeTHF (5 mL, 0.5 V). The mixture was heated to 85° C., then cooled to room temperature to afford a slurry of compound 17a. The slurry was filtered, and the cake washed with toluene (20 mL, 2V). The solids were dried under vacuum at 50° C. to afford compound 17. LCMS: m/z 210.1 (M+H).

Step 2: Preparation of Compound 2a

A solution of 2 M lithium borohydride in THF (2.0 equiv, 4.9 equiv) was charged to a solution of compound 17a (1 g, 1.0 equiv) in isopropanol (10 mL, 10V) at 15-25° C. under $N_2$. After stirring for approximately 2 days the reaction mixture was quenched with acetone (2 equiv), then concentrate HCl (1.1 mL, 1.1 V) added and the resulting slurry cooled to 5° C. After aging 3 hours the slurry was filtered and the cake washed with MeCN (3 mL, 3V) and the solids dried under vacuum to afford compound 2a as an HCl salt. LCMS: m/z 168.1 (M+H). $^1$H NMR (400 MHz, $CD_3OD$) δ 9.04 (dd, J=8.1, 1.7 Hz, 1H), 8.86 (dd, J=5.8, 1.7 Hz, 1H), 8.02 (dd, J=8.1, 5.8 Hz, 1H), 3.96 (dd, J=6.2, 5.6 Hz, 2H), 3.61 (t, J=5.9 Hz, 2H).

Isolation of a freebase of compound 2a can be achieved according to methods known in the art. Aqueous 1 M sodium hydroxide (approximately 1 equiv) is charged to a mixture of compound 2a (1 equiv) in MeTHF (5 10V). The pH of the aqueous layer is adjusted to about 4 to 5. After mixing, the layers are separated, and heptane charged to the organic layer. Filtration provides compound 2a as a freebase.

Step 3: Preparation of Compound 3d

A solution of 4-dimethylamino pyridine (0.1 equiv) in THF (10V, 100 mL) under $N_2$ was cooled to −10° C. To this was charged acetic anhydride (1.25 equiv, 7.71 g) at −10° C. Compound 2a (1.0 equiv, 10 g) was then charged portionwise (2 g in 10 minute intervals) at −10° C. Following the addition the reaction mixture was stirred for approximately 4 hours at −10° C. A slurry formed, to which was added heptane (20 mL, 20 V). The solids were collected by filtration, then stirred with MTBE (10 V, 10 mL) overnight at room temperature. The solids were collected by filtration and washed with MTBE (1 mL, 1V), then dried under vacuum to afford compound 3d.

Example 8: Preparation of Compound Formula 13a

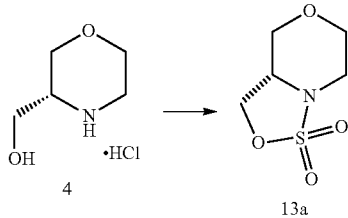 [SMILES: OC[C@@H]1COCCN1 ; Cl ; O=S1(=O)OC[C@@H]2COCCN21]

Compound 4 HCl salt (653 mg, 4.3 mmol, 1 eq), DCM (5 mL, 10 V), and pyridine (1.9 mL, 17.1 mmol, 4 eq) were added to a vial with a pressure relief cap. The reaction mixture was purged with $N_2$ for 5 minutes and then cooled to −78° C. in a dry ice-acetone bath. Sulfuryl chloride (0.3 mL, 4.3 mmol, 1 eq) was dissolved in 5 mL of DCM, then was added dropwise, while maintaining a temperature of −65° C. The resulting reaction mixture was then stirred for one hour at −78° C., and then was allowed to warm to 0° C. in an ice water bath and left stirring for an hour. The reaction mixture was then diluted with 30 mL of heptane and quenched with 20 mL of water. The layers were separated and the isolated aqueous layer was extracted twice with 20 mL of DCM. The combined organic layers were then washed with 20 mL of brine, dried with $Na_2SO_4$ and concentrated to provide crude sulfonamide compound 13a, also containing trace pyridine impurity. $^1$H NMR ($CDCl_3$): 4.59 (dd, J=1.2, 0.4, 1H), 4.30 (t, J=0.8, 1H), 4.02 (dd, J−=1.2, 0.4, 1H), 3.90-3.72 (m, 3H), 3.62 (dd, J=1.2, 0.8, 1H), 3.37 (m, 1H), 3.16 (m, 1H).

Compound 13a was also accessed via a similar pathway, employing thionyl chloride and subsequently oxidizing the product sulfoxide, compound 13g, to provide sulfonamide compound 13a.

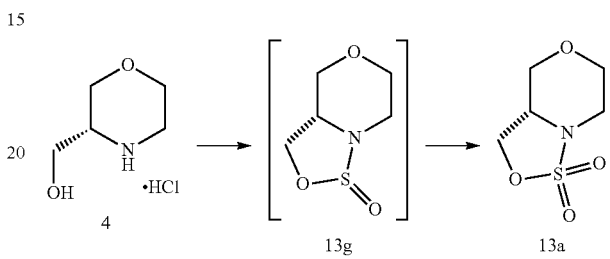

Compound 4 HCl salt (153 mg, 1 mmol, 1 eq), DCM (1.5 mL, 10 V), and TEA (0.5 mL, 4 mmol, 4 eq) were added to a vial with a pressure relief cap. The reaction mixture was then cooled to 0° C. in an ice water bath. Thionyl chloride (0.08 mL, 1.1 mml, 1.1 eq) was dissolved in 0.6 mL of DCM, then added dropwise to the reaction mixture, which was then left stirring for 1 hour at 0° C. The reaction was quenched by adding 2 mL of water, and the resulting mixture was stirred for 30 minutes. The resultant layers were then separated, and the isolated aqueous layer was extracted twice with DCM (5 mL). The combined organic layers were washed with brine (10 mL), dried with $Na_2SO_4$, and concentrated to provide crude sulfoxide compound 13g. MS: m/z 163.2 (M+H).

The provided crude sulfoxide compound 13g was then dissolved in 1.5 mL of ACN in a vial, and $RuCl_3·3H_2O$ (7.8 mg, 0.03 mmol, 3 mol %) was added. The reaction mixture was then cooled to 0° C. in an ice water bath. $NaIO_4$ (267 mg, 1.5 mmol, 1.5 eq) was dissolved in 1.5 mL of water, then was added slowly to the reaction mixture, which was then left stirring for 2 hours until reaction completion. Upon completion, the reaction was then quenched with 5 mL of DCM and stirred for 30 minutes. The resultant layers were separated, and the isolated aqueous layer was extracted twice with DCM (5 mL). The combined organic layers were washed with brine (10 mL), dried with $Na_2SO_4$, and concentrated to provide crude sulfonamide compound 13a. $^1$H NMR ($CDCl_3$): 4.59 (dd, J=1.2, 0.4, 1H), 4.30 (t, J=0.8, 1H), 4.02 (dd, J−=1.2, 0.4, 1H), 3.90-3.72 (m, 3H), 3.62 (dd, J=1.2, 0.8, 1H), 3.37 (m, 1H), 3.16 (m, 1H).

The impact of water in the production of sulfoxide compound 13g and sulfonamide compound 13a was then explored. Under the same conditions previously reported for the preparation of sulfoxide compound 13g, 1.0 equivalent of $Na_2SO_4$ was added to the reaction mixture as a drying agent. Karl Fischer analysis of the reaction mixture showed a 0.06% water content initially, with an increase in water content to 0.16% after addition of base. A Karl Fischer analysis of the reaction mixture without $Na_2SO_4$ was also taken, showing similar water content (0.06% initial, 0.15% after base addition). The addition of $Na_2SO_4$ to the reaction affected color, providing sulfoxide compound 13g as a light-yellow oil, rather than the dark red oil from the other reactions. Sulfoxide compound 13g was then isolated to see if yield of sulfonamide compound 13a improved in the next step. After silica gel chromatography, sulfoxide compound 13g was isolated. MS: m/z 163.2 (M+H). Synthesis of sulfonamide compound 13a was attempted, but no product was observed.

Finally, synthesis of sulfonamide compound 13a was telescoped to the alkylation with acetonide compound 12. The crude sulfoxide compound 13g (106 mg, crude) was oxidized to sulfonamide compound 13a, and telescoped to the alkylation with acetonide compound 12 using $Cs_2CO_3$. After 1 hour, sulfamate intermediate was not observed by GC analysis.

Finally, alternate oxidation conditions for the creation of sulfonamide compound 13a from sulfoxide compound 13g were then explored. Oxidation of sulfoxide compound 13g was attempted under two different sets of oxidative conditions on 2 mmol scale, one with mCPBA/DCM and the other with $H_2O_2$/AcOH. GCMS of the mCPBA directed oxidation showed m-chlorobenzoic acid as the main peak. GCMS for the $H_2O_2$ direct oxidation did not provide good data. The two alternate oxidation reactions were worked up, but no sulfonamide compound 13a was isolated.

Example 9: Preparation of Compounds of Formula 13

Preparation of Compound 13b and Compound 13c

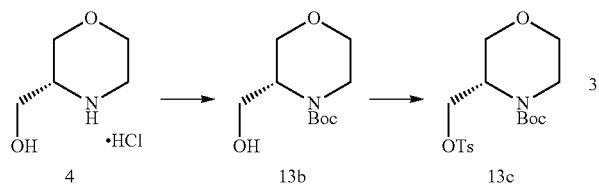

Compound 4 HCl (1.0 g, 6.5 mmol, 1 eq), DCM (20 mL, 20 V), DMAP (79 mg, 0.6 mmol, 10 mol %), and TEA (1 mL, 7.2 mmol, 1.1 eq) were added to a round bottom flask, followed by the addition of $Boc_2O$ (1.5 mL, 6.8 mmol, 1.05 eq). The reaction mixture was allowed to stir for 16 hours. The reaction mixture was then cooled to 0° C. in an ice water bath, and quenched with 11 mL of 1 M HCl. The layers were then separated, and the isolated aqueous layer was extracted twice with DCM (5 mL). The combined organic layers were then washed with saturated a $NaHCO_3$ solution (10 mL). The organic layer was then dried with $Na_2SO_4$ and concentrated. Purification of the resultant material was performed using silica gel chromatography with a solvent gradient of 0-50% EtOAc:heptane to provide Boc-protected amine compound 13b. $^1$H NMR ($CDCl_3$): 4.04 (br s, 1H), 3.96-3.75 (m, 5H), 3.61 (m, 1H), 3.52 (m, 1H), 3.21 (br s, 1H), 1.50 (s, 9H).

Activation of the alcohol of Boc-protected amine compound 13b was accomplished by synthesizing the corresponding tosylate. Crude compound 13b (7.1 g, 32.6 mmol, 1 eq), DABCO (7.3 g, 65.3 mmol, 2 eq) and EtOAc (5 mL, 5 V) were added to a round bottom flask. The reaction mixture was cooled to 0° C. in an ice water bath, then TsCl (9.3 g, 48.9 mmol, 1.5 eq) was added in small portions. The reaction was left stirring for 1 hour at 0° C., then was allowed to warm to room temperature for 3 hours until completion. The reaction mixture was quenched with water (10 mL) and the resultant layers were separated. The isolated aqueous layer was extracted twice with EtOAc (10 mL). The combined organic layers were washed with brine (20 mL), dried with $Na_2SO_4$ and concentrated. Purification was performed using silica gel chromatography with a solvent gradient of 0-100% EtOAc:heptane to provide compound 13c.

$^1$H NMR ($CDCl_3$): 7.82 (d, J=8.4, 2H), 7.38 (d, J=8.4, 2H), 4.19-4.12 (m, 4H), 3.86-3.74 (m, 3H), 3.56-3.40 (m, 2H), 2.48 (s, 3H), 1.47 (s, 9H).

Preparation of Compound 13d and Compound 13e

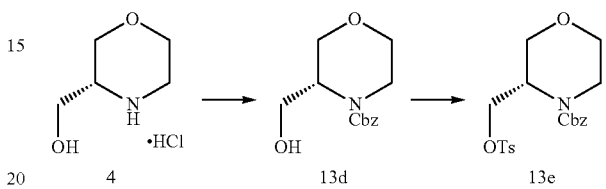

Cbz-protected amine compound 13d is prepared using methods known in the art.

Activation of the alcohol of Cbz-protected amine compound 13d was accomplished by synthesizing the corresponding tosylate. Crude compound 13d (8.2 g, 32.6 mmol, 1 eq), DABCO (7.3 g, 65.3 mmol, 2 eq), and EtOAc (5 mL, 5 V) were added to a round bottom flask. The reaction mixture was cooled to 0° C. in an ice water bath, then TsCl (9.3 g, 48.9 mmol, 1.5 eq) was added in small portions. The reaction was left stirring for 1 hour at 0° C., then was allowed to warm to room temperature for 3 hours until completion. The reaction mixture was quenched with water (10 mL) and the resultant layers were separated. The isolated aqueous layer was extracted twice with EtOAc (10 mL). The combined organic layers were washed with brine (20 mL), dried with $Na_2SO_4$ and concentrated. Purification was performed using silica gel chromatography with a solvent gradient of 0-100% EtOAc:heptane giving compound 13e.

$^1$H NMR ($CDCl_3$): 7.83-7.75 (m, 2H), 7.42-7.33 (m, 7H), 5.15 (s, 2H), 4.28-4.21 (m, 2H), 3.91-3.82 (m, 3H), 3.56-3.44 (m, 2H), 2.46 (s, 3H).

Example 10: Preparation of Compound 12

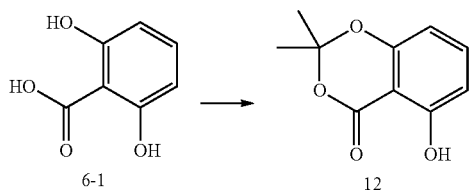

Compound 6-1 (7.7 g, 50 mmol, 1 eq), DMAP (0.3 g, 0.25 mmol, 0.5 mol %), acetone (3.7 g, 64.5 mmol, 1.3 eq), and DME (37.5 mL, 5V) were added to a three neck round bottom flask and purged with $N_2$ for 5 minutes. The reaction mixture was then cooled to 0° C. using an ice water bath. Thionyl chloride (8.4 g, 70 mmol, 1.4 eq) was then added slowly, to avoid raising the temperature more than 5° C. The reaction mixture was then left stirring to reach room temperature, and allowed to continue stirring for 16 hours. The reaction was stopped after 18 hours. Upon completion, the reaction mixture was concentrated and EtOAc (100 mL) and water (100 mL) were added, and the resulting layers were separated. The aqueous layer was extracted twice with EtOAc (100 mL). The organic layers were then combined and washed with a saturated aqueous NaHCO$_3$ solution (100 mL), then dried with Na$_2$SO$_4$ and concentrated. The resulting product was then purified using silica gel chromatography, with a solvent gradient of 0-50% EtOAc:heptane, to provide acetonide product compound 12. $^1$H NMR (CDCl$_3$): 10.4 (s, 1H), 7.44 (t, J=8.2, 1H), 6.66 (dd, J=8.4, 0.6, 1H), 6.47 (dd, J=8.0, 0.8, 1H), 1.78 (s, 6H).

Example 11: Preparation of Compound 10 and Compounds of Formula 14

Preparation of Compound 10

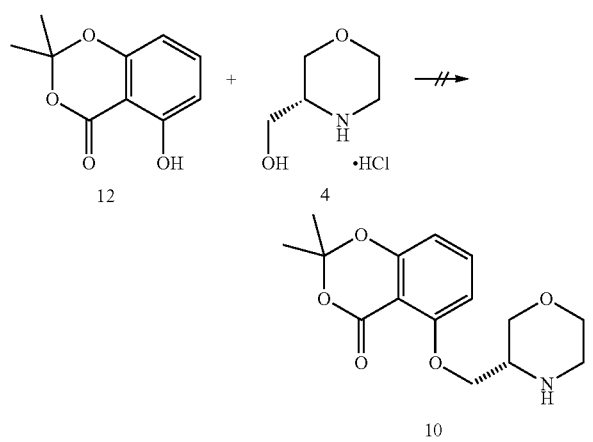

Acetonide compound 12 and compound 4 HCl salt were combined under Mitsunobu reaction conditions. Two reactions were examined, in a 0.5 mmol scale employing DIAD and PPh$_3$. One of the reactions had an additional 1.1 equivalents of TEA. The reaction mixtures were left stirring for 18 hours at room temperature and monitored by HPLC. HPLC data showed two peaks, one corresponding to acetonide compound 12 (8.7 min) and the other to triphenylphosphine oxide (7.7 min). Product compound 10 was not formed in either reaction. Preparation of Compounds of Formula 14

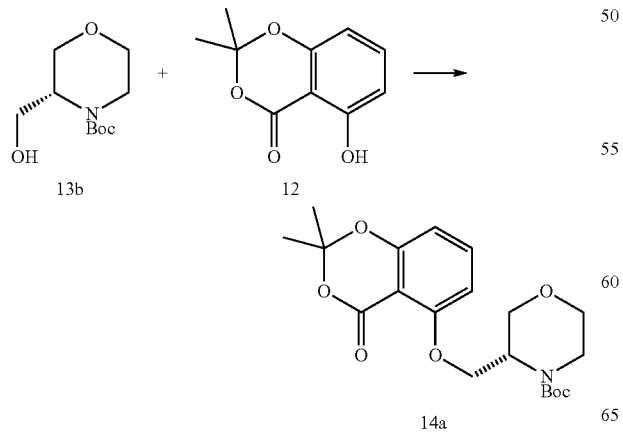

Acetonide compound 12 (167 mg, 0.9 mmol, 1.1 eq), compound 13b (170 mg, 0.78, 1.0 eq), and PPh$_3$ (225 mg, 0.9 mmol, 1.1 eq) were added to a vial with a pressure relief cap, and the vial was purged with N$_2$ for 10 minutes. THF (2 mL, 15 V) was added and the reaction mixture was cooled to 0° C. with an ice water bath. DIAD (0.17 mL, 0.9 mmol, 1.1 eq) was dissolved in 0.5 mL of THF, then added dropwise over 15 minutes. The reaction mixture was then removed from the ice bath and was then stirred at room temperature for 18 hours. The reaction was quenched with water (10 mL) and the layers were separated. The isolated aqueous layer was then extracted twice with 10 mL of EtOAc. The combined organic layers were then washed with brine (10 mL), dried with Na$_2$SO$_4$ and concentrated. Purification was performed using silica gel chromatography, with a solvent gradient of 0-100% EtOAc:heptane, to provide compound 14a.

$^1$H NMR (CDCl$_3$): 7.45 (t, J=8.4, 1H), 6.69 (d, J=8.0, 1H), 6.58 (d, J=8.0, 1H), 4.47-4.35 (m, 3H), 4.15-4.08 (m, 1H), 3.89 (m, 2H), 3.62-3.59 (m, 2H), 3.16 (br s, 1H), 1.72 (s, 6H), 1.50 (S, 9H). A byproduct corresponding to the hydrazine dicarboxylate of DIAD was also observed (1.5:1, product:DIAD).

A similar Mitsunobu reaction was performed with acetonide compound 12 and compound 13b, at a reaction temperature of 50° C. The reaction was left stirring for 24 hours and subsequent purification was similarly performed using silica gel chromatography to provide compound 14a in slightly elevated yield. However, the hydrazine dicarboxylate byproduct was also observed.

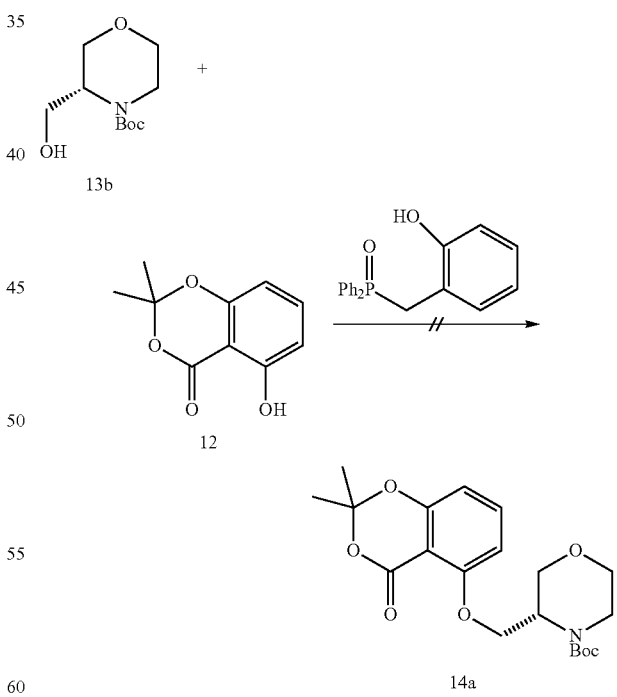

A catalytic Mitsunobu reaction was similarly investigated, using (2-hydroxybenzyl)diphenylphosphine oxide in the reaction with acetonide compound 12 and compound 13b, but no product compound 14a was observed after 48 hours under reflux.

Alternative Method 1 for Preparing Compound 10

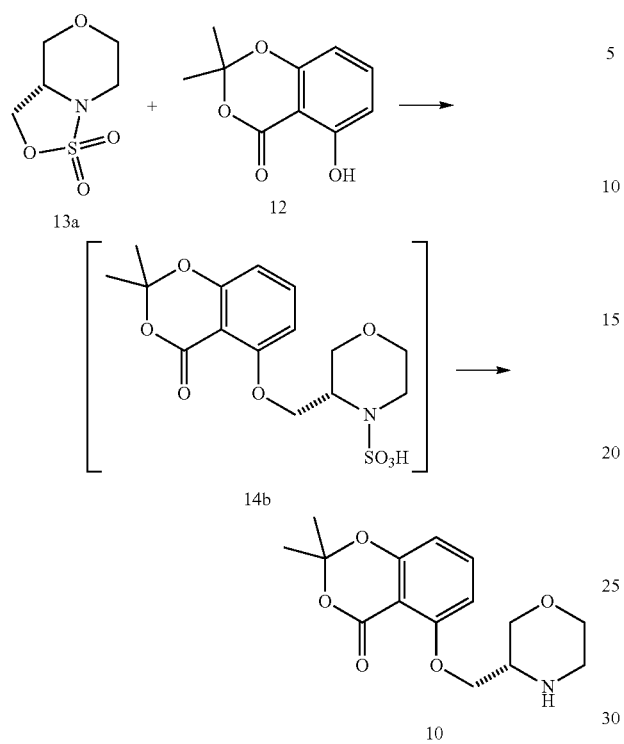

Acetonide compound 12 (103 mg, 0.5 mmol, 1 eq), DMA (0.5 mL, 5 V), and CsCO$_3$ (207 mg, 0.6 mmol, 1.2 eq) were added to a vial with a pressure relief cap. The reaction mixture was purged with N$_2$ for 5 minutes and left stirring in an ice water bath to reach 0° C. for 15 minutes. Sulfonamide compound 13a (95 mg, 0.5 mmol, 1 eq) was then dissolved in DMA (0.5 mL, 5 V) and added to the reaction mixture dropwise. The reaction mixture was then removed from the ice bath and left stirring at room temperature for 4 hours. The reaction temperature was then increased to 50° C. and left stirring for 16 hours. The reaction showed consumption of sulfonamide compound 13a by GCMS after 5 hours, but 66.1% of acetonide compound 12 was still present. Upon completion, the reaction was quenched with 5 mL of water and the resultant layers were separated. Sulfamic acid intermediate 14b went to the aqueous layer, which was then treated with 3 M HCl. Compound 10 was not isolated from this reaction.

A similar reaction was then examined, varying the base employed. Acetonide compound 12 (103 mg, 0.5 mmol, 1 eq), DMA (0.5 mL, 5 V), and NaH (25 mg, 0.6 mmol, 1.2 eq) were added to a vial with a pressure relief cap. The reaction mixture was purged with N$_2$ for 5 minutes and left stirring in an ice water bath to reach 0° C. for 15 minutes. Sulfonamide compound 13a (95 mg, 0.5 mmol, 1 eq) was then dissolved in DMA (0.5 mL, 5 V) and added to the reaction mixture dropwise. The reaction mixture was then removed from the ice bath and left stirring at room temperature for 4 hours. The reaction temperature was then increased to 50° C. and left stirring for 16 hours. Then 4 M HCl in dioxane (0.2 ml, 0.8 mmol, 1.7 eq) was added and the mixture was left stirring for 1 hour. The reaction was quenched with 5 mL of saturated Na$_2$CO$_3$ solution, and the resulting layers were separated. The isolated aqueous layer was then extracted twice with DCM (10 mL). Crude compound 10 was obtained. LC/MS: m/z 294.12 (M+H), $^1$H NMR (CDCl$_3$): 7.45 (m, 1H), 6.58 (d, J=8.4, 2H), 4.13-4.10 (m, 1H), 3.95-3.84 (m, 3H), 3.62-3.38 (m, 3H), 3.38-2.96 (m, 5H), 1.73 (s, 6H).

Alternative Method 2 for Preparing Compound 10

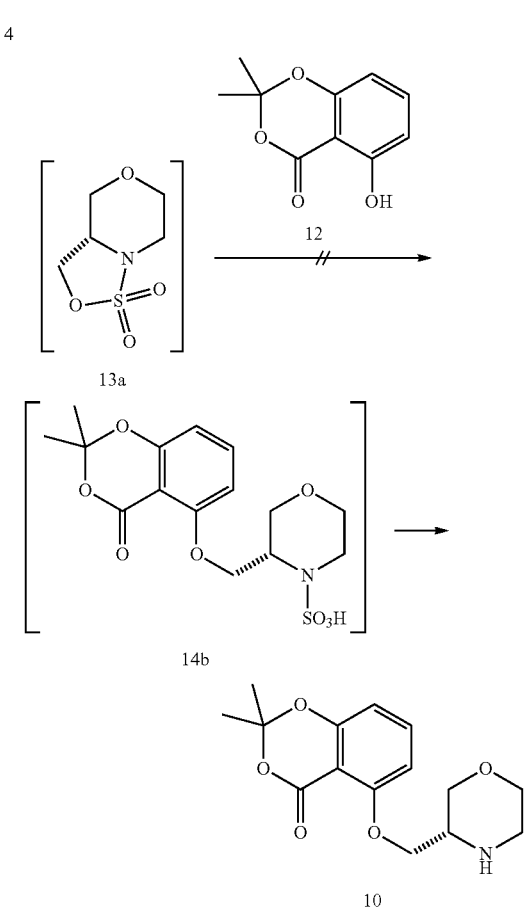

The synthesis of sulfonamide compound 13a was performed as previously reported, and used in a telescoped fashion in the subsequent alkylation. The alkylation sulfamate intermediate 14b was not observed after 18 hours at 50° C.

Alternative Method 3 for Preparing Compound 10

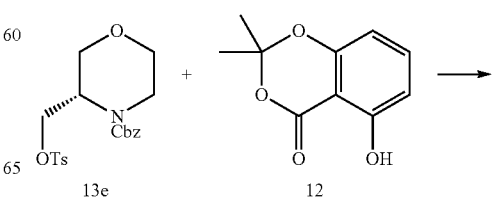

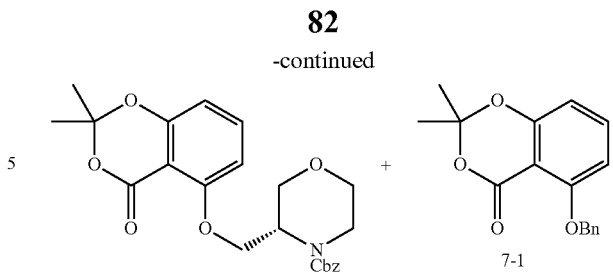

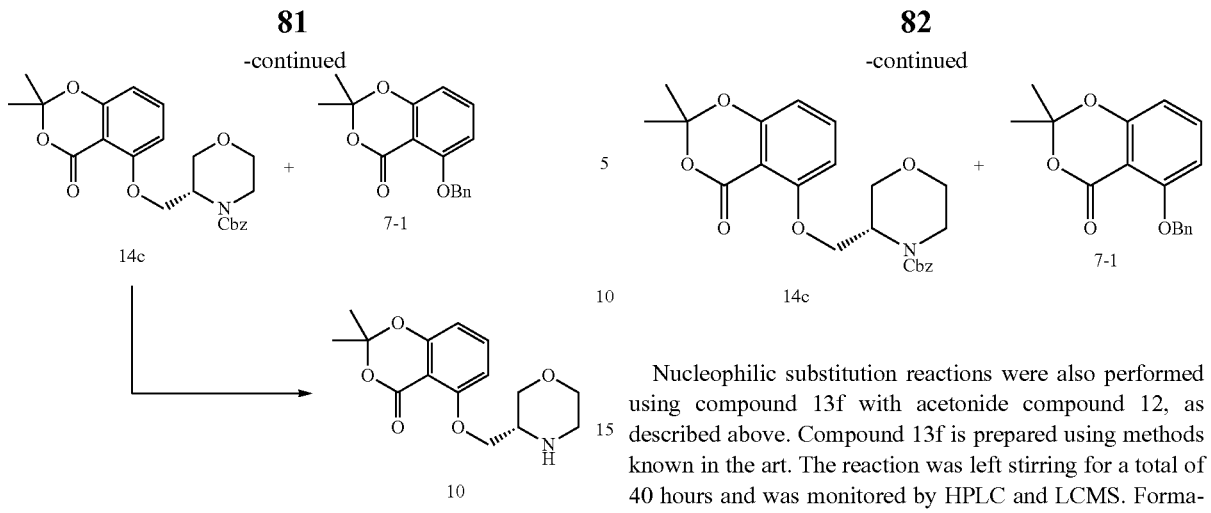

In a three-neck round bottom flask with a reflux condenser attached, acetonide compound 12 (2 g, 10.3 mmol, 1.5 eq), K$_2$CO$_3$ (1.9 g, 13.7 mmol, 2 eq), and MeTHF (10 mL, 5 V) were added and the mixture was purged with N$_2$ for 5 minutes. Compound 13e was then added, and the resulting reaction mixture was set to reflux at 80° C., and left stirring for 18 hours. Complete consumption of the tosylate material was observed after 18 hours. The reaction mixture was then cooled to room temperature and quenched with water (10 mL). EtOAc (10 mL) was also added. The resulting layers were separated, and the isolated aqueous layer was extracted twice with EtOAc (10 mL). The combined organic layers were washed with brine (20 mL), dried with Na$_2$SO$_4$ and concentrated to provide crude compound 14c, as well as a benzyl ether byproduct, compound 7-1, which was observed by LCMS and $^1$H NMR. Purification of the crude material was performed using silica gel chromatography with a solvent gradient of 0-100% EtOAc:heptane to provide compound 14c. LC/MS: m/z 449.97 (M+Na).

Compound 14c (600 mg, 1.4 mmol, 1 eq) was then added to a round bottom flask with EtOH (5 mL, 10 V), 5% Pd/C (100 mg), and H$_2$ balloon attached. The reaction was left stirring for 20 hours, then was filtered through a celite plug. The celite plug was then rinsed with 20 mL of EtOH and the filtrate was concentrated, providing compound 10. LC/MS: m/z 294.12 (M+H), $^1$H NMR (CDCl$_3$): 7.45 (m, 1H), 6.58 (d, J=8.4, 2H), 4.13-4.10 (m, 1H), 3.95-3.84 (m, 3H), 3.62-3.38 (m, 3H), 3.38-2.96 (m, 5H), 1.73 (s, 6H).

Alternative Method 4 for Preparing Compound 10

Other activating groups for the alkylation of protected derivatives of compound 4 with acetonide compound 12 were also examined to access compound 10.

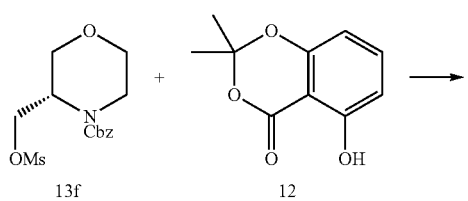

Nucleophilic substitution reactions were also performed using compound 13f with acetonide compound 12, as described above. Compound 13f is prepared using methods known in the art. The reaction was left stirring for a total of 40 hours and was monitored by HPLC and LCMS. Formation of product compound 14c (LC/MS: m/z 449.97 (M+Na)) and byproduct compound 7-1, in a ratio of 1:1.3 (product:byproduct), was observed.

Alternative Method 5 for Preparing Compound 10

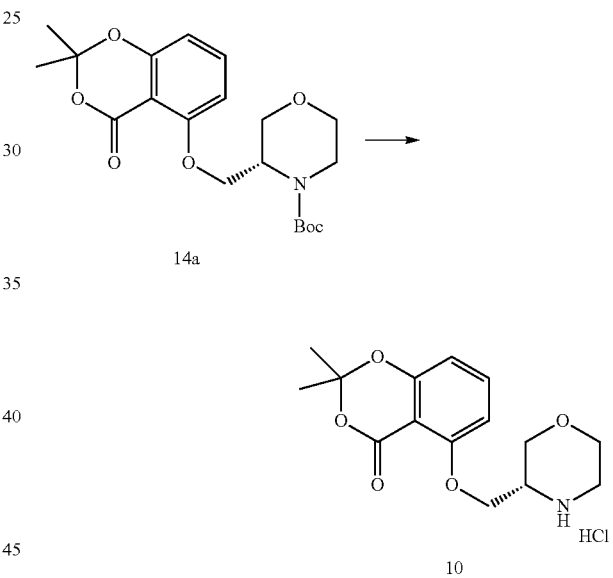

A 50 mL round bottom flask was charged with Compound 14a (1.70 g, 4.32 mmol, 1.0 equiv.). Dichloromethane (17 mL, 10 vol.) was added, and the resulting solution was cooled to 0° C. under N$_2$. HCl in dioxane (3.24 mL, 13.0 mmol, 3.0 equiv., 4 M) was added dropwise, and then the reaction was gradually warmed to ambient temperature. Samples were taken for HPLC at various times. An additional 0.3 equiv of HCl was added at 3.5 h, and the reaction was allowed to stir overnight. Compound 14a was observed to be fully consumed by HPLC. The solvent was removed in vacuo, providing crude Compound 10 as the HCl salt. MTBE (40 mL) was added to remove the reduced DIAD impurity present from the preparation of Compound 14a. The solid was filtered and washed with MTBE (20 mL). Drying in vacuo provided Compound 10 as the HCl salt. XRD: 2Theta (°) 7.5, 11.5, 13.0, 14.9, 16.5, 17.3, 19.7, 22.5, 24.0, 25.2, 25.8, 27.6, 30.2.

Example 12: Preparation of Compounds of Formula 11

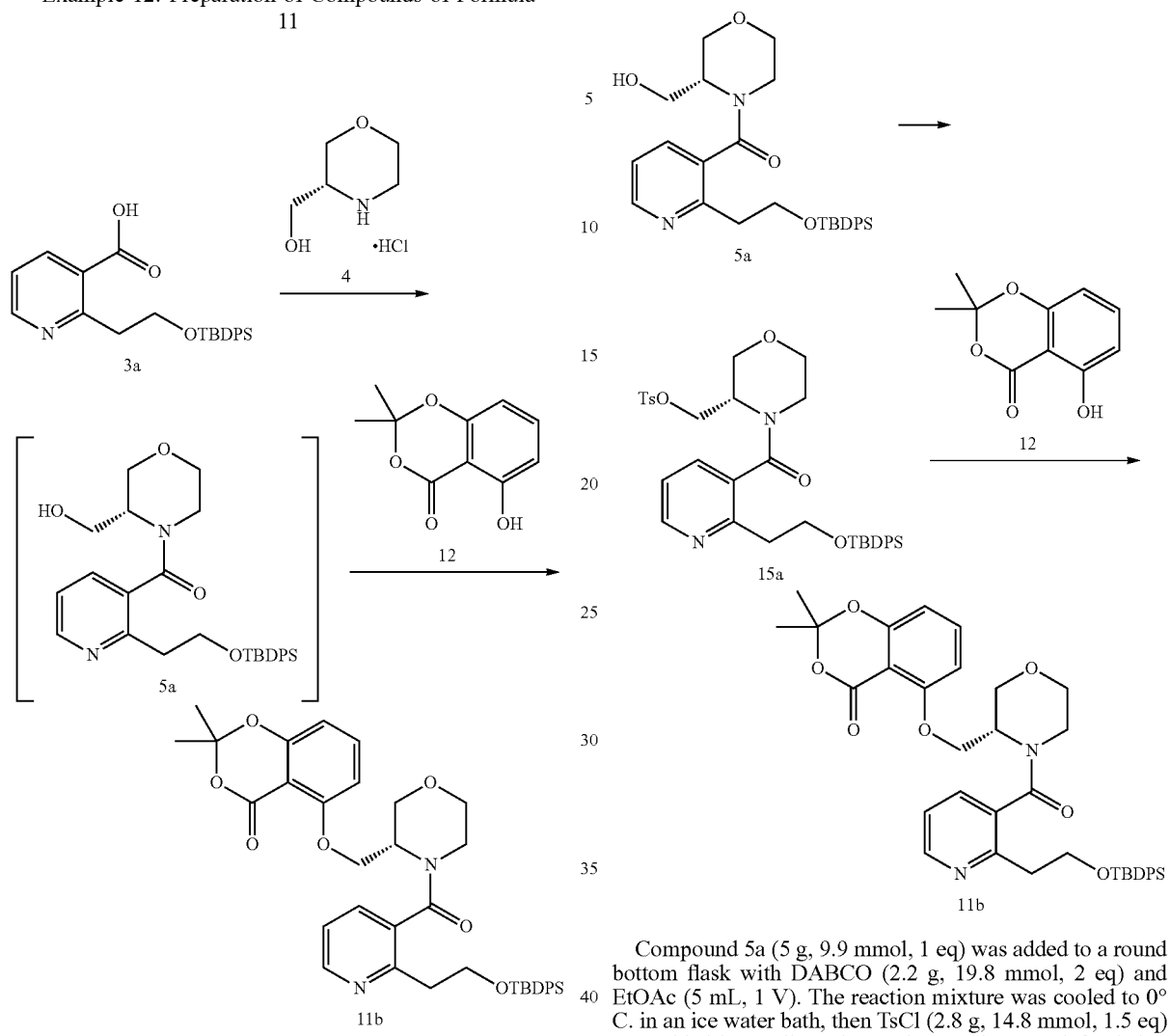

Compound 5a was prepared according to methods previously described herein.

Acetonide compound 12 (423 mg, 2.2 mmol, 1.1 eq), compound 5a (1 g, 2 mmol, 1 eq), and PPh$_3$ (572 mg, 2.2 mmol, 1.1 eq) were added to a round bottom flask and the mixture was purged with N$_2$ for 10 minutes. THF (10 mL, 10 V) was then added and the reaction mixture was cooled to 0° C. in an ice water bath. DIAD (0.4 mL, 2.2 mmol, 1.1 eq) was then dissolved in 5 mL of THF and added dropwise to the reaction mixture over 15 minutes. The reaction was removed from the ice bath and left stirring at room temperature for 18 hours. Upon completion, the reaction was quenched with water (20 mL) and resulting layers were separated. The isolated aqueous layer was extracted twice with 10 mL of EtOAc. The combined organic layers were then washed with brine (10 mL), dried with Na$_2$SO$_4$ and concentrated. Purification of the resulting material was performed using silica gel chromatography with a solvent gradient of 0-100% EtOAc:heptane to provide compound 11b (LC/MS: m/z 681.11 (M+H)), with an impurity of triphenylphosphine oxide also observed.

Alkylation of acetonide compound 12 with an activated derivative of compound 5a was also examined to access compound 11b.

Compound 5a (5 g, 9.9 mmol, 1 eq) was added to a round bottom flask with DABCO (2.2 g, 19.8 mmol, 2 eq) and EtOAc (5 mL, 1 V). The reaction mixture was cooled to 0° C. in an ice water bath, then TsCl (2.8 g, 14.8 mmol, 1.5 eq) was added in small portions. The reaction was left stirring for 1 hour at 0° C., then was allowed to warm to room temperature for 3 hours until completion. The reaction was then quenched with water (10 mL) and resulting layers were separated. The isolated aqueous layer was then extracted twice with EtOAc (10 mL). The combined organic layers were washed with brine (20 mL), dried with Na$_2$SO$_4$ and concentrated. Purification of the obtained material was performed using silica gel chromatography with a solvent gradient of 0-100% EtOAc:heptane to provide compound 15a.

In a three-neck round bottom flask with a reflux condenser attached, acetonide compound 12 (1.2 g, 6 mmol, 2 eq), K$_2$CO$_3$ (870 mg, 6.3 mmol, 2.1 eq), and MeTHF (20 mL, 10 V) were added and purged with N$_2$ for 5 minutes. Tosylate compound 15a (2 g, 3 mmol, 1 eq) was then added, and then reaction temperature was set to reflux at 80° C., and left stirring for 18 hours. The reaction mixture was then allowed to cool to room temperature and was quenched with water (10 mL). The resulting layers were separated and the isolated aqueous layer was extracted three times with EtOAc (10 mL). The combined organic layers were washed with brine (20 mL), dried with Na$_2$SO$_4$ and concentrated. Purification of the resulting material was performed using silica gel chromatography with a solvent gradient of 0-100% EtOAc:heptane to give compound 11b. LC/MS: m/z 681.17 (M+H). Compound 5a was also observed and isolated as a byproduct.

Next, the amide coupling of compound 10 and compound 3a was explored for the formation of compound 11b.

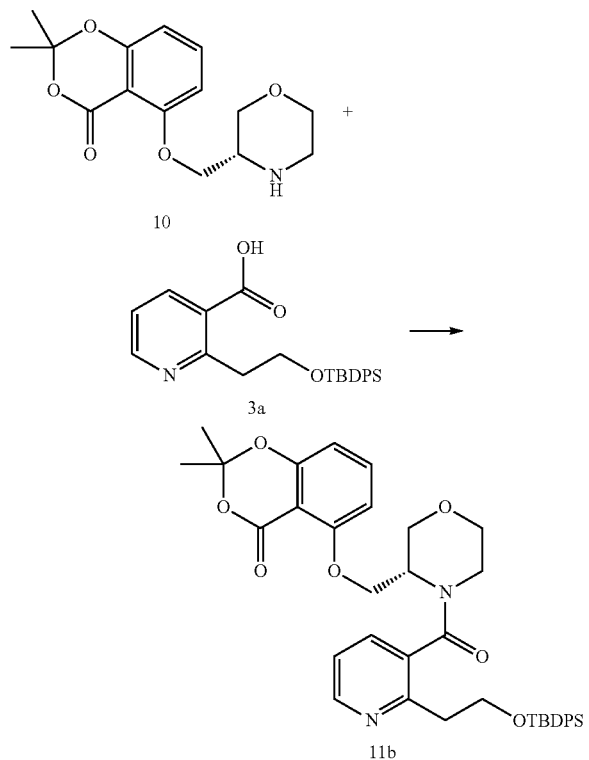

Compound 10 (190 mg, 0.6 mmol, 1 eq) was added to a vial with a pressure relief cap with compound 3a (311 mg, 0.8 mmol, 1.2 eq) and DMF (1 mL, 5 V). The reaction mixture was then cooled to 0° C. in an ice water bath. HBTU (291 mg, 0.8 mmol, 1.2 eq) was then added, followed by the addition of DIEA (0.44 mL, 2.5 mmol, 4 eq). The reaction was then allowed to warm to room temperature and was left stirring for 18 hours. The reaction proceeded to completion after 4 hours. The reaction was then quenched with water (10 mL) and resulting layers were separated. The isolated aqueous layer was extracted three times with EtOAc (10 mL). The combined organic layers were washed with brine (10 mL), dried with $Na_2SO_4$ and concentrated. Purification of the resulting material was performed using silica gel chromatography with a solvent gradient of 0-100% EtOAc:heptane, to provide compound 11b. LC/MS: m/z 681.17 (M+H).

Example 13: Preparation of Compound 7a

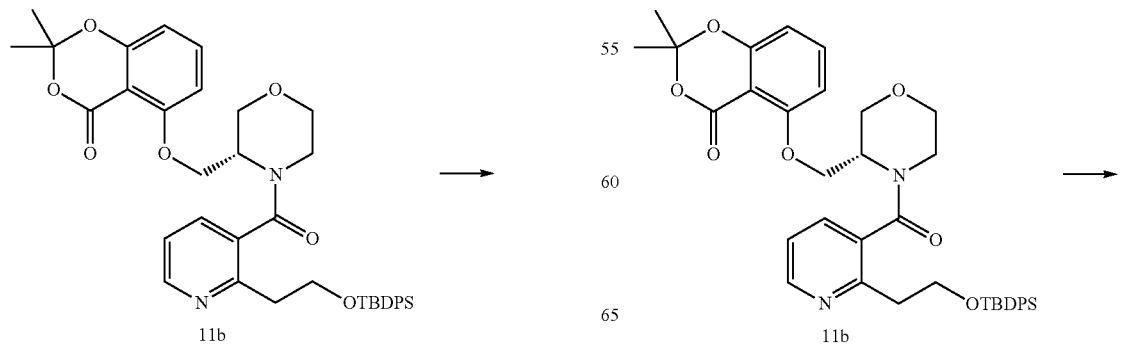

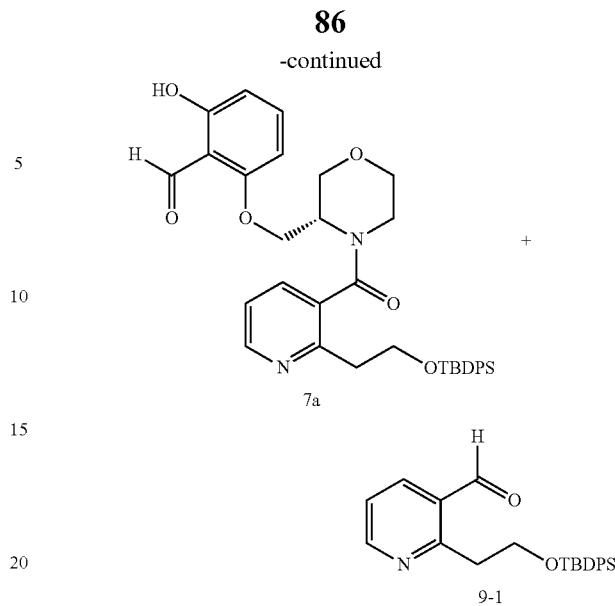

Compound 11b (500 mg, 0.7 mmol, 1 eq) was added to a vial with a pressure relief cap with DCM (5 mL, 10 V), and resulting mixture was purged with $N_2$ for 5 minutes. The reaction mixture was cooled to −78° C. in a dry ice acetone bath. DIBAL-H (1M in DCM, 2.2 mL, 2.2 mmol, 3 eq) was then added dropwise, with gas evolution observed, and the reaction was left stirring at −78° C. for one hour until completion. The reaction was then quenched with 1 M of HCl (5 mL) and allowed to warm to room temperature. EtOAc (10 mL) was added and resulting layers were separated. The isolated aqueous layer was extracted twice with EtOAc (10 mL). The combined organic layers were washed with brine (10 mL), dried with $Na_2SO_4$ and concentrated. Purification of the resulting material was performed using silica gel chromatography with a solvent gradient of 0-100% EtOAc:heptane to obtain compound 7a (LC/MS: m/z 625.09 (M+H)), with an observed byproduct of aldehyde compound 9-1.

Alternatively, the reduction of compound 11b was also performed using 1.0 equivalent of DIBAL-H, under the same reaction conditions reported above. The reaction stalled after 4 hours at −78° C. The reaction was left overnight and allowed to reach room temperature, providing only a small amount of product compound 7a. LC/MS: m/z 625.09 (M+H). No workup or purification was performed for this reaction.

87
-continued

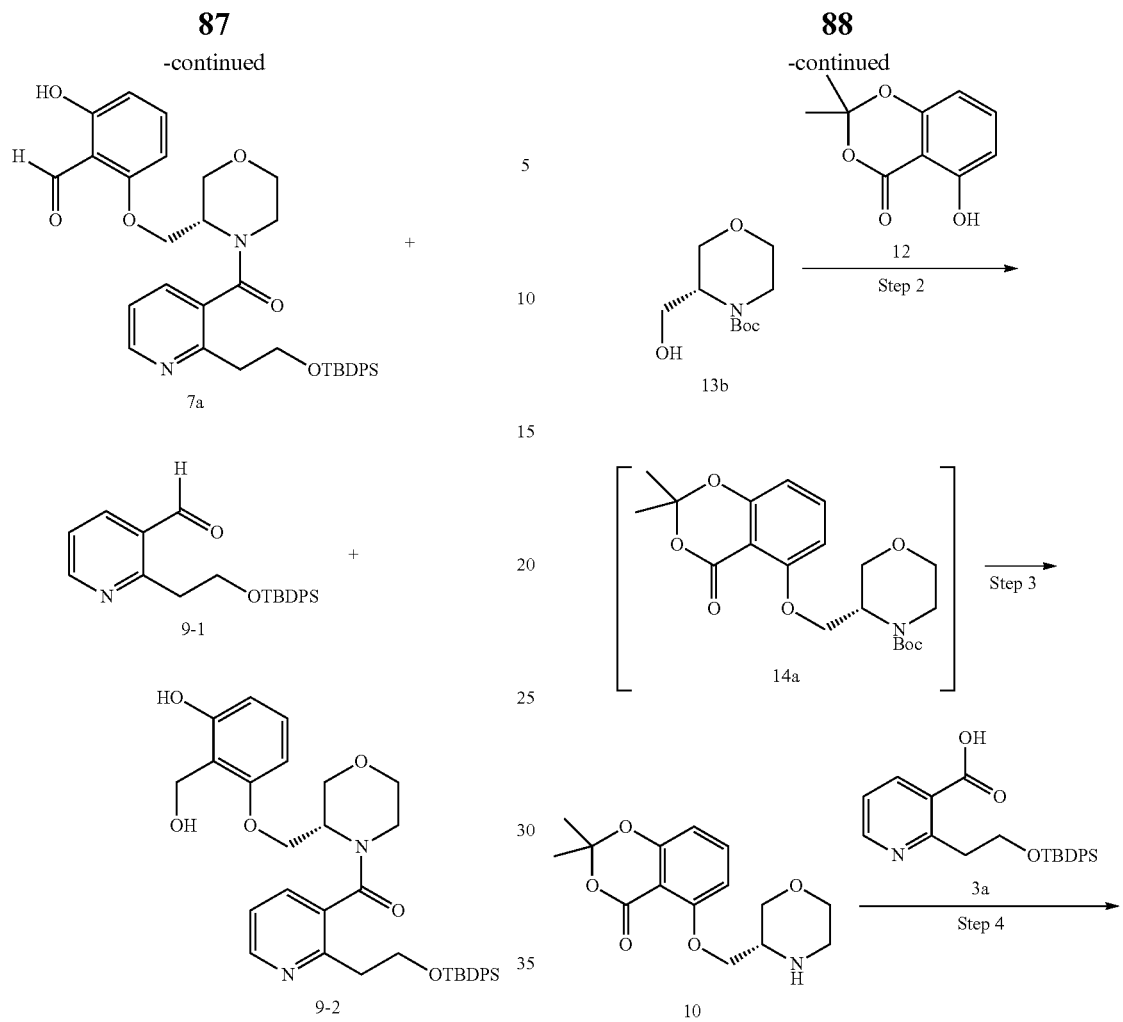

Similarly, the reduction of compound 11b was also performed using 2.0 equivalents of DIBAL-H, under the same reaction conditions described above. The reaction showed completion after 1 hour. Similar reactivity was observed as when 3.0 eq of DIBAL-H was used. LCMS showed the presence of the desired product compound 7a (LC/MS: m/z 625.09 (M+H)), as well as byproducts aldehyde compound 9-1 and benzyl alcohol compound 9-2. Purification was not performed.

Example 14: Alternate Preparation Method 4 for Compound I

Preparation of Compound I via Compound 10

88
-continued

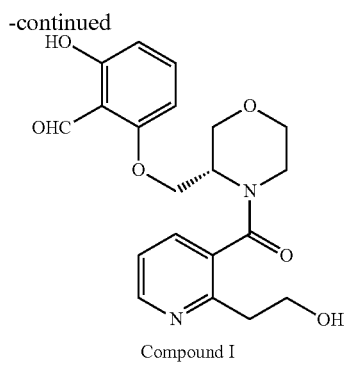

Compound I

Step 1: Preparation of Compound 13b

Compound 4 HCl (100.0 g, 1.0 equiv), DCM (9 V, 900 mL), and Et$_3$N (138.3 g, 2.1 equiv) were charged to a reactor. The reactor contents were cooled to −2 to 2° C. A solution of Boc-anhydride (149.2 g, 1.05 equiv) in DCM (100 mL, 1V) at 10° C. was transferred into the reactor over ~0.5 h. Following the Boc-anhydride addition, the reactor contents were adjusted to approximately 25° C. and agitated for 3 hours. Water (200 mL, 2V) was then charged to the reactor, and the resulting mixture was agitated at 20 to 25° C. for 0.5 h. The phases were separated and the organic layer was washed with water (200 mL, 2 V). MgSO$_4$ (100.0 g, 1 S) was charged to the organic layer, and the resulting slurry filtered to remove solids. After washing the solids with DCM (200 mL, 2V), the combined organics were concentrated under reduced pressure to approximately 2-3 V. Heptane (300 mL, 3V) was charged to the DCM solution, and the resulting mixture was concentrated under reduced pressure to approximately 3-5 V, resulting in a slurry. Heptane (300 mL, 3 V) was again charged to the slurry and the contents were again concentrated under reduced pressure to approximately 3-5 V. Heptane (250 mL, 2.5 V) was once again charged to the slurry, and the resulting mixture was agitated at 20 to 25° C. for 1 h. The slurry was filtered and the wet cake was washed with heptane (200 mL, 2V). The wet cake was dried under vacuum at ambient temperature for 18 h, affording Compound 13b. $^1$H NMR (400 Mz, CDCl$_3$) δ 4.01-3.91 (m, 2H), 3.83 (m, 3H), 3.78-3.70 (m, 1H), 3.56 (dd, J=11.9, 3.5 Hz, 1H), 3.46 (ddd, J=12.2, 11.4, 3.1 Hz, 1H), 3.16 (t, J=12.9 Hz, 1H), 2.46 (s, 1H), 1.47 (s, 9H). $^{13}$C NMR (100 Mz, CDCl$_3$) δ 155.7, 80.6, 66.8, 66.5, 60.4, 52.4, 40.3, 28.5. LC/MS: m/z 118.1 (M-Boc+H).

Step 2 and 3: Preparation of Compound 14a and 10

A 1 L round bottom flask (RBF) was charged with 2-MeTHF (500 mL), Compound 12 (51.33 g, 97.4 wt %=50.0 assay g, 0.257 mol, 1.0 equiv), Compound 13b (69.64 g, 96.4 wt %=67.13 assay g, 0.309 mol, 1.2 equiv), and PPh$_3$ (87.79 g, 0.335 mmol, 1.3 equiv) under a nitrogen atmosphere. The resulting solution was cooled in an acetone/ice bath to −2° C. DIAD (65.9 mL, 0.335 mmol, 1.3 equiv) was charged to the mixture dropwise over 35 min, maintaining a temperature <2° C. The reaction was stirred for 15 min, then warmed to ambient temperature over 45 min and stirred overnight. At 17 h, solids were observed. The batch was warmed to 30° C. to dissolve all solids and the reaction was sampled for HPLC. Upon completion, the crude reaction mixture was warmed to 50° C. and MSA (66.2 mL, 1.02 mmol, 4.0 equiv relative to Compound 14a) was added dropwise over 1.5 h, maintaining a temperature<52° C. The reaction was heated at 50° C. for 4 h, then cooled to ambient temperature overnight. The resultant solid was collected by filtration and washed with 2-MeTHF (100 mL then 50 mL, displacement washes). The solid was dried on the funnel under a nitrogen atmosphere for 2 h to obtain Compound 10 as a MSA salt. XRD: 2Theta (°) 11.5, 13.0, 13.5, 15.4, 16.3, 17.5, 18.2, 20.2, 20.7, 21.5, 22.7, 23.1, 24.5, 25.2, 27.2.

Compound 10 as a MSA salt was then suspended in IPAc (1.0 L) and cooled in an ice bath. Aq. K$_2$HPO$_4$ (600 mL) was added while maintaining a temperature<5° C. until the pH of aq=8.2, however, solid remained undissolved. H$_2$O (150 mL) was added to dissolve all the solid (pH=7.7). Additional aq. K$_2$HPO$_4$ (50 mL) was added (pH=8.0). The batch was warmed to ambient temperature and the organic layer was removed. The aqueous was extracted with additional IPAc (500 mL). The combined organics were dried over Na$_2$SO$_4$ and filtered. The combined organics were concentrated under reduced pressure on the rotary evaporator (bath temp—35° C.) to 350 mL. The batch was removed from the rotary evaporator and upon cooling, crystallization was observed. With stirring, heptane (250 mL) was added via addition funnel and the resulting suspension was aged for 1 h. The batch was concentrated on the rotary evaporator to ~350 mL. This was repeated with additional heptane (250 mL). After concentrating to ~350 mL, the batch was aged overnight at ambient temperature. The solid was filtered (fast filtration) and washed with 100 mL cold IPAc/heptane (1:1, displacement wash). GC-HS of liquor, ratio of IPAc/heptane=26:74. The solid Compound 10 was dried on the funnel under a nitrogen atmosphere. $^1$H NMR (400 MHz, CDCl$_3$) δ 7.40 (t, J=8.3 Hz, 1H), 6.54 (d, J=8.3 Hz, 2H), 4.06 (dd, J=8.8, 3.8 Hz, 1H), 3.91-3.83 (m, 2H), 3.80 (dt, J=11.2, 2.9 Hz, 1H), 3.56 (ddd, J=11.2, 9.9, 3.2 Hz, 1H), 3.45 (dd, J=10.8, 9.4 Hz, 1H), 3.33-3.27 (m, 1H), 3.06-2.89 (m, 2H), 2.80 (bs, 1H), 1.68 (d, J=2.4 Hz, 7H). $^{13}$C NMR (100 MHz, CDCl$_3$) δ 160.4, 158.0, 157.5, 136.3, 109.4, 106.4, 105.2, 103.3, 69.4, 68.6, 67.6, 53.3, 45.0, 25.7, 25.2. LC/MS: m/z 294.2 (M+H). Compound 10 as free base: DCS: endotherm at 107.7° C. XRD: 2Theta (°) 8.2, 15.5, 16.4, 16.7, 18.0, 19.4, 20.3, 22.3, 22.8, 25.1, 26.8, 29.9.

Step 4: Preparation of Compound 11b

A solution of Et$_3$N (20.4 mL) in EtOAc (19.7 mL) was added dropwise to a suspension of compound 3a (28.3 g) and compound 10 (19.5 g, 1.0 equiv) in EtOAc (196.7 mL) at approximately 0° C. T3P (>50 wt % in EtOAc, 59.3 mL) was then added dropwise over 20 min, maintaining temperature<3° C. The reaction was stirred at approximately 0° C. for 30 min, then warmed to ambient temperature and stirred for 1 h. The reaction mixture was cooled to approximately 0° C. and water charged (200 mL). After mixing, the layers were separated. The aqueous layer was extracted with EtOAc (50 mL) and the combined organic layers were then washed with sat. NaHCO$_3$ (150 mL), then brine (150 mL). The organic stream was dried over Na$_2$SO$_4$, filtered, and concentrated to afford compound 11b. To remove the remaining EtOAc, compound 11b was dissolved in THF (50 mL, anhydrous) and again concentrated to afford compound 11b (44.09 g). LC/MS m/z 681.4 (M+H).

Step 5: Preparation of Compound 7a

Compound 11b (10.0 g, 91.9 wt % qNMR, 13.5 mmol, 1.0 equiv.) was dissolved in anhydrous THF (135 mL, 13.5 V) and cooled to −50° C. under N$_2$. Lithium diisobutyl-tert-butoxyaluminum hydride (LDBBA) (44.3 mL, 21.6 mmol, 1.6 equiv.) was added dropwise with an addition funnel over 1.2 h (temperature maintained below −45° C.). Upon completion of addition, the reaction was quenched at −45° C. with the addition of methanol (4 mL, added dropwise). The solution gradually warmed to ambient temperature and was sampled for an HPLC solution assay. Sat. aqueous Rochelle salt (100 mL) was added to the solution, followed by IPAc (100 mL). The cloudy mixture was stirred vigorously overnight (~16 h), then was transferred to a separatory funnel. The layers were separated and the aqueous layer was reextracted with IPAc (50 mL). The combined organic layers were then washed with brine (150 mL), dried over $Na_2SO_4$, filtered, and concentrated to dryness in vacuo, providing Compound 7a. LC/MS m/z 625.3 (M+H).

Step 6: Preparation of Compound I

A solution of crude Compound 7a (35.2 assay g, 56.3 mmol, 1.0 equiv.) in anhydrous THF (440 mL, 12.5 V) was charged to a three-neck 1 L RBF with overhead stirring, thermocouple, and addition funnel under $N_2$. In a separate flask, buffered TBAF was prepared by adding glacial AcOH (3.30 mL 57.7 mmol, 1.025 equiv.) dropwise over 20 min into a stirring solution of TBAF (57.7 mL, 57.7 mmol, 1.025 equiv., 1.0 M in THF) maintaining $T_{internal}$=0-5° C. under $N_2$. The buffered TBAF was charged dropwise over 15 min to the solution of Compound 7a maintaining $T_{internal}$=0-5° C., then the reaction was warmed to ambient temperature and allowed to stir overnight. At 18 h, the reaction was sampled by HPLC, and it was determined that the starting material was fully consumed. The reaction mixture was concentrated to 4.5 V by removal of solvent in vacuo at 30-35° C. The reaction was quenched by dropwise addition of aq. 0.1 M AcOH (350 mL, 10 V) over 2 h maintaining $T_{internal}$=0-5° C. Heptane (350 mL, 10 v) was added, and the mixture was stirred for 1 h at ambient temperature. The layers were partitioned, and the aqueous layer was washed with heptane twice (2×175 mL, 2×5 V). DCM (350 mL, 10 V) was added to the aqueous layer, and the mixture was cooled to 0-5° C. Solid $K_2CO_3$ was added portion-wise with mixing to reach pH=7.5. The layers were partitioned, and the organic layer was washed with water (350 mL, 10 V). The organic layer was collected and washed again with water (350 mL, 10 V). The organic layer was collected and washed a third time with water (350 mL, 10 V). The organic layer was dried over $Na_2SO_4$ overnight at 5° C., then filtered and washed with DCM (35 mL, 1 V), to afford crude Compound I as a solution in DCM (21 assay g, 54.3 mmol).

A solution of crude Compound I (4.5 g) in DCM (100 mL) was concentrated to dryness under reduced pressure, then dissolved in acetone (100 mL), and concentrated again to dryness. After 2 additional evaporations from acetone (100 mL each), the solid residue was dissolved in acetone/MTBE, 50/50 (27 mL, 6 V), at 50° C. The batch was then cooled to 30° C. over 30 minutes and seeded with Compound I Form I (5 wt %) and aged 5 hours, during which time the batch was sonicated periodically. The batch was then cooled from 30° C. to 5° C. over 4 hours, then aged for 2 hours. MTBE (18 mL, 4V) was added over 8 hours. The batch was cooled from 5 to 0° C. over 30 minutes, then aged at 0° C. for 6 hours. The solids were filtered, and the cake washed with MTBE (4V, 18 mL). After drying under vacuum, Compound I was obtained as Form I by XRPD.

Example 15: Alternate Preparation Method 5 for Compound I

Preparation of Compound I via Compound 11d

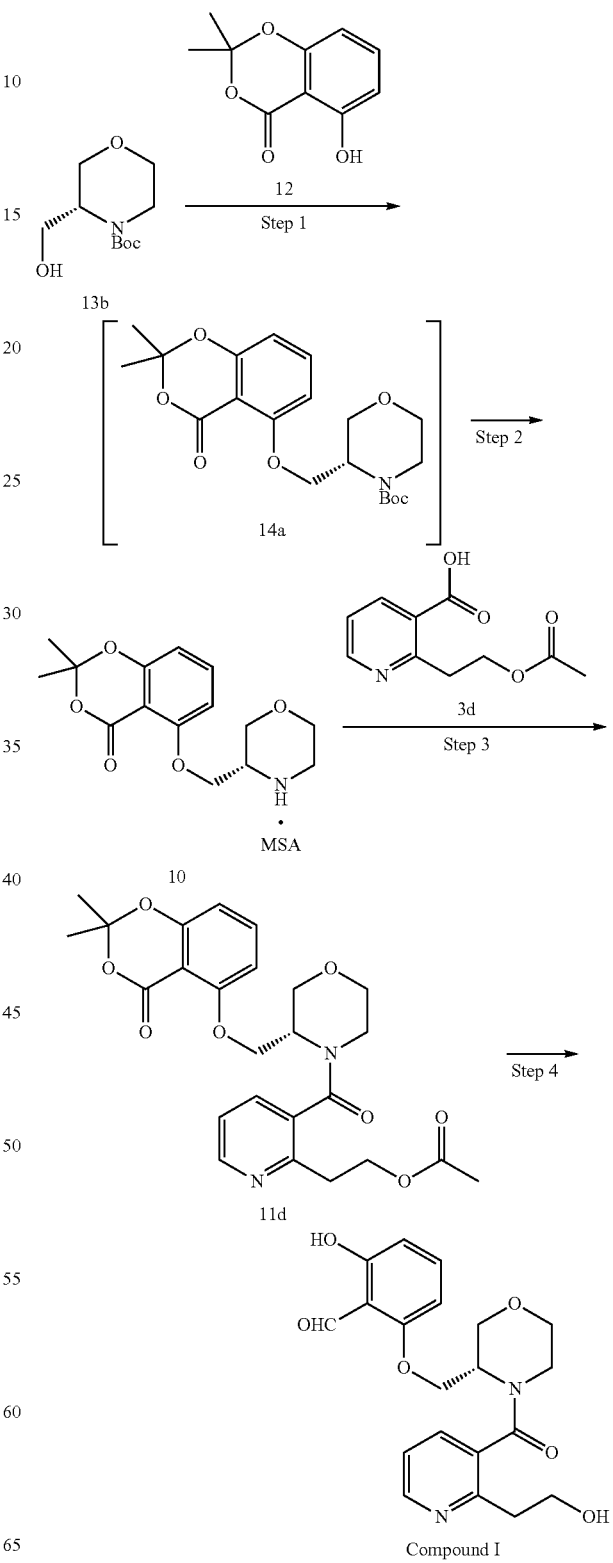

Step 1 and 2: Preparation of Compound 14a and 10
Compounds 14a and 10 were synthesized according to methods described herein.

Step 3-1: Alternate Preparation of Compound 11d
Compound 10 MSA salt (0.2 g, 1.0 equiv), Compound 3d (0.11 g, 1.05 eq.), and EtOAc (20.0 mL, 10 V) were charged to a reactor. The contents were cooled to 0 to 5° C., and $Et_3N$ (0.17 g, 0.23 mL, 3.2 eq.) was charged over 10 minutes. Then a solution of 50% T3P in EtOAc (0.49 g, 0.46 mL, 1.5 eq.) was charged to the reactor over 30 minutes at no more than 5° C. The reaction mixture was adjusted to ambient temperature (ca. 19° C.) and then agitated overnight.

The reaction mixture was cooled to 2.5° C. and then quenched with 100.0 mL (10 V) of $H_2O$. The temperature of the reaction mixture was then adjusted to 20 to 25° C., agitated, and then the phases were separated. The aqueous phase was extracted with 50.0 mL (5 V) of EtOAc. The combined organic layer was washed with 100.0 mL (10 V) of 8% aq. $NaHCO_3$, followed by 100.0 mL (10 V) of 20% aq. NaCl. The combined organic layer was then dried over 5.0 g (0.5 S) of anhydrous $Na_2SO_4$. The solids were filtered and then washed with 20.0 mL (2 V) of EtOAc. The solution was concentrated to afford crude Compound 11d. Crude Compound 11d in EtOH (5V) was allowed to evaporate over 48 h to obtain Compound 11d seed crystals.

Alternate Step 3-2: Alternate Preparation of Compound lid
DIPEA (2.0 g, 2.6 mL, 3 Eq, 15 mmol) was added to a vial containing HBTU (2.0 g, 1.05 Eq, 5.3 mmol), Compound 10 (1.5 g, 99% wt, 1 Eq, 5.1 mmol), and Compound 3d (1.1 g, 99% wt, 1 Eq, 5.1 mmol) in DMF (10 mL). The reaction mixture was stirred at rt for 20 h. After completion, $H_2O$ (50 mL) and DCM (25 mL) were added, and the phases separated. The organic layer was separated and the aqueous phase was washed with DCM (2×25 mL). The combined organic phases were dried over anhydrous $Na_2SO_4$, filtered, and concentrated. The crude was purified by column chromatography (silica gel 40 g, 0-20% MeOH in DCM) to afford Compound 11d. LC/MS: m/z 485.1 (M+H).

Procedure for crystallization of Compound 11d: A solution of Compound 11d (2 g) in EtOH (2 V) was heated to 55 to 60° C. To the solution was charged water (6V) and seed crystal (1 wt % crystalline Compound 11d), which was prepared according to methods described herein. After stirring 1 hour at 55 to 60° C., the mixture was cooled to 40 to 45° C. and stirred for 2 hours. The mixture was then cooled to 20 to 25° C. and stirred overnight. The resulting slurry was filtered and dried to afford crystalline Compound 11d Form I. DSC: endotherms observed at: 121.0° C., 201.5° C. XRD: 2Theta (°) 7.2, 10.8, 11.9, 12.9, 14.5, 15.5, 16.0, 18.2, 19.0, 19.5, 20.2, 21.1, 22.0, 24.6, 25.0, 25.5, 26.9, 29.4, 31.8.

Step 4: Preparation of Compound I
To a 250 mL jacketed reactor equipped with overhead agitation, a thermocouple, a reflux condenser and a nitrogen gas inlet was charged Compound 11d (1.0 equiv.) and tetrahydrofuran (15 V). The resulting solution was agitated at room temperature until all solids dissolved. At that time, the solution was cooled to about −10° C. before charging lithium diisobutyl-tert-butoxyaluminum hydride (LDBBA, 3.0 equiv.) and lithium tert-butoxide (1.0 equiv.) dropwise to the solution. The resulting mixture was agitated at about −10 C for approximately 1 hour before charging isopropyl acetate (10 V) and a 1.0 M aqueous solution of Rochelle's salt (10 V). Then, the mixture was agitated overnight at room temperature before splitting the two resulting layers and discharging the aqueous layer. The organic stream was then washed with water (5V) after which both layers were discharged from the reactor. At that time, the aqueous streams were combined and charged back to the reactor before washing the aqueous streams thrice with ethyl acetate (60 V, total). The resulting organic streams were returned to the reactor before distilling the resulting solution to approximately 7 V, charging Compound I Form I seed crystals (0.03 equiv.) and then methyl tert-butyl ether (8 V) over about 2 hours. The resulting slurry was aged overnight at room temperature before being filtered. The solids were washed with MTBE (thrice, 20 V total) before drying in a vacuum oven to afford Compound I as Form I.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

What is claimed is:
1. A process for preparing a compound of formula I:

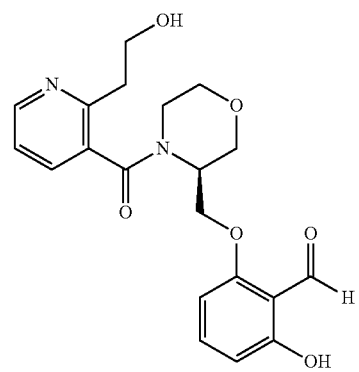

comprising:
(i) contacting a compound of formula 1:

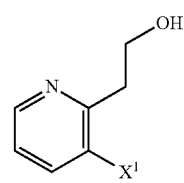

wherein $X^1$ is halo;
with a metalating reagent and carbon dioxide, wherein the metalating agent is a compound of formula X-M-R, and wherein M is a metal, R is an alkyl or aryl, and X is a halide or alkali metal, to form a compound of formula 2a:

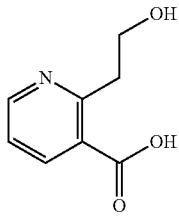
2a (ii) contacting a compound of formula 2a with a compound of formula:

PG-X² wherein PG is a hydroxy protecting group and X² is halo;
to form a compound of formula 3:

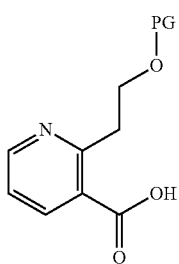
3

(iii) contacting a compound of formula 3 with a compound of formula 4:

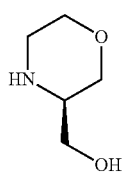
4 to form a compound of formula 5:

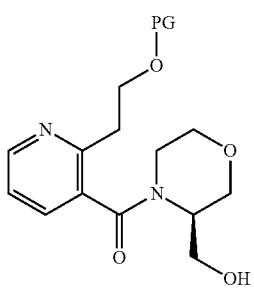
5

(iv) contacting a compound of formula 5 with a compound of formula 6:

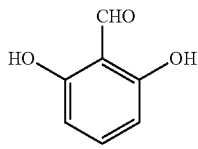
6 to form a compound of formula 7:

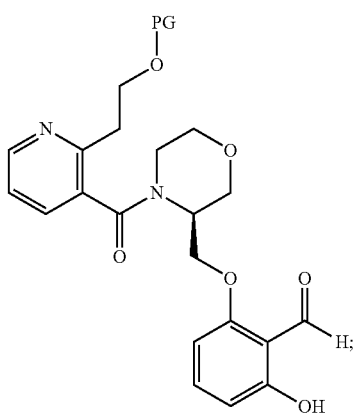
7 and (v) deprotecting a compound of formula 7 to form a compound of formula I.

2. The process of claim 1, wherein the metalating agent is isopropyl magnesium chloride.

3. The process of claim 1, wherein step (iii) comprise a coupling agent and a base.

4. The process of claim 1, wherein step (iv) comprise triphenylphosphine and diisopropyl azodicarboxylate.

5. The process of claim 1, wherein step (v) comprise tetrabutylammonium fluoride (TBAF).

6. A process for preparing a compound of formula I:

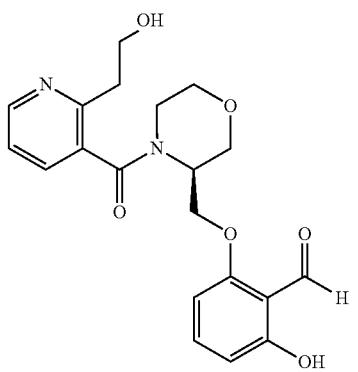
I comprising:
(i) contacting a compound of formula 2:

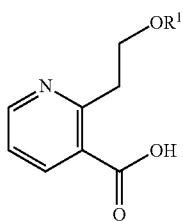

wherein R¹ is hydroxy protecting group;
with a compound of formula 10:

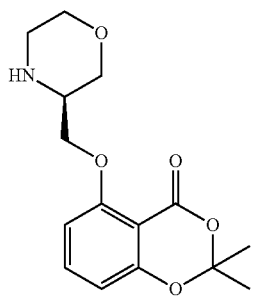

or a salt thereof,
to form a compound of formula 11:

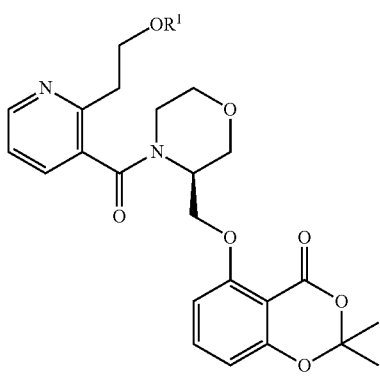

(ii) contacting a compound of formula 11 with a reductant to form a compound of formula 15:

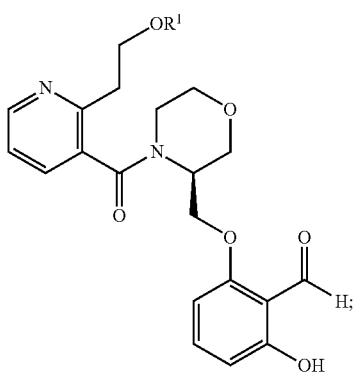

and
(iii) deprotecting a compound of formula 15 to form a compound of formula I.

7. The process of claim 6, wherein step (i) comprises a coupling agent and a base.

8. The process of claim 7, wherein the coupling agent is propylphosphonic anhydride.

9. The process of claim 6, wherein the reductant is lithium diisobutyl-t-butoxyaluminum hydride (LDBBA).

10. The process of claim 6, wherein step (iii) comprise a deprotecting reagent, wherein the deprotecting reagent is tetrabutylammonium fluoride (TBAF).

11. A process for preparing a compound of formula I:

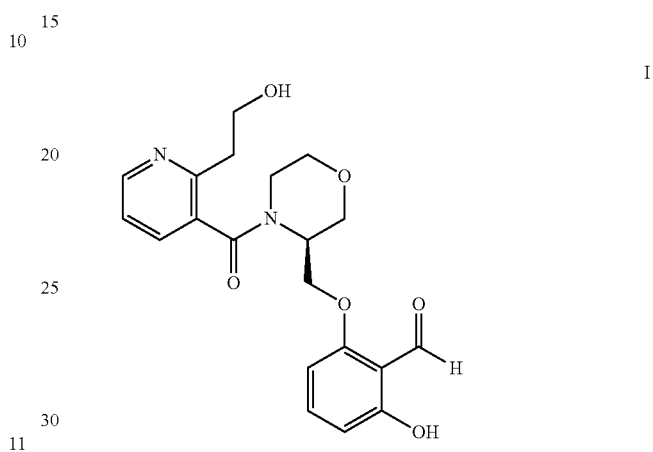

comprising:
(i) contacting a compound of formula 2:

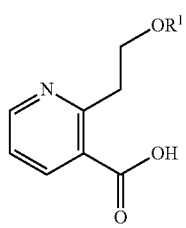

wherein R¹ is hydroxy protecting group;
with a compound of formula 10:

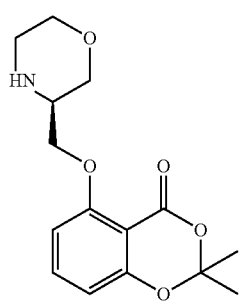

or a salt thereof, form a compound of formula 11:

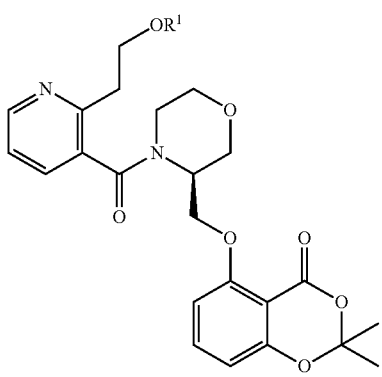

11

(ii) contacting a compound of formula 11 with lithium diisobutyl-t-butoxyaluminum hydride (LDBBA) to provide a compound of formula I.

12. The process of claim 11, wherein step (i) comprises a coupling agent and a base.

13. The process of claim 12, wherein the coupling agent is propylphosphonic anhydride.

14. The process of claim 11, wherein step (ii) further comprise a solvent selected from tetrahydrofuran (THF), 2-methyltetrahydrofuran, dichloromethane (DCM), methyl tert-butyl ether (MTBE), and ethyl acetate (EtOAc).

15. The process of claim 6, wherein the hydroxy protecting group is tert-butyldiphenylsilyl (TBDPS), acetyl (Ac), or benzoyl (Bz).

16. The process of claim 6, further comprising:
(iv) contacting a compound of formula 12:

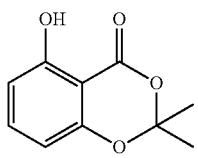

12 with a compound of formula 13:

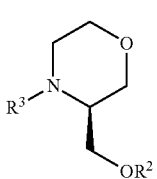

13 wherein:
$R^2$ is H; and $R^3$ is an amine protecting group;
to form a compound of formula 14:

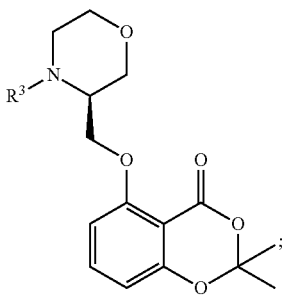

14

;

and (v) deprotecting a compound of formula 14 to form a compound of formula 10.

17. The process of claim 16, wherein step (iv) comprise triphenylphosphine and diisopropyl azodicarboxylate.

18. The process of claim 16, wherein step (v) comprise an acid.

19. The process of claim 18, wherein the acid is methanesulfonic acid.

* * * * *